US010702630B2

(12) United States Patent
Lewis et al.

(10) Patent No.: US 10,702,630 B2
(45) Date of Patent: Jul. 7, 2020

(54) TUBULAR TISSUE CONSTRUCT AND A METHOD OF PRINTING

(71) Applicant: President and Fellows of Harvard College, Cambridge, MA (US)

(72) Inventors: Jennifer A. Lewis, Cambridge, MA (US); Kimberly A. Homan, Somerville, MA (US); David B. Kolesky, Cambridge, MA (US); Ryan L. Truby, Boston, MA (US); Mark A. Skylar-Scott, Brookline, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 262 days.

(21) Appl. No.: 15/567,570

(22) PCT Filed: May 4, 2016

(86) PCT No.: PCT/US2016/030710
§ 371 (c)(1),
(2) Date: Oct. 18, 2017

(87) PCT Pub. No.: WO2016/179242
PCT Pub. Date: Nov. 10, 2016

(65) Prior Publication Data
US 2018/0110901 A1  Apr. 26, 2018

Related U.S. Application Data

(60) Provisional application No. 62/157,286, filed on May 5, 2015.

(51) Int. Cl.
| | |
|---|---|
| *A61L 27/38* | (2006.01) |
| *A61L 27/36* | (2006.01) |
| *A61L 27/50* | (2006.01) |
| *A61L 27/54* | (2006.01) |
| *B33Y 10/00* | (2015.01) |
| *B33Y 80/00* | (2015.01) |
| *B29C 64/106* | (2017.01) |
| *A61L 27/18* | (2006.01) |
| *A61L 27/56* | (2006.01) |
| *A61F 2/04* | (2013.01) |

(52) U.S. Cl.
CPC .......... *A61L 27/3804* (2013.01); *A61L 27/18* (2013.01); *A61L 27/3633* (2013.01); *A61L 27/3675* (2013.01); *A61L 27/3808* (2013.01); *A61L 27/3834* (2013.01); *A61L 27/3878* (2013.01); *A61L 27/3891* (2013.01); *A61L 27/50* (2013.01); *A61L 27/54* (2013.01); *A61L 27/56* (2013.01); *B29C 64/106* (2017.08); *B33Y 10/00* (2014.12); *B33Y 80/00* (2014.12); *A61F 2/04* (2013.01); *A61F 2240/002* (2013.01); *A61L 2300/62* (2013.01); *A61L 2300/64* (2013.01); *A61L 2400/08* (2013.01); *A61L 2430/26* (2013.01); *A61L 2430/32* (2013.01)

(58) Field of Classification Search
CPC .. A61L 27/3804; A61L 27/54; A61L 27/3808; A61L 27/50; A61L 27/3891; A61L 27/3633; A61L 27/56; A61L 2430/32; A61L 2430/26; B29C 64/106; B33Y 80/00; B33Y 10/00; A61F 2/04
See application file for complete search history.

(56) References Cited

U.S. PATENT DOCUMENTS

| | | | |
|---|---|---|---|
| 8,101,139 B2 | 1/2012 | Therriault et al. | |
| 9,657,261 B2 * | 5/2017 | Charest | ........ A61M 1/14 |
| 2002/0182241 A1 | 12/2002 | Borenstein et al. | |
| 2011/0270412 A1 | 11/2011 | Bellan et al. | |
| 2013/0084449 A1 | 4/2013 | Lewis et al. | |
| 2014/0228970 A1 | 8/2014 | Boland | |
| 2014/0314954 A1 | 10/2014 | Lewis et al. | |

FOREIGN PATENT DOCUMENTS

| | | |
|---|---|---|
| WO | WO 98/09582 A1 | 3/1998 |
| WO | WO 2010/009320 A1 | 1/2010 |
| WO | WO 2011/119607 | 9/2011 |
| WO | WO 2013/006399 | 1/2013 |
| WO | WO 2014/011775 A1 | 1/2014 |
| WO | WO 2015/069619 | 5/2015 |
| WO | WO 2016/179242 A1 | 11/2016 |

OTHER PUBLICATIONS

Ozoblat, Ibrahim, Bioprinting scale-up tissue and organ constructs for transplantation. Trends in Biotechnology, vol. 33, No. 7 (Jul. 2015) pp. 395-400 (Year: 2015).*
Groopman, Jerome, Print thyself, The New Yorker, Nov. 24, 2014 Issue. (Year: 2014).*
Fedorovich et al., Three-dimensional fiber deposition of cell-laden, viable, patterned constructs for bone tissue printing. Tissue Engineering Part A, vol. 14, No. 1 (2008) pp. 127-133. (Year: 2008).*
Communication dated Dec. 17, 2018 including Supplementary European Search Report dated Dec. 6, 2018 extended by the European Search Opinion received from the European Patent Office in the corresponding European Application No. 16 789 988.9.
International Search Report and Written Opinion received in PCT Application No. PCT/US2016/030710 dated Sep. 15, 2016.
Notification Concerning Transmittal of Copy and International Preliminary Report on Patentability received in PCT Application No. PCT/US2016/030710 dated Nov. 16, 2017 and International Preliminary Report dated Nov. 7, 2017.
Murphy, S.V., & Atala, A., "3D bioprinting of tissues and organs," *Nature Biotechnology*, 32(8):773-785 (2014).
Lee, K.Y. & Mooney, D.J., "Hydrogels for Tissue Engineering," *Chem Rev*, 101(7):1869-1880 (2001).

(Continued)

*Primary Examiner* — Kara D Johnson
(74) *Attorney, Agent, or Firm* — Brinks Gilson & Lione

(57) ABSTRACT

A 3D printed tubular construct, such as a nephron, with or without embedded vasculature as well as methods of printing tubular tissue constructs are described.

24 Claims, 49 Drawing Sheets

(56) References Cited

OTHER PUBLICATIONS

Mosesson, M.W., "Fibrinogen Structure and Fibrin Clot Assembly," *Semin Thromb Hemost*, 24(2):169-174 (1998).

Chen, R.-N., et al., "Characterization of collagen matrices cross-linked using microbial transglutaminase," *Biomaterials* 26(20):4229-4235 (2005).

Jayakumar, M.K.G., et al., "Remote activation of biomolecules in deep tissues using near-infrared-to-UV upconversion nanotransducers," *Proceedings of the National Academy of Sciences*, 109(22):8483-8488 (2012).

Klumpers, D.D., et al., "Cell mediated contraction in 3D cell-matrix constructs leads to spatially regulated osteogenic differentiation," *Integr Biol* (Camb), 5(9):1174-1183 (2013).

Oster, G.F., et al., "Mechanical aspects of mesenchymal morphogenesis," *J Embryol Exp Morphol*, 78:83-125 (1983).

Giulitti S., et al., "Optimal periodic perfusion strategy for robust long-term microfluidic cell culture," *Lab on a Chip*, 13(22):4430 (2013).

Griffith, L.G. & Swartz, M.A., "Capturing complex 3D tissue physiology in vitro," *Nat Rev Mol Cell Biol*, 7(3):211-224 (2006).

Price, G. & Tien, J., "Methods for Forming Human Microvascular Tubes In Vitro and Measuring Their Macromolecular Permeability," *Biological Microarrays: Methods and Protocols, Methods in Molecular Biology*, 671:281-293 (2011).

Kolesky, D.B., et al., "Three-dimensional bioprinting of thick vascularized tissues," *Proc Natl Acad Sci*, 113(12):3179-3184 (2016).

Kolesky, D.B., et al., "3D Bioprinting of Vascularized, Heterogeneous Cell-Laden Tissue Constructs," *Adv Mater*, 26:3124-3130 (2014).

Bensamoun, S.F., et al., "Stiffness imaging of the kidney and adjacent abdominal tissues measured simultaneously using magnetic resonance elastography," *Clin Imaging*, 35:284-287 (2011).

Jansen, J. et al., "Biotechnological challenges of bioartificial kidney engineering," *Biotechnol Adv*, 32:1317-1327 (2014).

Wu, W., et al., "Omnidirectional Printing of 3D Microvascular Networks," *Adv Mater*, 23:H178-183 (2011).

Furness, P.N., "Extracellular matrix and the kidney," *J Clin Pathol*, 49:355-359 (1996).

Wieser, M. et al., "hTERT alone immortalizes epithelial cells of renal proximal tubules without changing their functional characteristics," *Am J Physiol Renal Physiol*, 295:F1365-1375 (2008).

Pearson, A.L., et al., "Albumin induces interleukin-6 release from primary human proximal tubule epithelial cells," *Journal of Nephrology*, 21(6):887 (2008).

Mescher, A.L., "Epethelial Tissue," *Junqueira's Basic Histology, Text and Atlas, 13$^{th}$ edn*, 4:85-97 (2013).

Jang, K.J. et al., "Human kidney proximal tubule-on-a-chip for drug transport and nephrotoxicity assessment," *Integrative Biology*, 5:1119-1129 (2013).

Cui, S., et al., "Megalin/gp330 mediates uptake of albumin in renal proximal tubule," *Am J of Physiol (Renal Fluid Electrolyte Physiol 40)*, 271:F900-F907 (1996).

Gekle, M., "Renal Proximal Tubular Albumin Reabsorption: Daily Prevention of Albuminuria," *News Physiology Sci.*,13:5-11 (1998).

Norden, A.G. et al., "Urinary Megalin Deficiency Implicates Abnormal Tubular Endocytic Function in Fanconi Syndrome," *J Am Soc Nephrol*, 13:125-133 (2002).

Miller, J.S., et al., Rapid casting of patterned vascular networks for perfusable engineered 3D tissues, *Nat Mater*, 11(9):768-774 (2012).

Adler, M. et al., "A Quantitative Approach to Screen for Nephrotoxic Compounds In Vitro," *J Am Soc Nephrol*, 27:1-14 (2015).

\* cited by examiner

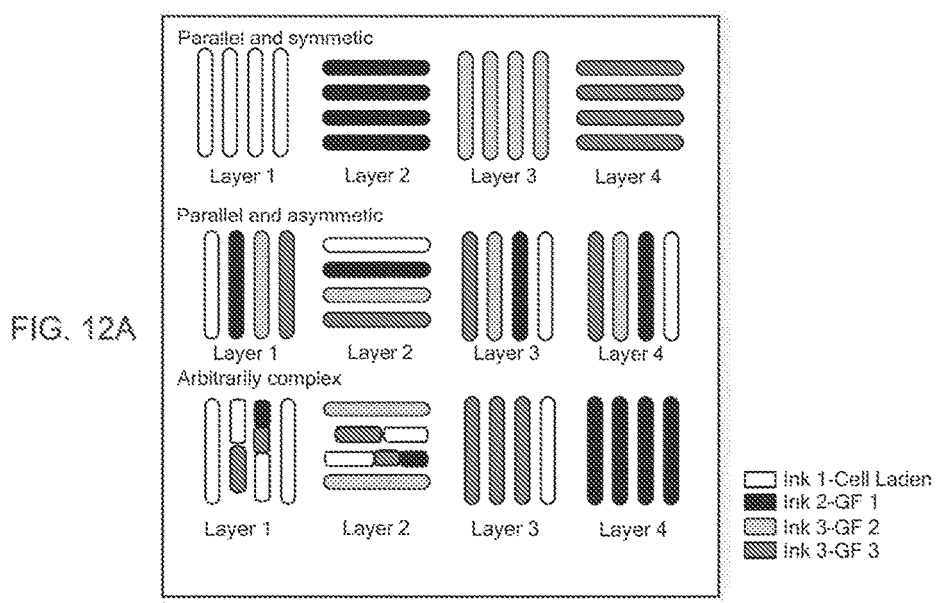
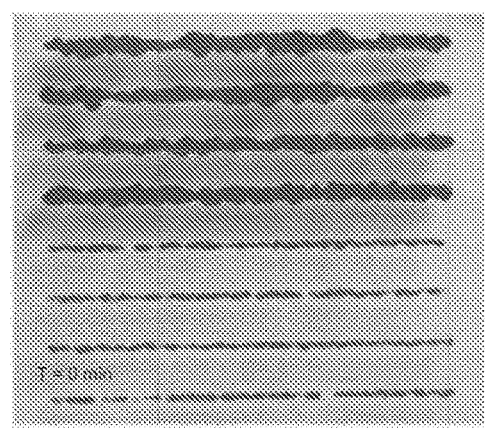
FIG. 12B
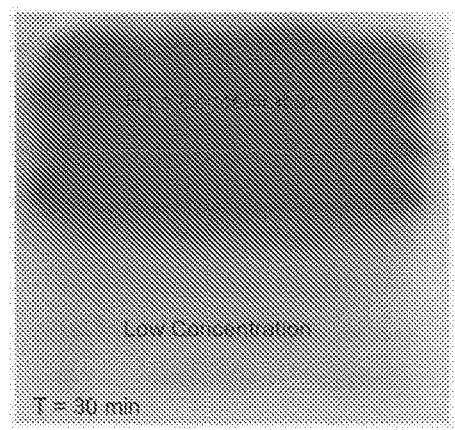
FIG. 12C
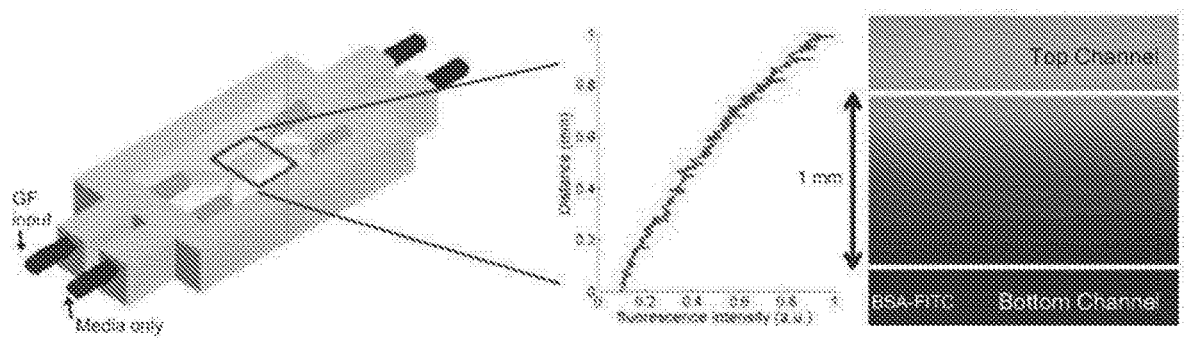
FIG. 12D  FIG. 12E  FIG. 12F

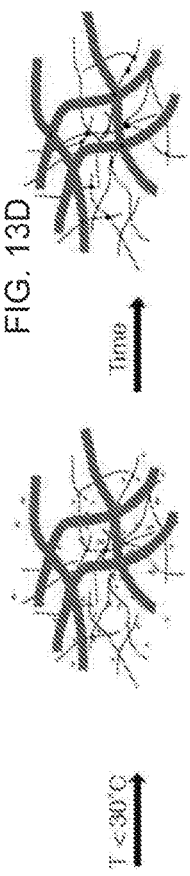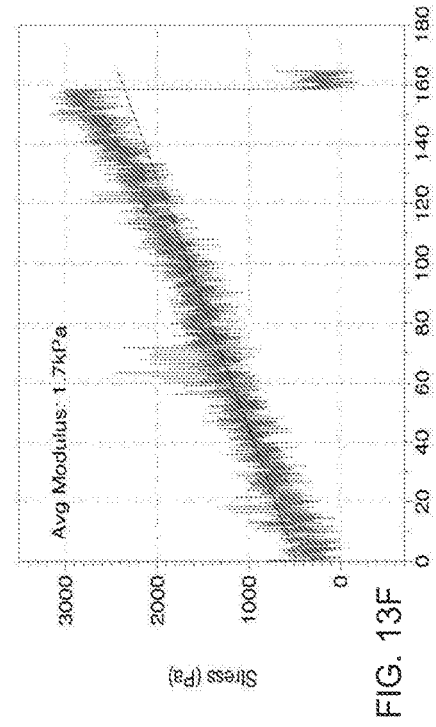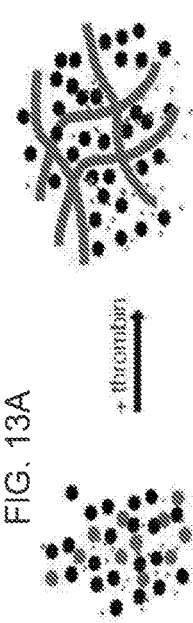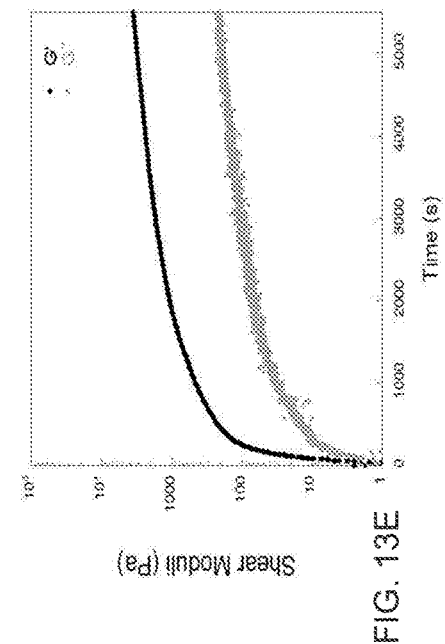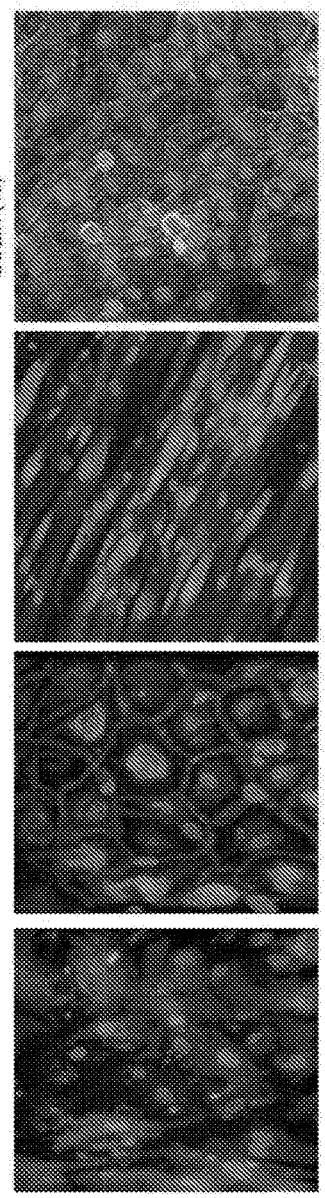
FIG. 13A FIG. 13B FIG. 13C FIG. 13D
FIG. 13E FIG. 13F
FIG. 13G Fibroblasts
FIG. 13H Endothelial cells
FIG. 13I Smooth Muscle cells
FIG. 13J Proximal tubule cells Print Endothelial cells Endothelial cells dispersed in Pluronic F127 and 3D printed Matrix encapsulation Channels are encapsulated with matrix material.

Evacuate

Structure is cooled to liquefy Pluronic F127. Left with a layer of cells on channel walls As printed HUVEC-Pluronic After casting and liquefying After 1 day of incubation After active perfusion for 24hrs

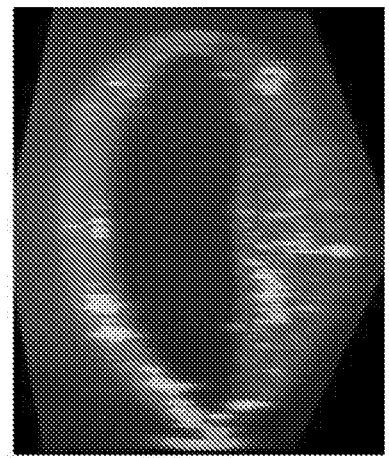
FIG. 17F
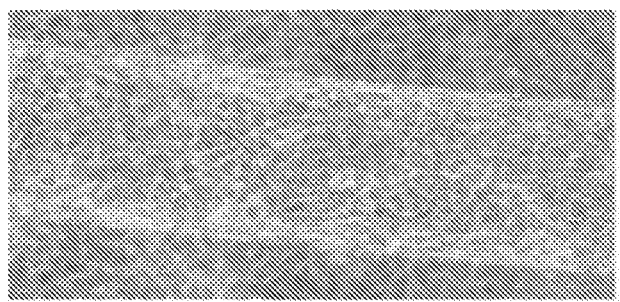
FIG. 17C
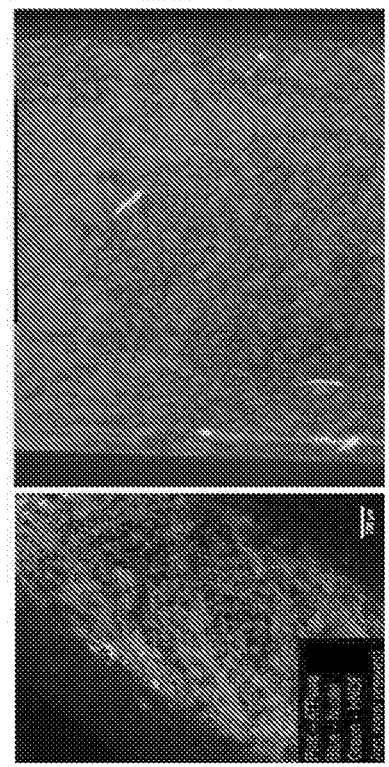
FIG. 17E
FIG. 17D

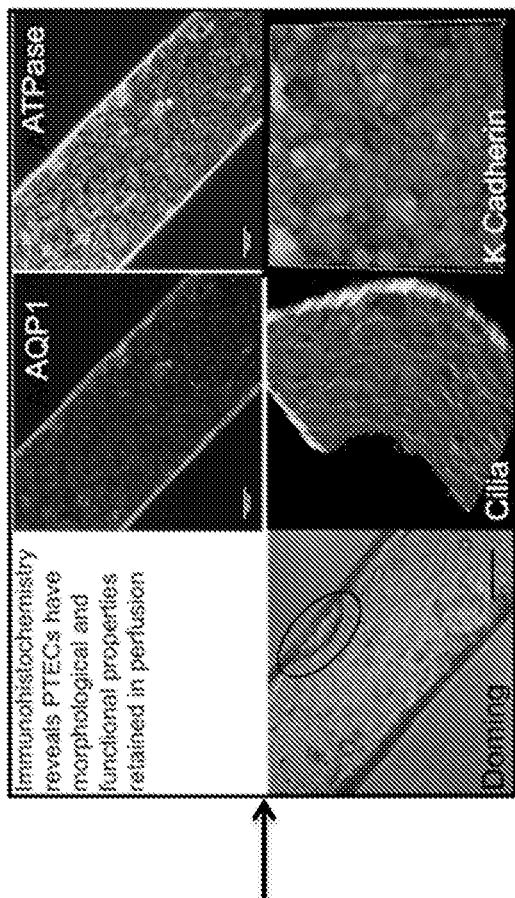
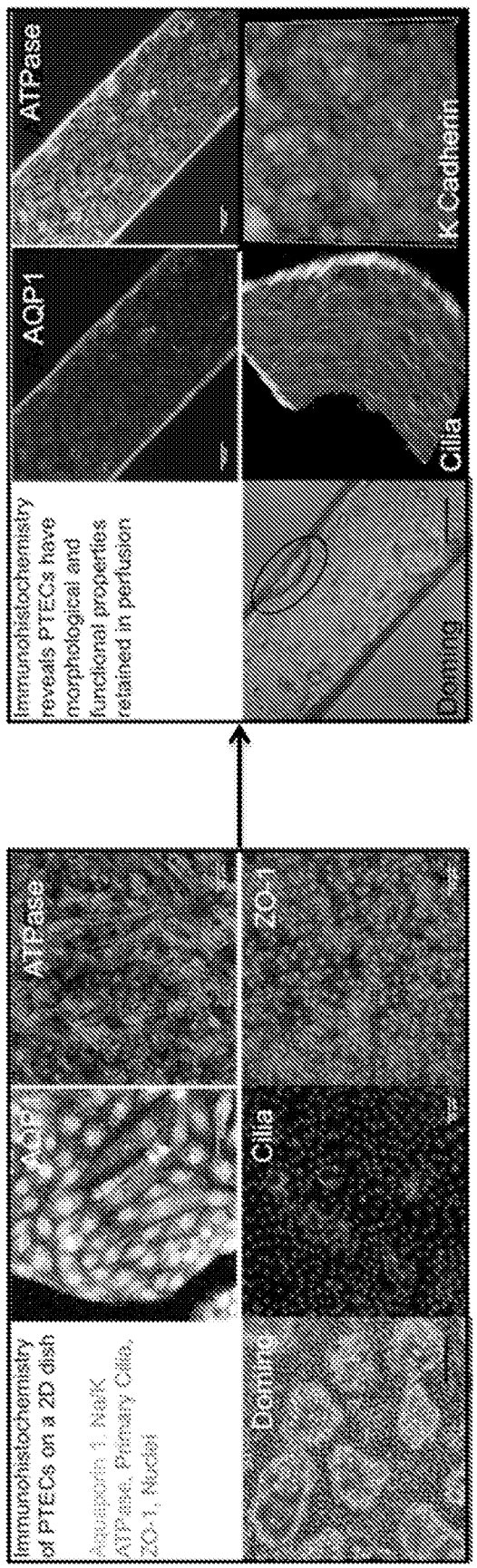
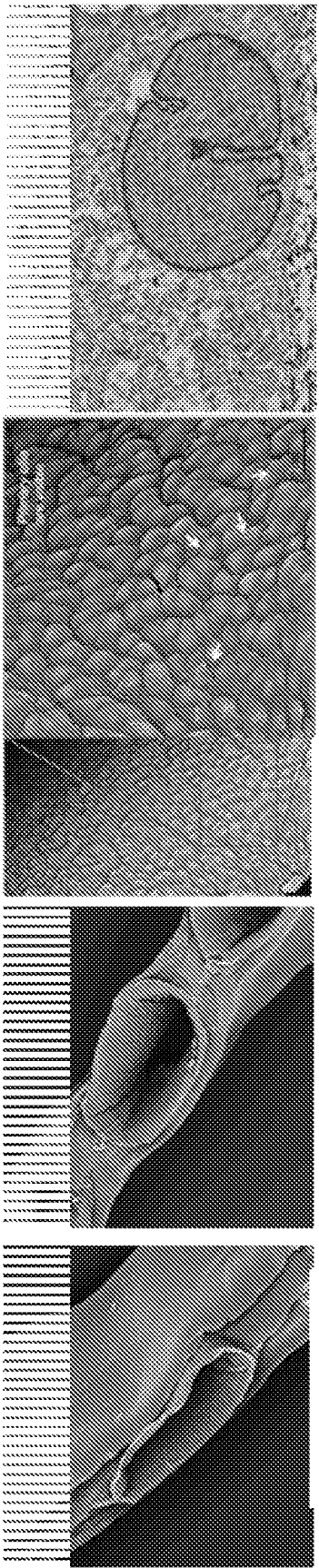
FIG. 17U  FIG. 17V  FIG. 17W  FIG. 17X

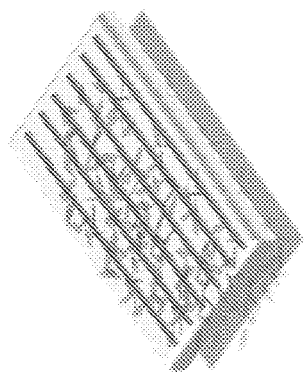
FIG. 19A
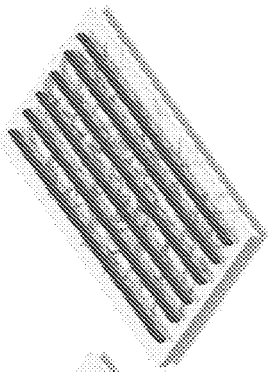
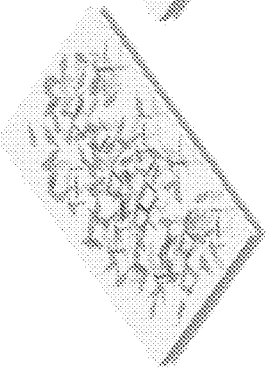
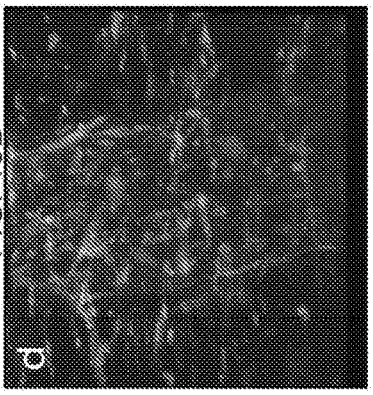
FIG. 19D
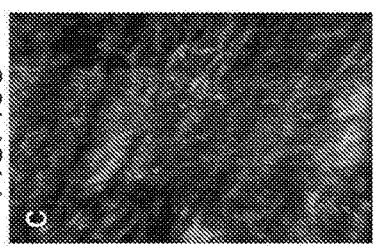
FIG. 19C
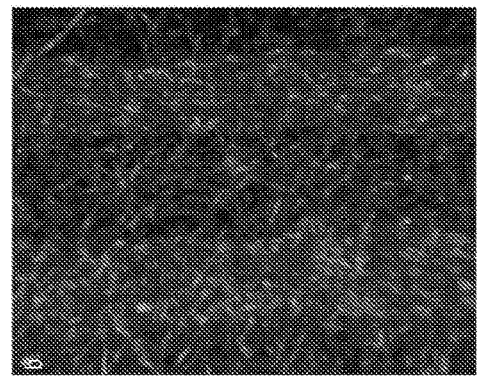
FIG. 19B
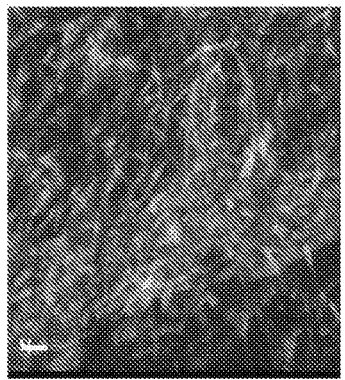
FIG. 19F
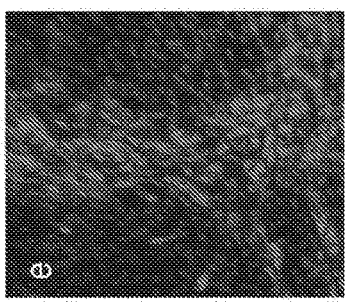
FIG. 19E

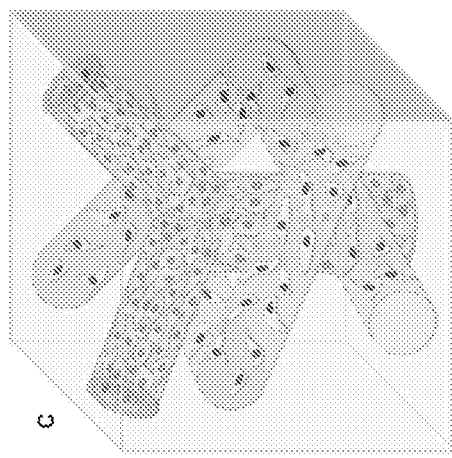
FIG. 21A
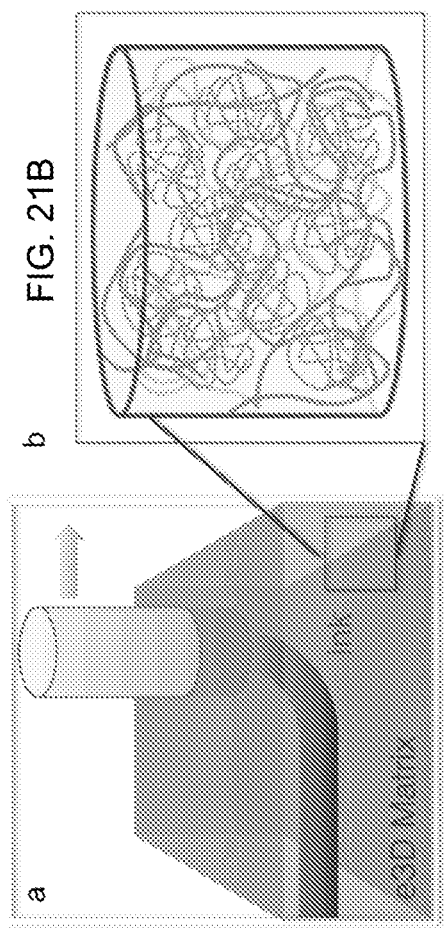
FIG. 21B
FIG. 21C
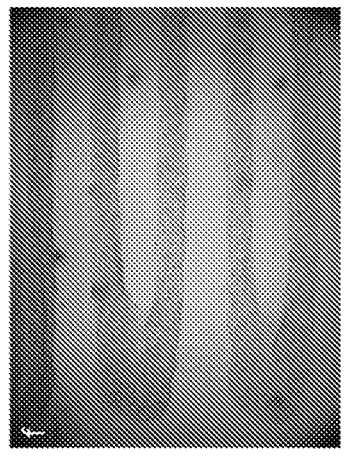
FIG. 21D
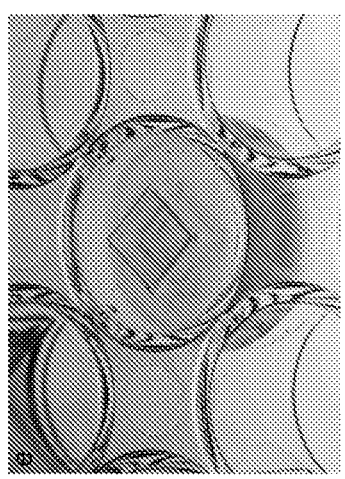
FIG. 21E
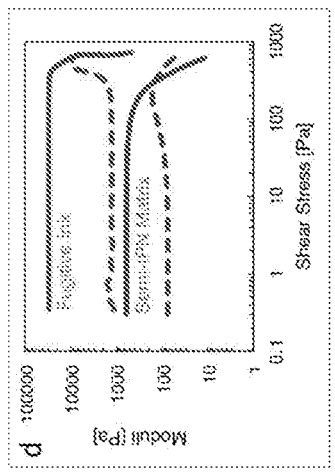
FIG. 21F

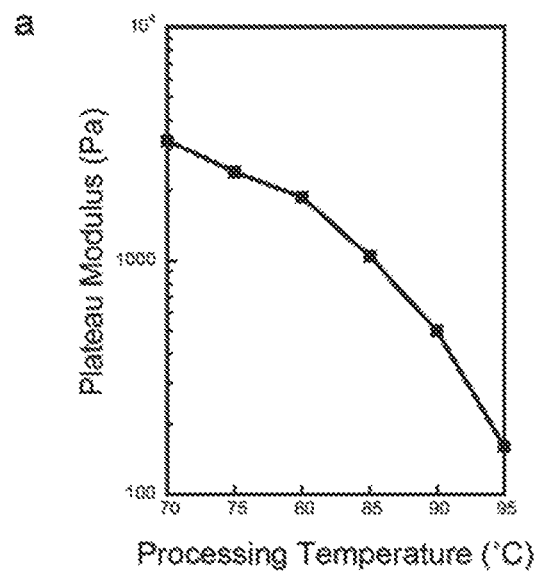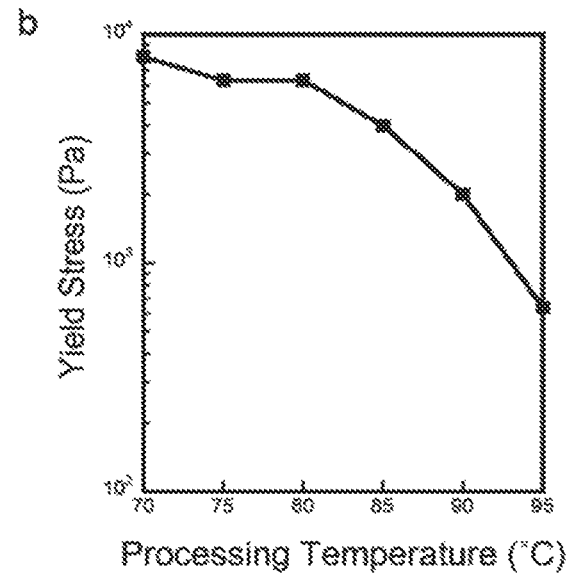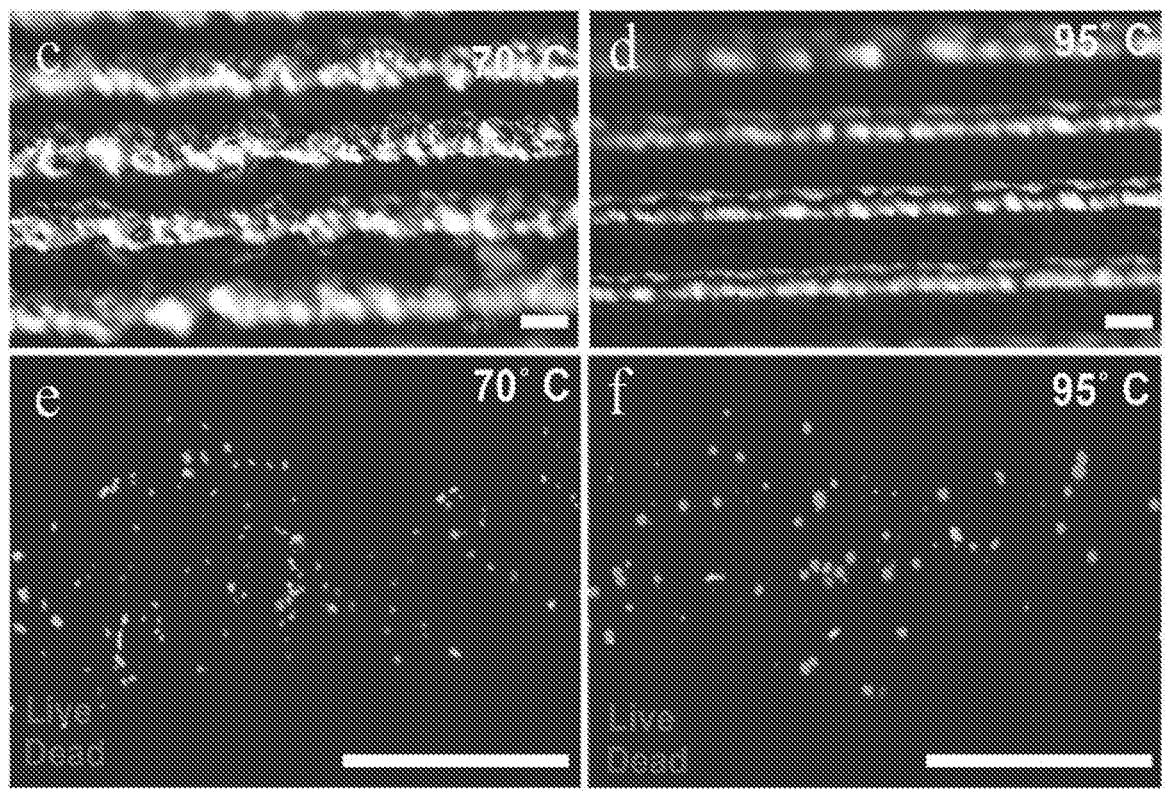
FIGs. 25A-25F

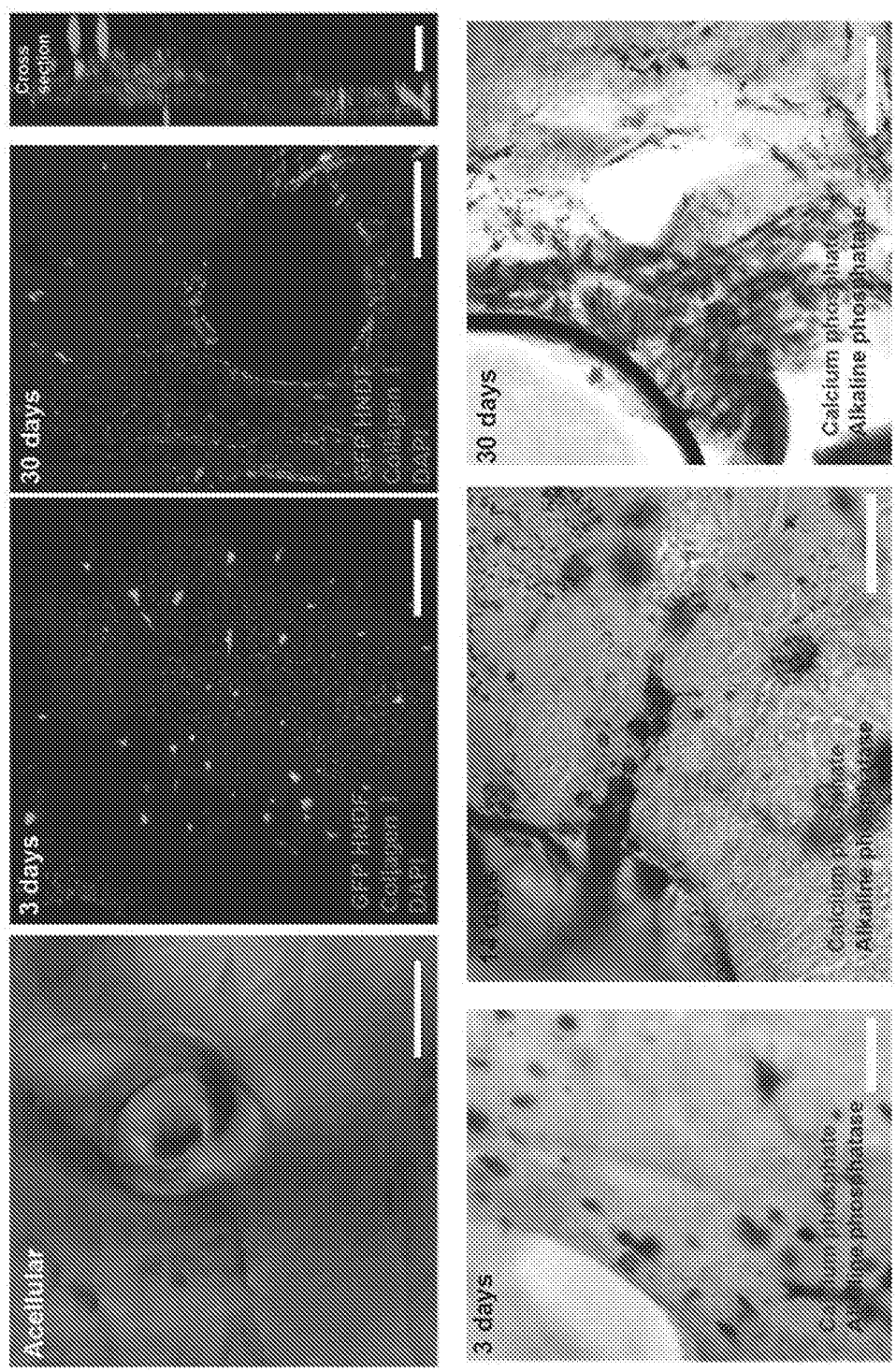

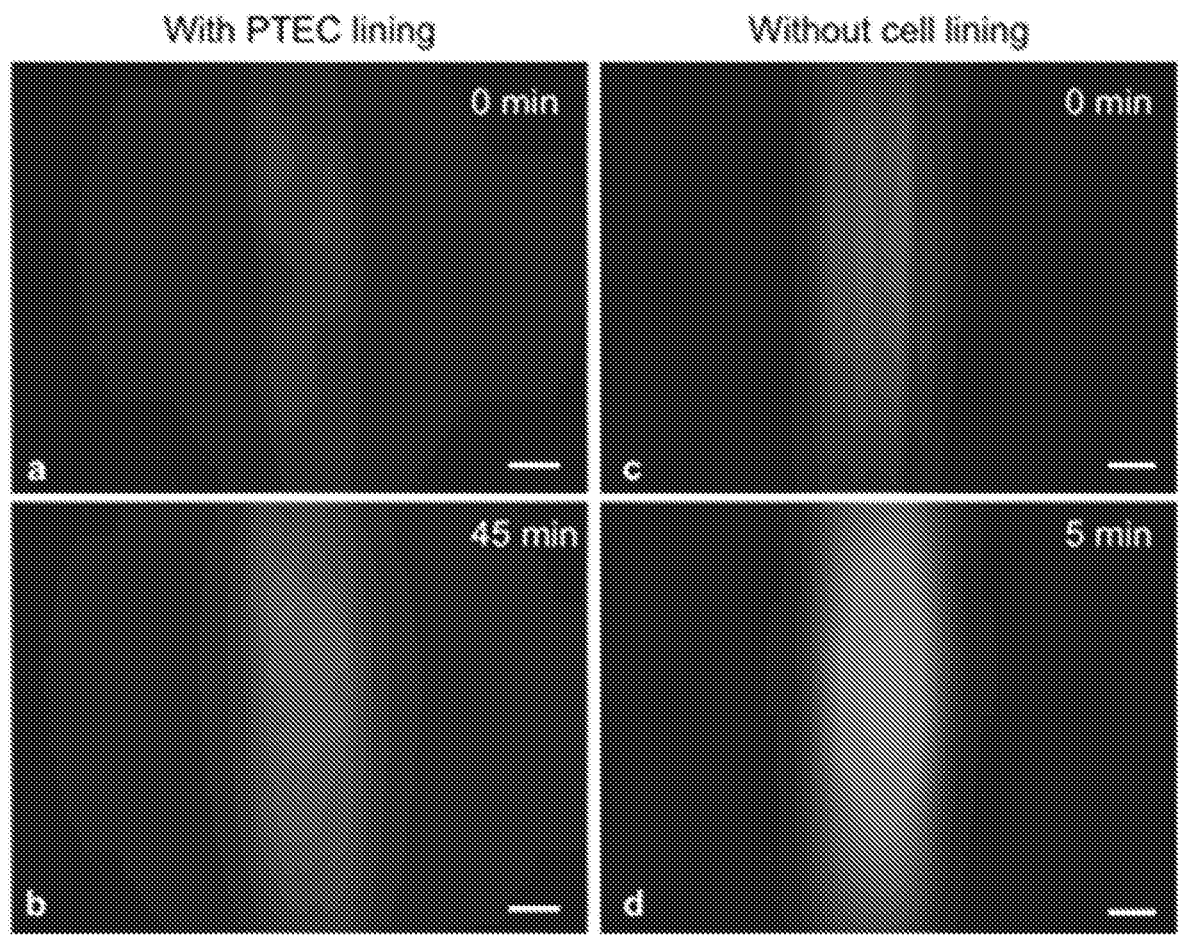
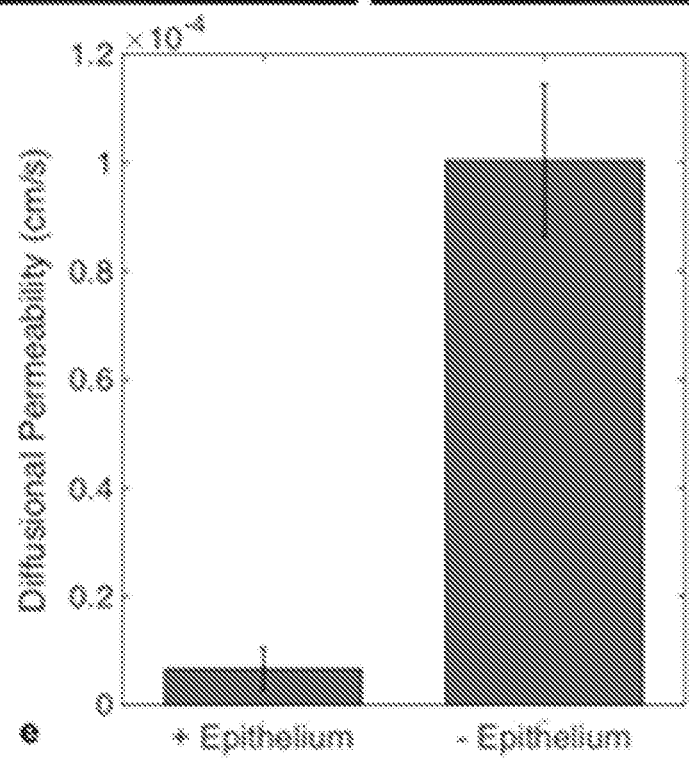
FIGs. 41A-41E

US 10,702,630 B2

TUBULAR TISSUE CONSTRUCT AND A METHOD OF PRINTING

RELATED APPLICATIONS

The present patent document is a § 371 filing based on PCT Application Serial No. PCT/US2016/030710, filed May 4, 2016, which claims the benefit of the filing date under 35 U.S.C. § 119(e) of Provisional U.S. Patent Application Ser. No. 62/157,286, filed May 5, 2015, which is hereby incorporated by reference.

All patents, patent applications and publications, and other literature references cited herein are hereby incorporated by reference in their entirety. The disclosures of these publications in their entireties are hereby incorporated by reference into this application in order to more fully describe the state of the art as known to those skilled therein as of the date of the invention described and claimed herein.

FEDERALLY SPONSORED RESEARCH OR DEVELOPMENT

This invention was made with Government support under contract number CMMI-1548261 awarded by the National Science Foundation EAGER. The Government has certain rights in this invention.

BACKGROUND

The present disclosure is related generally to tissue engineering and more particularly to fabricating tubular tissue constructs including embedded vasculature and/or tubules.

The ability to create three-dimensional (3D) vascularized tissues on demand could enable scientific and technological advances in tissue engineering, drug screening, toxicology, 3D tissue culture, and organ repair. To produce 3D engineered tissue constructs that mimic natural tissues and, ultimately, organs, several key components—cells, extracellular matrix (ECM), epithelium, and vasculature—may need to be assembled in complex arrangements. Each of these components plays a vital role: cells are the basic unit of all living systems, ECM provides structural support, epithelium provides a stromal functional unit, and vascular networks provide efficient nutrient and waste transport, temperature regulation, delivery of factors, and long-range signaling routes. Without perfusable vasculature within a few hundred microns of each cell, three-dimensional tissues may quickly develop necrotic regions. The inability to embed vascular networks in tissue constructs has hindered progress on 3D tissue engineering for decades.

The need to produce tubular tissue constructs is applicable to both embedded vasculature and embedded epithelial tissue. Our method extends broadly to epithelial networks in the body, such as nephrons, that include multiple types of cells along their lengths.

SUMMARY

Certain embodiments relate to a method of printing a tubular tissue construct. The method includes depositing one or more sacrificial filaments on and/or in a substrate to form a functional channel pattern. Each sacrificial filament comprises a fugitive ink and a plurality of predetermined types of viable cells, wherein each predetermined type of viable cells is deposited at a different predetermined location along a length of the sacrificial filament. The method also includes the steps of at least partially surrounding the functional channel pattern with an extracellular matrix composition and removing the fugitive ink to create one or more functional channels in the extracellular matrix composition. At least a portion of each different predetermined type of viable cells remains at the different predetermined location after removal of the fugitive ink, thereby forming a tubular tissue construct. The substrate may be a perfusable chip. The tubular construct may be exposed to one or more biological agents, a biological agent gradient, a pressure, and/or an oxygen tension gradient, wherein the one or more biological agents, the biological agent gradient, the pressure, and/or the oxygen tension gradient may further direct development, differentiation, and/or functioning of the tubular tissue construct. The tubular tissue construct may be a nephron or the tubule portion of the nephron, wherein the plurality of predetermined types of viable cells may include renal proximal tubule cells, loop of Henle cells, renal distal tubule cells, collecting duct cells, mesangial cells, renal microvascular cells, renal cell progenitors, pluri or multipotent stem cells, other endothelial lineage cells, fenestrated glomerular endothelial cells, induced pluripotent stem cells (iPSCs), and/or iPSCs-derived patent-specific pro-kidney or individual cell lines present in a nephron or the tubule portion of the nephron. Alternatively, the tubular tissue construct may be intestine, milk duct, sweat gland, colon, esophagus, stomach, airway epithelium, epididymus, urethra, liver bile duct, pancreatic duct, or lymph. The method may further include depositing one or more sacrificial filaments on and/or in the substrate to form an interpenetrating network of tubes, each of the sacrificial filaments comprising a second fugitive ink, and removing the second fugitive ink to create the interpenetrating network of tubes in the tubular tissue construct. The interpenetrating network of tubes may form vascular channels.

Certain further embodiments relate to another method of printing a tubular tissue construct. The method includes depositing one or more sacrificial filaments on and/or in a substrate to form a functional channel pattern. Each sacrificial filament comprises a fugitive ink and a plurality of predetermined types of binding domains, wherein each predetermined type of binding domain is deposited at a different predetermined location along a length of the sacrificial filament and is capable of binding to a predetermined type of target cell. The method also includes the steps of at least partially surrounding the functional channel pattern with an extracellular matrix composition and removing the fugitive ink to create one or more functional channels in the extracellular matrix composition. At least a portion of the different predetermined types of binding domains remains at the different predetermined locations after removal of the fugitive ink. The method also includes a step of injecting a suspension comprising at least one predetermined type of target cells into the functional channel, wherein the target cells bind to corresponding predetermined types of binding domains, thereby forming a tubular tissue construct. In certain embodiments, the suspension comprises multiple predetermined types of target cells. The binding domains for the target cells may be proteins, e.g., antibodies; DNA; RNA; aptamers; nanoparticles; bacteria; or combinations thereof. The substrate may be a perfusable chip. The tubular construct may be exposed to one or more biological agents, a biological agent gradient, a pressure, and/or an oxygen tension gradient, wherein the one or more biological agents, the biological agent gradient, the pressure, and/or the oxygen tension gradient may further direct development, differentiation, and/or functioning of the tubular tissue construct. The tubular tissue construct may be a nephron, wherein the at least one predetermined type of target cells is selected from the group consisting of renal proximal tubule cells, loop of Henle cells, renal distal tubule cells, collecting duct cells, fenestrated glomerular endothelial cells, induced pluripotent stem cells (iPSCs), and/or iPSCs-derived patent-specific pro-kidney or individual cell lines present in a nephron. In certain embodiments, the tubular tissue construct may be any other tubular organ, such as intestine, milk duct, sweat gland, colon, esophagus, stomach, airway epithelium, epididymus, urethra, liver bile duct, pancreatic duct, or lymph. The at least partial surrounding of the functional channel pattern with the extracellular matrix composition may occur during deposition of the one or more sacrificial filaments, the one or more functional channel patterns thereby being formed and embedded simultaneously in the extracellular matrix composition. The method may further include depositing one or more sacrificial filaments on and/or in the substrate to form a vascular pattern interpenetrating the functional channel pattern, each of the sacrificial filaments comprising a second fugitive ink, and removing the second fugitive ink to create vascular channels in the extracellular matrix composition, thereby forming an interpenetrating vascular network in the tubular tissue construct. The method may further include injecting a suspension of viable epithelial cells into the one or more vascular channels.

Yet further embodiment relates to a printed tubular tissue construct that includes one or more functional channels comprising a patterned cell layer thereon along the length of the functional channel, the patterned cell layer comprising one or more types of viable cells, each type of viable cells being positioned along a different predetermined location of the functional channel and an extracellular matrix composition at least partially surrounding the one or more functional channels. The patterned cell layer may include a plurality of viable cells of at least two predetermined types. The patterned cell layer may include renal proximal tubule cells, loop of Henle cells, distal tubule cells, collecting duct cells, fenestrated glomerular endothelial cells, induced pluripotent stem cells (iPSCs), and/or iPSCs-derived patent-specific pro-kidney or individual cell lines present in a nephron, each distributed along a different predetermined location of the nephron. The tubular tissue construct may be a nephron. In alternative embodiment, the tubular tissue construct may be any other tubular organ, such as intestine, milk duct, sweat gland, colon, esophagus, stomach, airway epithelium, epididymus, urethra, liver bile duct, pancreatic duct, or lymph. The extracellular matrix composition at least partially surrounds the one or more tissue patterns. The printed tubular tissue construct may further include a network of vascular channels in the extracellular matrix composition. Alternatively, the printed tubular tissue construct may further include a channel or a network of epithelial channels in the extracellular matrix composition.

Certain further embodiments relate to a printed tubular tissue construct with embedded vasculature that includes one or more functional channels comprising a patterned cell layer thereon along the length of the functional channel, the patterned cell layer comprising one or more types of viable cells, each type of viable cells being positioned along a different predetermined location of the functional channel. The printed tubular tissue construct with embedded vasculature also includes a network of vascular channels interpenetrating the one or more functional channels and an extracellular matrix composition at least partially surrounding the one or more functional channels and the network of vascular channels. The patterned cell layer may include a plurality of viable cells of at least two predetermined cell types, wherein the extracellular matrix composition at least partially surrounds the one or more tissue patterns. The printed tubular tissue construct may be a nephron, wherein the patterned cell layer comprises at least two of renal proximal tubule cells, loop of Henle cells, renal distal tubule cells, collecting duct cells, mesangial cells, renal microvascular cells, renal cell progenitors, pluri or multipotent stem cells, other endothelial lineage cells, fenestrated glomerular endothelial cells, induced pluripotent stem cells (iPSCs), and/or iPSCs-derived patent-specific pro-kidney or individual cell lines present in a nephron. In certain alternative embodiments, the printed tubular tissue construct with embedded vasculature may be wherein the tubular tissue construct is intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph.

Yet another embodiment relates to a method of printing a nephron, the method including depositing one or more continuous sacrificial filaments on and/or in a substrate to form a functional channel. Each sacrificial filament comprises a first fugitive ink formulation over a first length of the sacrificial filament, a second ink formulation over a second length of the sacrificial filament, and a third ink formulation over a third length of the sacrificial filament, wherein the first fugitive ink formulation comprises a fugitive ink and renal proximal tubule cells, the second fugitive ink formulation comprises the fugitive ink and loop of Henle cells, and the third fugitive ink formulation comprises the fugitive ink and renal distal tubule cells. The method also includes the steps of at least partially surrounding the functional channel pattern with an extracellular matrix composition and removing the fugitive ink to create one or more functional channels in the extracellular matrix composition, at least a portion of the renal proximal tubule cells remaining along the first length of the one or more functional channels after removal of the first ink, at least a portion of the loop of Henley cells remaining in the second length of the one or more functional channels after removal of the second ink, and at least a portion of the distal tubule cells remaining in the third length of the one or more functional channels after removal of the third ink, thereby forming a nephron. The substrate may be a perfusable chip. The nephron may be exposed to one or more biological agents, a biological agent gradient, a pressure, and/or an oxygen tension gradient, wherein the one or more biological agents, the biological agent gradient, the pressure, and/or the oxygen tension gradient may further direct development, differentiation, and/or functioning of the nephron. The depositing one or more continuous sacrificial filaments on and/or in a substrate to form a functional channel may be through a single printhead. The step of depositing one or more continuous sacrificial filaments on and/or in the substrate to form a functional channel includes providing a nozzle body comprising at least a first ink delivery channel, a second ink delivery channel and a third ink delivery channel in fluid communication with a nozzle outlet, and forcing the first ink formulation to flow through the first ink delivery channel while preventing the second ink formulation and the third ink formulation from flowing through the second delivery channel and the third delivery channel, respectively, thereby extruding through the nozzle outlet the continuous sacrificial filament comprising the first ink formulation over the first predetermined length thereof. The method also includes the step of applying a withdrawal pulse to the first ink delivery channel while applying an infusion pulse to the second ink delivery channel, thereby forcing the second ink formulation to flow through the second ink delivery channel while preventing the first ink formulation and the third ink formulation from flowing through the first delivery channel and the third delivery channel, respectively, thereby extruding through the nozzle outlet the continuous sacrificial filament comprising the second ink formulation over the second predetermined length thereof. The method further includes the step of applying a withdrawal pulse to the second ink delivery channel while applying an infusion pulse to the third ink delivery channel, thereby forcing the third ink formulation to flow through the third ink delivery channel while preventing the first ink formulation and the second ink formulation from flowing through the first delivery channel and the second delivery channel, respectively, thereby extruding through the nozzle outlet the continuous sacrificial filament comprising the third ink formulation over the third predetermined length thereof, thereby 3D printing the one or more continuous sacrificial filaments comprising multiple cell types over different predetermined lengths of the filaments.

A further embodiment relates to a 3D printed nephron comprising one or more functional channels comprising a patterned cell layer thereon along the length of the functional channel, wherein the patterned cell layer includes renal proximal tubule cells over a first predetermined length of the one or more functional channel, loop of Henle cells over a second predetermined length of the one or more functional channel, and renal distal tubule cells over a third predetermined length of the one or more functional channel, and an extracellular matrix composition at least partially surrounding the one or more functional channels. The 3D printed nephron may further include collecting duct cells, fenestrated glomerular endothelial cells, induced pluripotent stem cells (iPSCs), and/or iPSCs-derived patent-specific pro-kidney or individual cell lines present in a nephron along different lengths of the function channel. The 3D printed nephron may further include one or more tissue patterns, each tissue pattern including a plurality of viable cells of one or more predetermined cell types, wherein the extracellular matrix composition at least partially surrounds the one or more tissue patterns. The 3D printed nephron may further include a network of vascular channels in the extracellular matrix composition.

Yet another embodiment relates to a method of printing a nephron, the methods includes depositing one or more continuous sacrificial filaments on and/or in a substrate to form a functional channel, each sacrificial filament comprising a first fugitive ink formulation over a first length of the sacrificial filament, a second ink formulation over a second length of the sacrificial filament, and a third ink formulation over a third length of the sacrificial filament, wherein the first fugitive ink formulation comprises a fugitive ink and a first predetermined type of binding domains to target renal proximal tubule cells, the second fugitive ink formulation comprises the fugitive ink and a second predetermined type of binding domains to target loop of Henle cells, and the third fugitive ink formulation comprises the fugitive ink and a third predetermined type of binding domains to target renal distal tubule cells, at least partially surrounding the functional channel pattern with an extracellular matrix composition, removing the fugitive ink to create one or more functional channels in the extracellular matrix composition, at least a portion of the first predetermined type of binding domains remaining along the first length of the one or more functional channels after removal of the ink, at least a portion of the second predetermined type of binding domains remaining in the second length of the one or more functional channels after removal of the ink, and at least a portion of the third predetermined type of binding domains remaining in the third length of the one or more functional channels after removal of the ink, and injecting a suspension comprising at least one of renal proximal tubule cells, loop of Henle cells and renal distal tubule cells into the functional channel, wherein the cells bind to their corresponding predetermined binding domains, thereby forming a nephron. The suspension may include renal proximal tubule cells, loop of Henle cells and renal distal tubule cells. The binding domains may be peptides, proteins, e.g., antibodies; DNA; RNA; aptamers; nanoparticles; small molecules, chemical functional groups, bacteria; or a combination thereof. In certain embodiments, the extracellular matrix surrounding the patterned sacrificial filaments contains predetermined coupling moieties to capture the binding domains from the sacrificial filament. The coupling moieties are chemically reactive to the binding domains, thereby locally capturing said binding domains upon contact before, during, or subsequent to the evacuation of the sacrificial filament. The coupling moieties comprise native extracellular matrix binding domains, antibodies, peptides, proteins, DNA, RNA, aptamers, nanoparticles, small molecules, chemical functional groups, and bacteria. The method may further include the steps of depositing one or more sacrificial filaments on or in the substrate to form a vascular pattern interpenetrating the functional channel pattern, each of the sacrificial filaments comprising a second fugitive ink and removing the second fugitive ink to create vascular channels in the extracellular matrix composition, thereby forming an interpenetrating vascular network in the tubular tissue construct and injecting a suspension of viable epithelial cells into the one or more vascular channels. The substrate may be a perfusable chip. The nephron may be exposed to one or more biological agents, a biological agent gradient, a pressure, and/or an oxygen tension gradient, wherein the one or more biological agents, the biological agent gradient, the pressure, and/or the oxygen tension gradient may further direct development, differentiation, and/or functioning of the nephron.

Yet another embodiment relates to a method of printing a tubular tissue construct, where the method includes depositing one or more cell-laden filaments each comprising a plurality of predetermined types of viable cells on and/or in a substrate to form one or more tissue patterns, each of the tissue patterns comprising at least two predetermined cell types, wherein each predetermined type of viable cells is deposited at a different predetermined location along a length of the cell-laden filament. The method also includes depositing one or more sacrificial filaments on and/or in the substrate to form a functional channel pattern interpenetrating the one or more tissue patterns, each of the sacrificial filaments comprising a fugitive ink, at least partially surrounding the one or more tissue patterns and the functional channel pattern with an extracellular matrix composition, and removing the fugitive ink to create functional channels in the extracellular matrix composition, thereby forming an interpenetrating channel network in a tissue construct. The substrate may be a perfusable chip. The tubular construct may be exposed to one or more biological agents, a biological agent gradient, a pressure, and/or an oxygen tension gradient, wherein the one or more biological agents, the biological agent gradient, the pressure, and/or the oxygen tension gradient may further direct development, differentiation, and/or functioning of the tubular tissue construct. The one or more cell-laden filaments may include an extracellular matrix material, such as gelatin, fibrin, gelatin methacrylate, collagen I, collagen III, collagen IV, fibrinogen, matrigel, laminin, carbopol, N-Isopropylacrylamide (NIPAAM), Polyethylene glycol (PEG), gelatin methacrylate (GelMA), Polyhydroxyethylmethacrylate (PHEMA), silk, hyaluronic acid, growth factors, proteoglycans like heparin sulfate or others and/or combinations thereof. In the method, at least one of the one or more cell-laden filaments may further include one or more functional chemical substances selected from the group consisting of: drugs, small molecules, toxins, proteins, and hormones. The tubular tissue construct may be a nephron, where the predetermined types of viable cells include renal proximal tubule cells, loop of Henle cells, renal distal tubule cells, collecting duct cells, fenestrated glomerular endothelial cells, induced pluripotent stem cells (iPSCs), and/or iPSCs-derived patent-specific pro-kidney or individual cell lines present in a nephron. Alternatively, the tubular tissue construct may be intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph. The method may further include depositing one or more sacrificial filaments on and/or in the substrate to form a vascular pattern interpenetrating the functional channel pattern, each of the sacrificial filaments comprising a second fugitive ink, and removing the second fugitive ink to create vascular channels in the extracellular matrix composition, thereby forming an interpenetrating vascular network in the tubular tissue construct. The method may further include injecting a suspension of viable epithelial cells into the one or more vascular channels.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 12A-12C show a schematic and images that illustrate the shaping of growth factor (GF) gradients by direct printing of a GF-laden extracellular matrix material comprising fibrin-gelatin.

FIG. 12D show an exemplary mold for perfusion of parallel printed vascular channels with fluorescently labeled BSA in only one channel.

FIGS. 12E and 12F show that a nearly linear gradient is generated between the two channels of FIG. 12D in 24 hours.

FIGS. 13A-13D illustrate the synthesis of a fibrin-gelatin interpenetrating polymer network. First, gel precursors are mixed together with transglutaminase (TG). Then, by polymerizing fibrinogen via the enzyme thrombin, a fibrin network is formed. The second phase is then formed around the fibrin gel, and the two phases are slowly crosslinked together via TG.

FIGS. 13E-13F show mechanical properties of the fibrin-gelatin matrix material.

FIGS. 13G-13J show the diversity of the fibrin-gelatin matrix adhesivity for fibroblasts (connective tissue), smooth muscle cells, endothelial cells, and renal proximal tubule (epithelial) cells, respectively.

FIGS. 17B-17C shows two functional channels in an extracellular matrix composition where the channels are lined with epithelial cells.

FIGS. 17D-17F show various confocal microscopy images of PTEC-lined channels and immunofluorescence images with various cell-specific proteins being expressed, including Na/K ATPase.

FIGS. 17J-N show proximal tubule epithelial cells (PTECs) stained using immunofluorescence for several functional properties on a 2D dish (AQPI (17J), ATPase (17K), Doming (17L), Cilia (17M), ZO-I (17N)) and the presence of domes in culture.

FIGS. 17O-T show perfused tubule constructs stained using immunofluorescence for several functional properties on a 2D dish (AQPI (17O), ATPase (17P), Doming (17R), Cilia (17S), ZO-I (17T)). The properties were retained or enhanced in the perfused tubule constructs.

FIGS. 17 U-X show SEM and TEM images of the tubules highlighting the confluent nature of the cells in the constructs, primary cilia, and formation of a brush border.

FIGS. 19A-19F show that, after printing a fugitive ink directly onto a cell-laden matrix, encapsulating with more cell-laden matrix, evacuating the fugitive ink to form vascular channels, and seeding the vascular channels with HUVECs, the endothelial cells form confluent layers and assemble into capillary structures over time.

FIG. 21A shows a schematic depicting an embedded printing process.

FIG. 21B shows a schematic of an extracellular matrix composition comprising a semi-interpenetrating polymer network (IPN) (e.g., PAA-GelMA) suitable for embedded printing.

FIG. 21C illustrates a complex heterogeneous structures with arbitrary 3D shape that may be constructed by embedded printing.

FIG. 21D provides representative rheological measurements of ink and matrix rheology appropriate for embedded printing.

FIG. 21E is a photograph of a vascular cube including a vascular network formed by embedded printing.

FIG. 21F shows a printed cell-laden filament within a semi-IPN extracellular matrix composition.

FIG. 25A depicts a graph showing results of gelatin processing time on cell viability exhibiting a lower plateau shear elastic modulus.

FIG. 25B depicts a graph showing results of gelatin processing time on cell viability exhibiting a lower shear yield stress.

FIGS. 25C and 25D show photographs showing that printed cell-laden filaments are less uniform if the gelatin is solubilized at 70° C. (FIG. 25C) compared to those produced by gelatin solubilized at 95° C. (FIG. 25D), Scale bars=250 μm.

FIG. 27A depicts a schematic illustration of the tissue manufacturing process.

FIG. 27B depict a picture of HUVECs growing on top of the matrix in 2D, scale bar=50 μm.

FIG. 27C depicts a picture of HNDFs growing inside the matrix in 3D, scale bar=50 μm.

FIG. 27D depicts a picture of hMSCs growing on top of the matrix in 2D, scale bar=50 μm.

FIGS. 27E and 27F depict images of printed hMSC-laden ink prepared using 95° C. processed gelatin as printed (FIG. 27E) and after 3 days in the 3D printed filament where actin (green) and nuclei (blue) are stained (FIG. 27F).

FIG. 33D is a high resolution image showing oscteocalcin (purple) localized within hMSCs and they appear to take on symmetric osteoblast-like morphologies after 30 days, scale bar=100 μm.

FIG. 35A depicts images of maturation of thick vascularized tissues differentiated toward an osteogenic lineage in situ. Thick vascularized tissue is analyzed at various time points to visualize maturation. Collagen-I (pink) deposition is not present in acelullar scaffolds and is instead secreted by the cells in the tissue, after 3 days there is very little collagen in regions near hMSCs and HNDFs, however, by day 30, printed hMSCs have produced significant collagen in both filaments and circumferentially around the vascular channels, scale bars=100 μm.

FIG. 35B depicts images of maturation of thick vascularized tissues differentiated toward an osteogenic lineage in situ. The delivery of an osteogenic cocktail through the vascular network has led to first the osteogenic lineage commitment of hMSCs and then the deposition of mineral over the course of 30 days. This is evidenced by appearance of alkaline phosphatase expression, which is observable via fast blue, and subsequent CaP mineralization—observable via alizarin red stain; scale bars=100 μm.

FIGS. 39A-39K depict a 3D proximal tubule maturation process.

FIG. 39A is a photo of a mature (fully confluent) tubule.

FIG. 39B depicts PTEC loading at Day 0, scale bar=500 μm.

FIG. 39C depicts higher magnification view of PTEC loading of FIG. 39B, scale bar=300 μm.

FIG. 39D shows PTECs adhering to the tubule at Day 1 after non-adherent cells are flushed away, scale bar=200 μm.

FIG. 39E depicts a low magnification view of PTECs growing into the tubule at Day 2, scale bar=500 μm.

FIG. 39F is an image at Day 4 where cells grow from colonies or clusters, scale bar=100 μm.

FIG. 39G shows an image at Day 4 where cells are near confluency, scale bar=100 μm.

FIG. 39H shows an image of a mature tubule at Day 38, scale bar=500 μm.

FIG. 39I shows a higher magnification view of the confluent tubule at Day 38 shown in FIG. 39H, scale bar=100 μm.

FIG. 39J shows an image of the tubule, which approaches within 350 μm of itself due to its convoluted architecture, scale bar=100 μm.

FIG. 39K shows a timeline of construction and maturation of the PT model.

FIGS. 40A-40D depict brightfield images of Cyclosporine A-induced cytotoxicity.

FIGS. 40E-40H depict 3D renderings of Cyclosporine A-induced cytotoxicity.

FIGS. 40I-40L sow high magnification images of printed and perfused 3D PTs dosed with varying concentrations of Cyclosporine A for 24 h, where actin (green) and nuclei (blue) are stained, scale bars=200 μm (a-h) and scale bars=20 μm (i-l), respectively.

FIG. 40M depicts a graph showing Diffusional permeability measurements taken after dosing with Cyclosporine A, *p<0.003, **p<0.02.

Figures 40A, 40N:
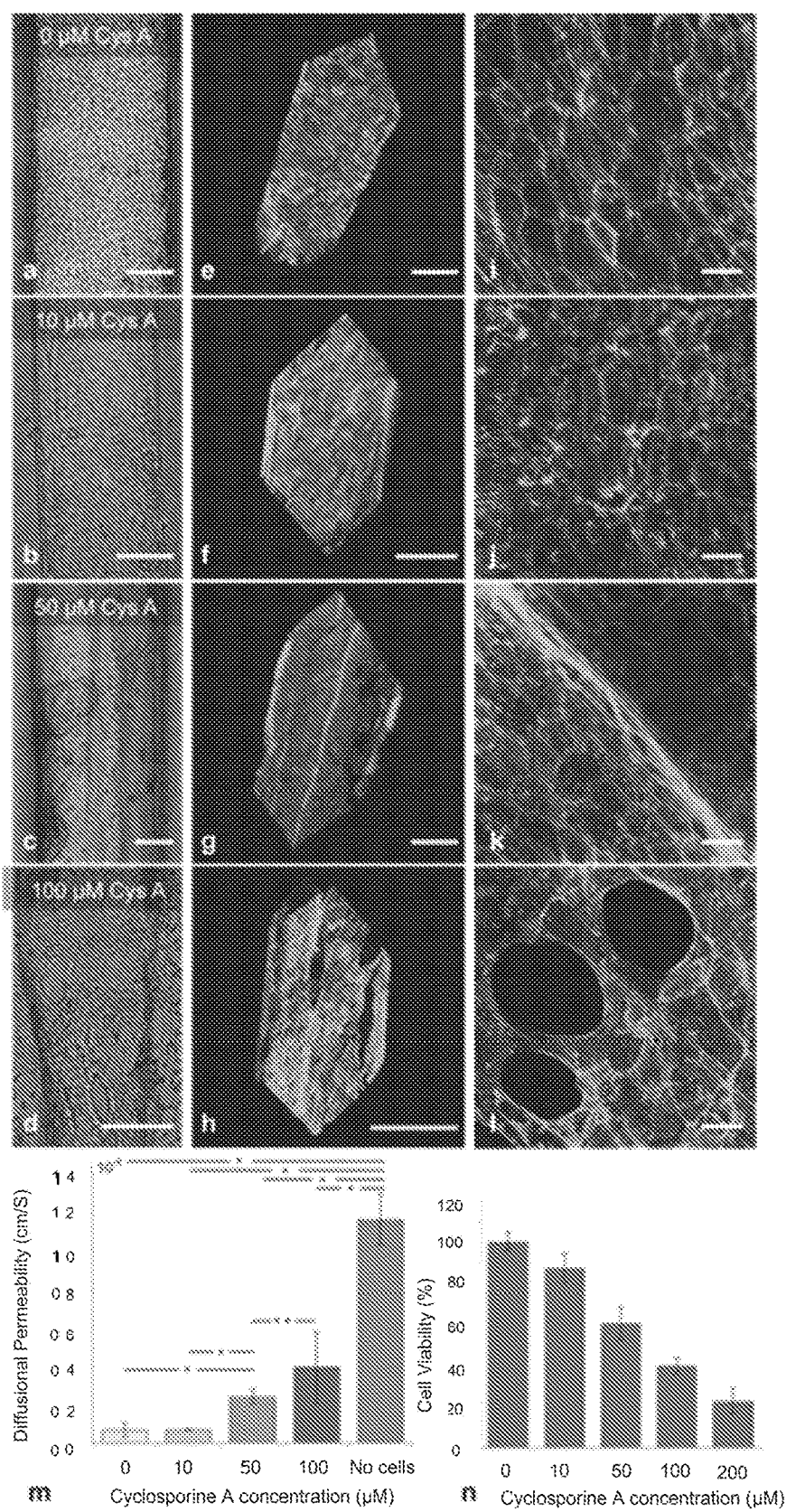

FIG. 40N depicts a graph showing cell viability measured for the 2D control (on bare dish) after dosing with Cyclosporine A (all populations shown are statistically significantly different with a p<0.005).

FIGS. 41A-41D depict fluorescent images captured at varying times: t=0 min (41A), t=45 min (41B), and t=0 min (41C) and 5 min (41D) (for control samples composed of a bare 3D PT (without PTECs), in which the FITC-labeled dextran diffuses much faster into the surrounding ECM) following perfusion with FITC-labeled dextran (70 kDa) solution through the 3D PT lined with confluent PTECs, scale bars=200 μm.

FIG. 41E depicts a bar graph showing measured diffusional permeability of 3D PT channels with and without proximal tubule epithelium.

Figure 42:
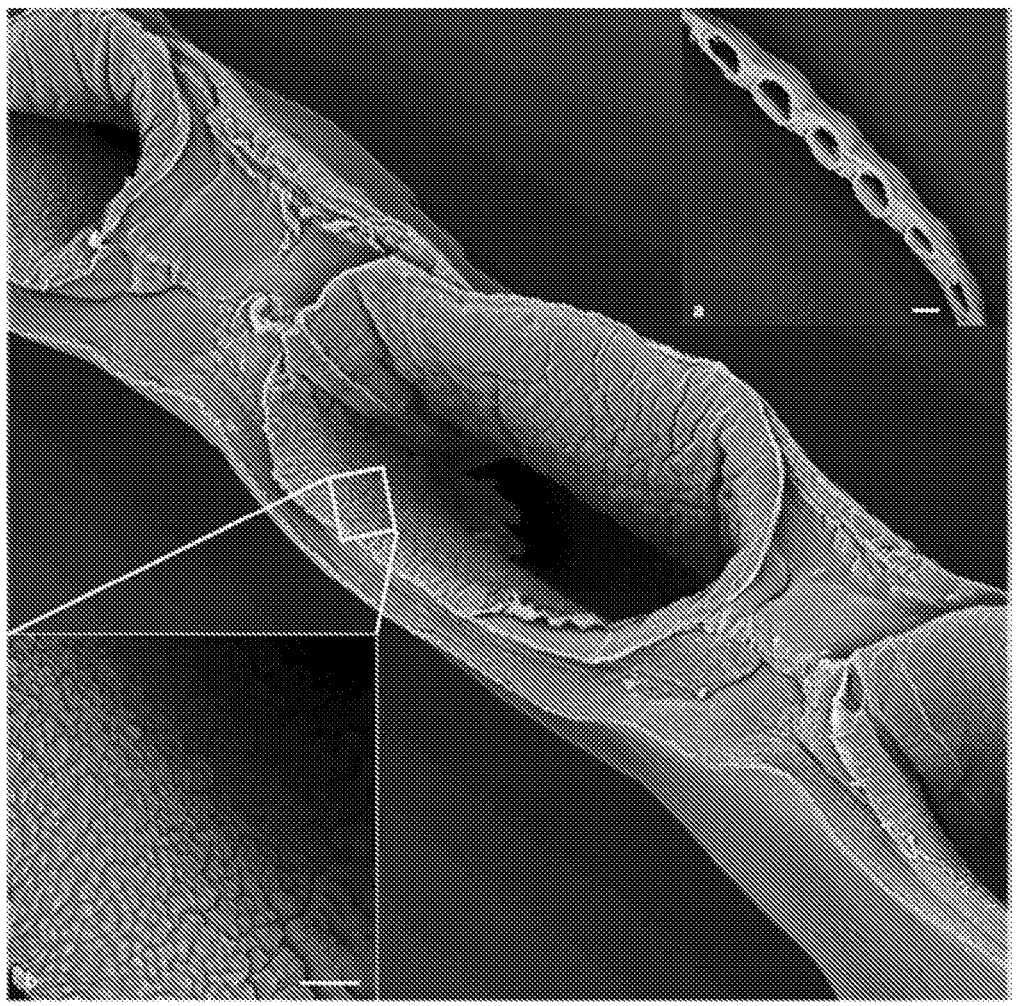

FIG. 42A depicts an SEM image of 6 PTs printed adjacent to one another (i.e., Multiplexed 3D proximal tubules), scale bar=500 μm.

FIG. 42B shows a high magnification image taken inside the larger 3D PT shown in the background, scale bar=50 μm.

Figures 43A, 43B:
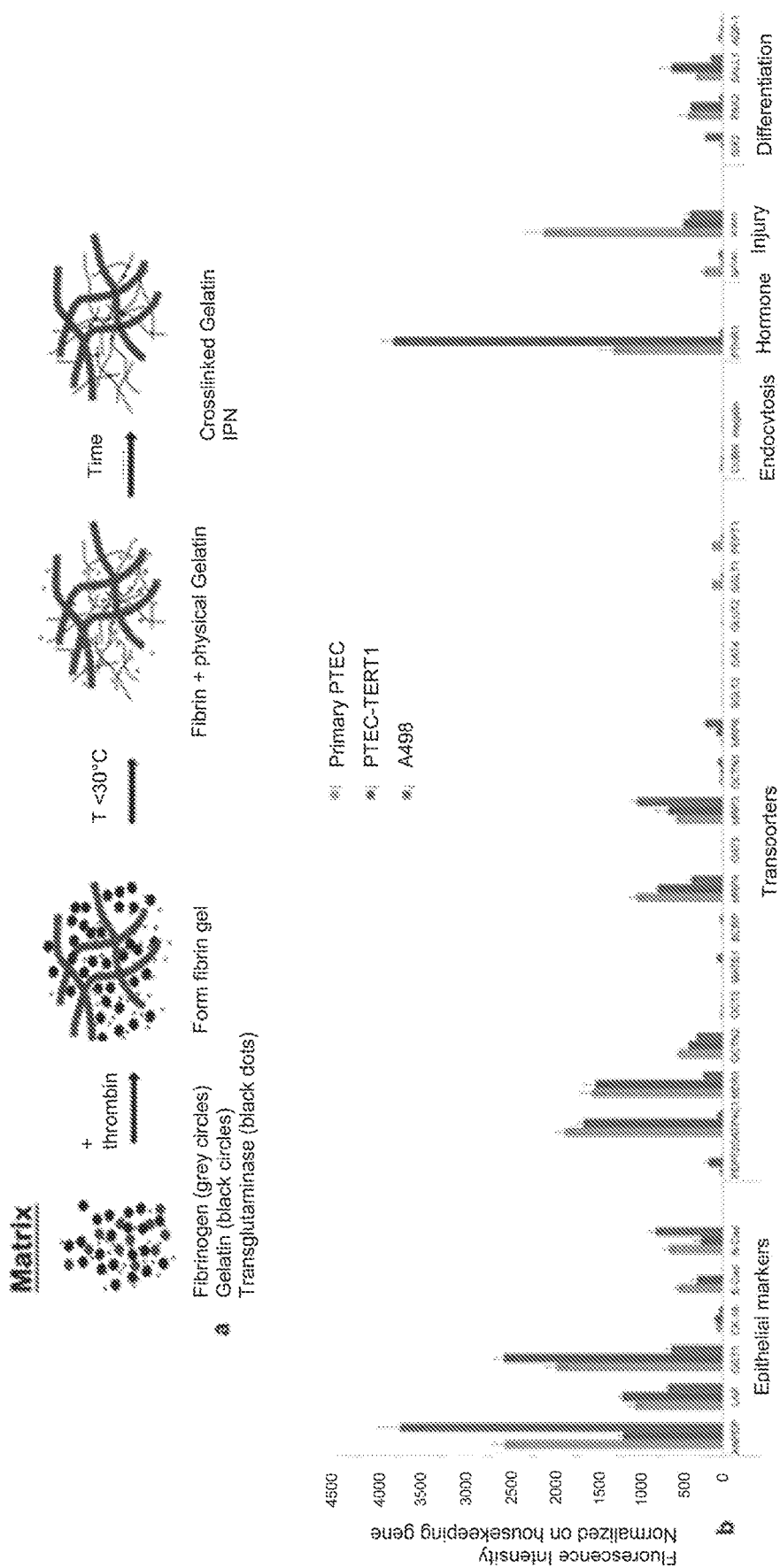

FIG. 43A depicts a Schematic representation of the ECM constituents and their gelation and cross-linking as a function of different stimuli.

FIG. 43B depicts relative mRNA levels of 33 selected genes related to renal epithelial function, transport, endocytosis, hormone response, injury response, and cell differentiation for three cell lines (primary renal PTEC, PTEC-TERTI, and the A498 cancer renal cell line). PTEC-TERTI cells are transcriptionally similar to primary PTEC and different from the A498 renal cancer epithelial cell line.

Figure 44A:
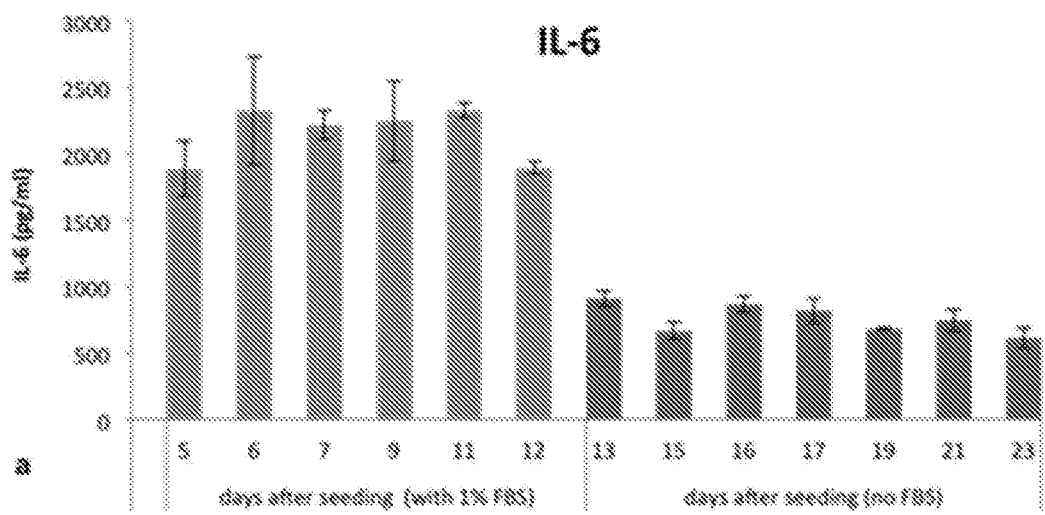
Figure 44B:
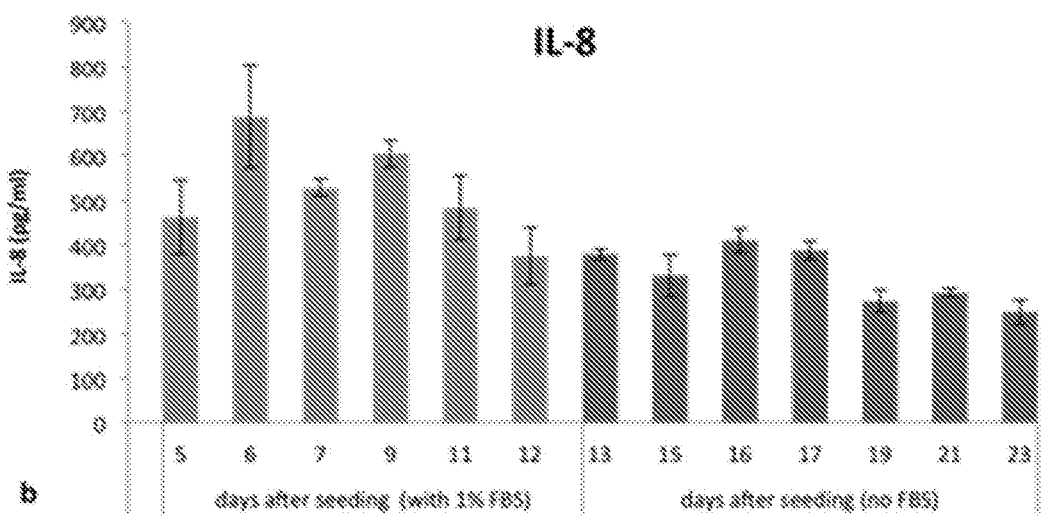
Figure 44C:
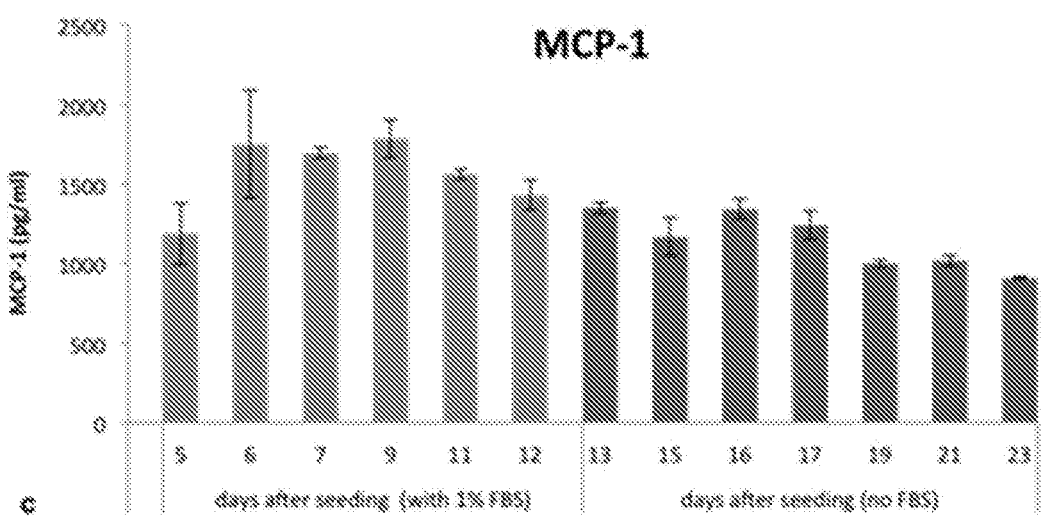

FIGS. 44A-44C depict bar graphs of the relative concentration of IL-6 (FIG. 44A), IL-8 (FIG. 44B), and MCP-I (FIG. 44C) following a 3D proximal tubule perfusate analysis.

Figures 45A, 45B, 45C, 45D, 45E, 45F, 45G, 45H, 45I, 45J, 45K:
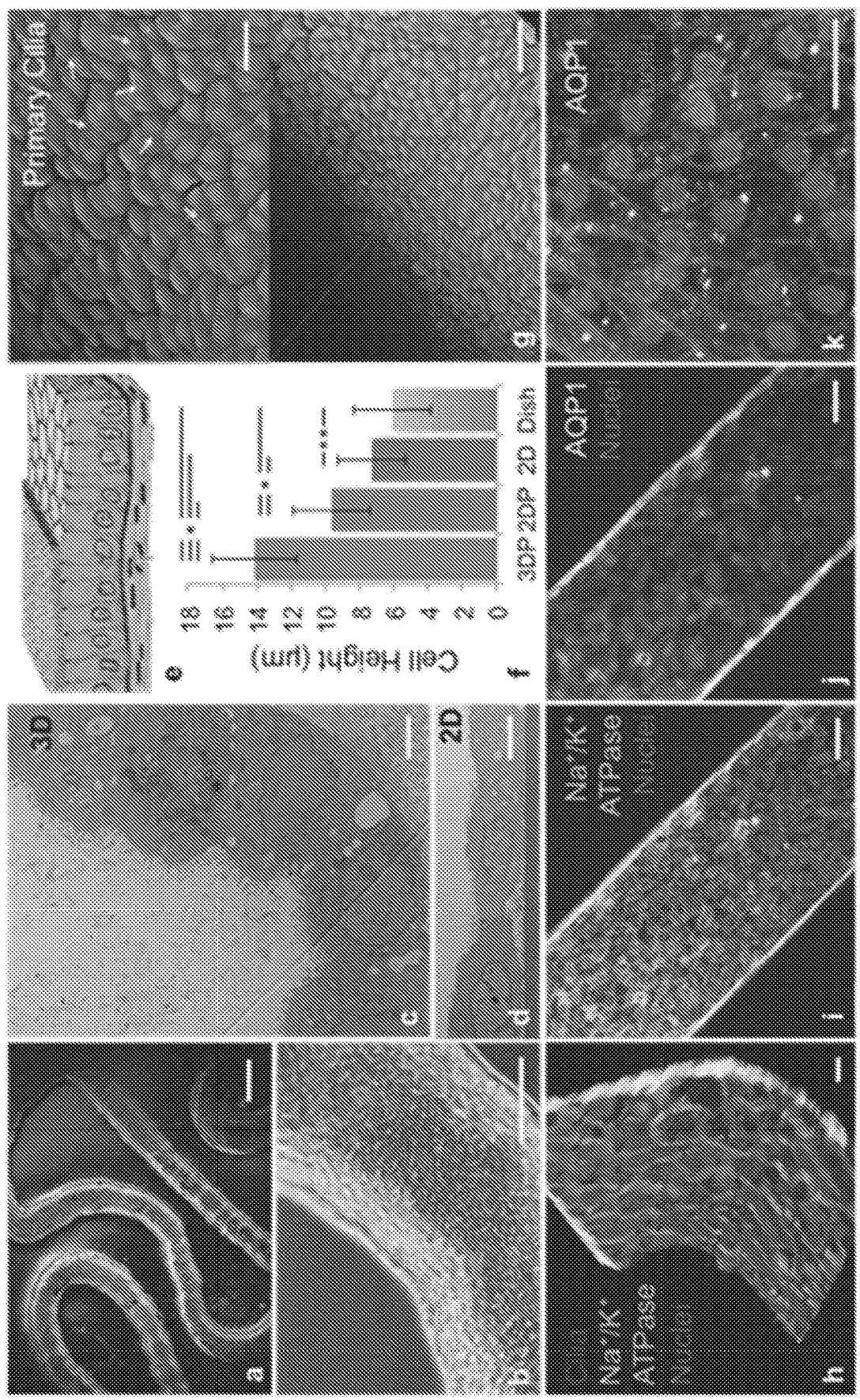

FIG. 45A depicts a phase contrast image of a mature 3D PT construct taken at 6 weeks, scale bar=500 μm.

FIG. 45B depicts a phase contrast image of the 3D PT construct at 6 weeks, scale bar=250 µm.

FIG. 45C depicts a TEM image of the PTECs within the tubule at 5 weeks, scale bar=5 µm.

FIG. 45D depicts a TEM image of the PTECs grown on a 2D dish coated with ECM with no perfusion, scale bar=5 µm.

FIG. 45E depicts a schematic view of the columnar epithelium seen in native tissue, in which PTECs pack together closely and exhibit a dense brush border on the apical side, tight junctions, and a solid basement membrane, reprinted with permission (Mescher, A. in Junqueira's Basic Histology: Text and Atlas, Edn. 13 85 (McGraw-Hill Education, 2013)).

FIG. 45F depicts a PTEC cell height as measured from TEM images of the 3D PT constructs (3DP) as well as three 2D controls (2DP=PTECs on ECM in 2D with perfusion, 2D=PTECs on ECM in 2D not perfused, Dish=bare tissue culture dish not perfused), *p<0.001, **p<0.02.

FIG. 45G depicts SEM images at low (scale bar=50 µm) and higher (scale bar=20 µm) magnifications showing a confluent layer of PTECs within the 3D PT, white arrows highlight the presence of primary cilia at a density of one per cell.

FIG. 45H depicts a 3D rendering of a partial tubule showing the apical side, which highlights the primary cilia (red), scale bar=20 µm.

FIG. 45I depicts an image of the PT highlighting the presence of Na/K ATPase in green, scale bar=100 µm.

FIG. 45J depicts an image of the 3D PT highlighting the presence of AQPI in yellow, scale bar=100 µm.

FIG. 45K depicts a high magnification view of the image in FIG. 25J highlighting actin in red and showing AQPI in yellow, scale bar=20 µm.

Figures 46A, 46B, 46C, 46D, 46E, 46F, 46G:
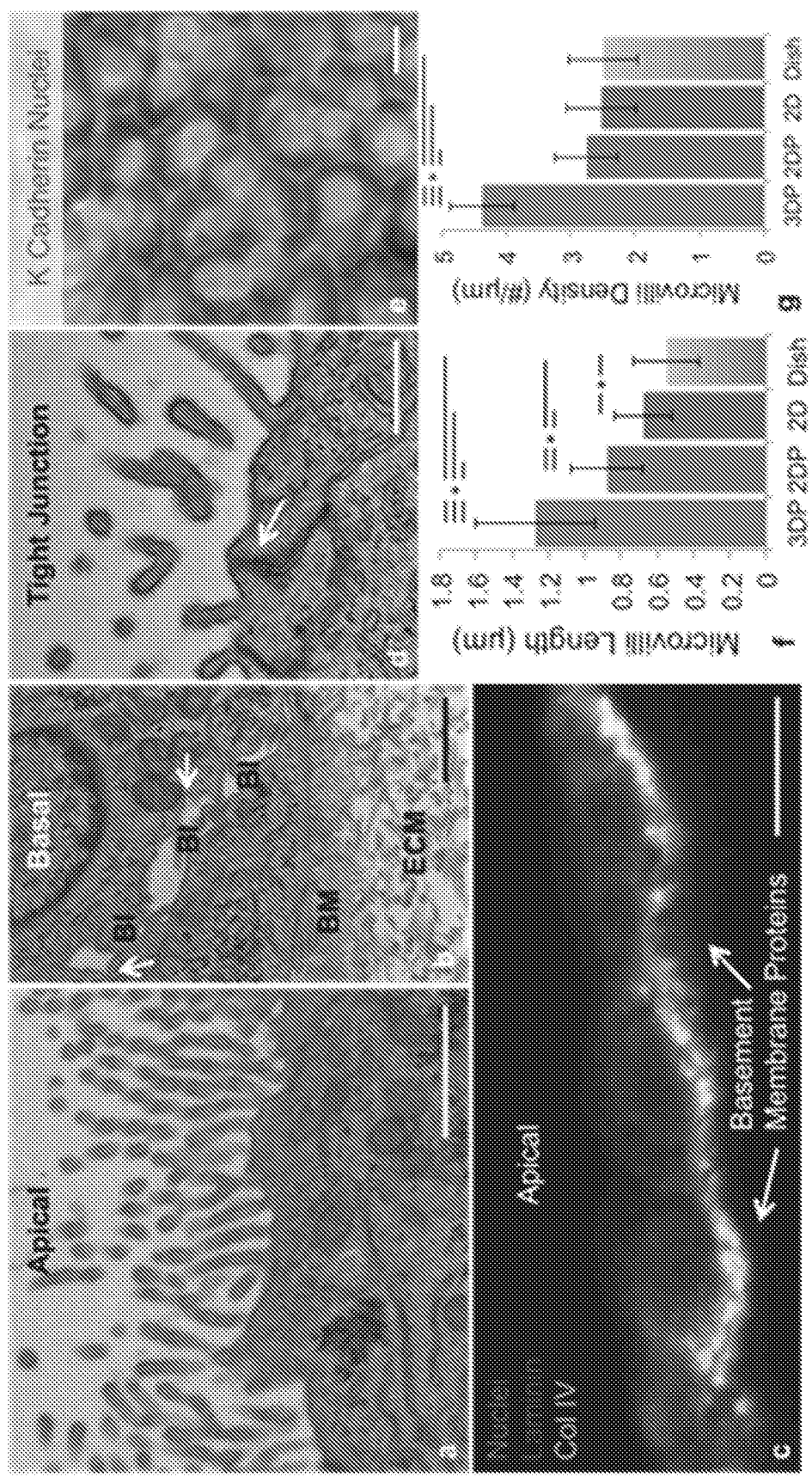

FIG. 46A depicts a TEM image of the brush border on the apical side of PTECs at 6 weeks, scale bar=1 µm.

FIG. 46B depicts a TEM image of the basal side of PTECs at 6 weeks highlighting the presence of the engineered extracellular matrix (ECM), basement membrane proteins secreted by the cells (BM), basolateral interdigitations (BI), and circular invaginations in the membrane marked with white arrows, scale bar=1 µm.

FIG. 46C depicts PTECs at 6 weeks showing the basement membrane proteins the cells secreted, namely laminin (predominant protein in red) and collagen IV (green), scale bar=10 µm.

FIG. 46D depicts a tight junction (white arrow) between PTECs in the bioprinted tubule, scale bar=500 nm.

FIG. 46E depicts the cell junction protein K Cadherin (magenta) stained in the PT, scale bar=10 µm.

FIGS. 46F and 46G depict a microvilli length (46F) and microvilli density (46G) quantified through TEM images of the 3D PT constructs (3DP) as well as three 2D controls (2DP=PTECs on ECM in 2D with perfusion, 2D=PTECs on ECM in 2D without perfusion, Dish=bare tissue culture dish without perfusion), p<0.001.

Figures 47A, 47B:
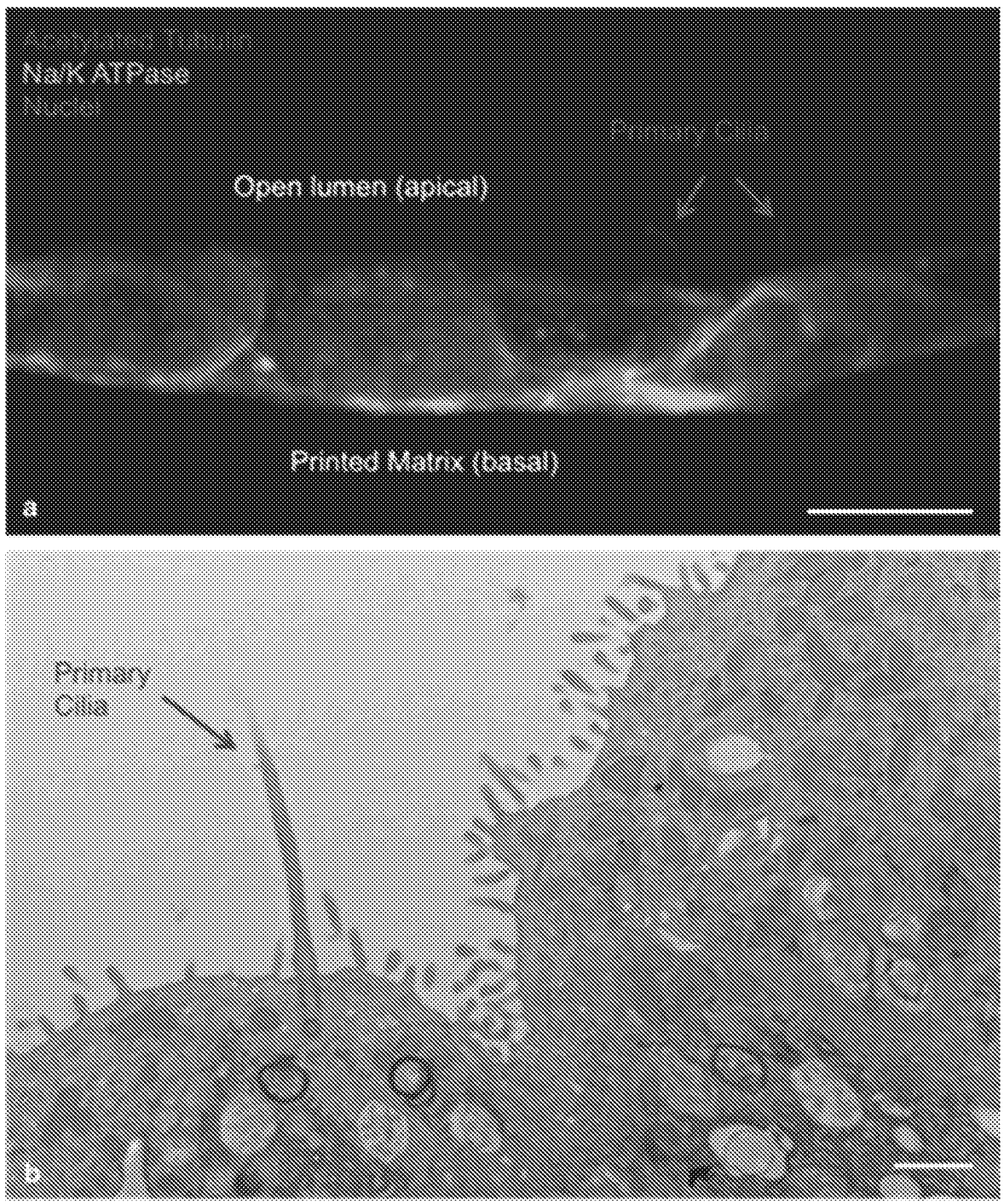

FIG. 47A depicts shows a 3D reconstruction of PTECs stained for Na$^+$/K$^+$ ATPase (green) and acetylated tubulin (red) where basal-lateral expression of Na$^+$/K$^+$ ATPase is apparent and two primary cilia are visible on the apical side, scale bar=10 µm.

FIG. 47B depicts a TEM image of primary cilia, scale bar=1 µm.

Figures 48A, 48B, 48C, 48D, 48E:
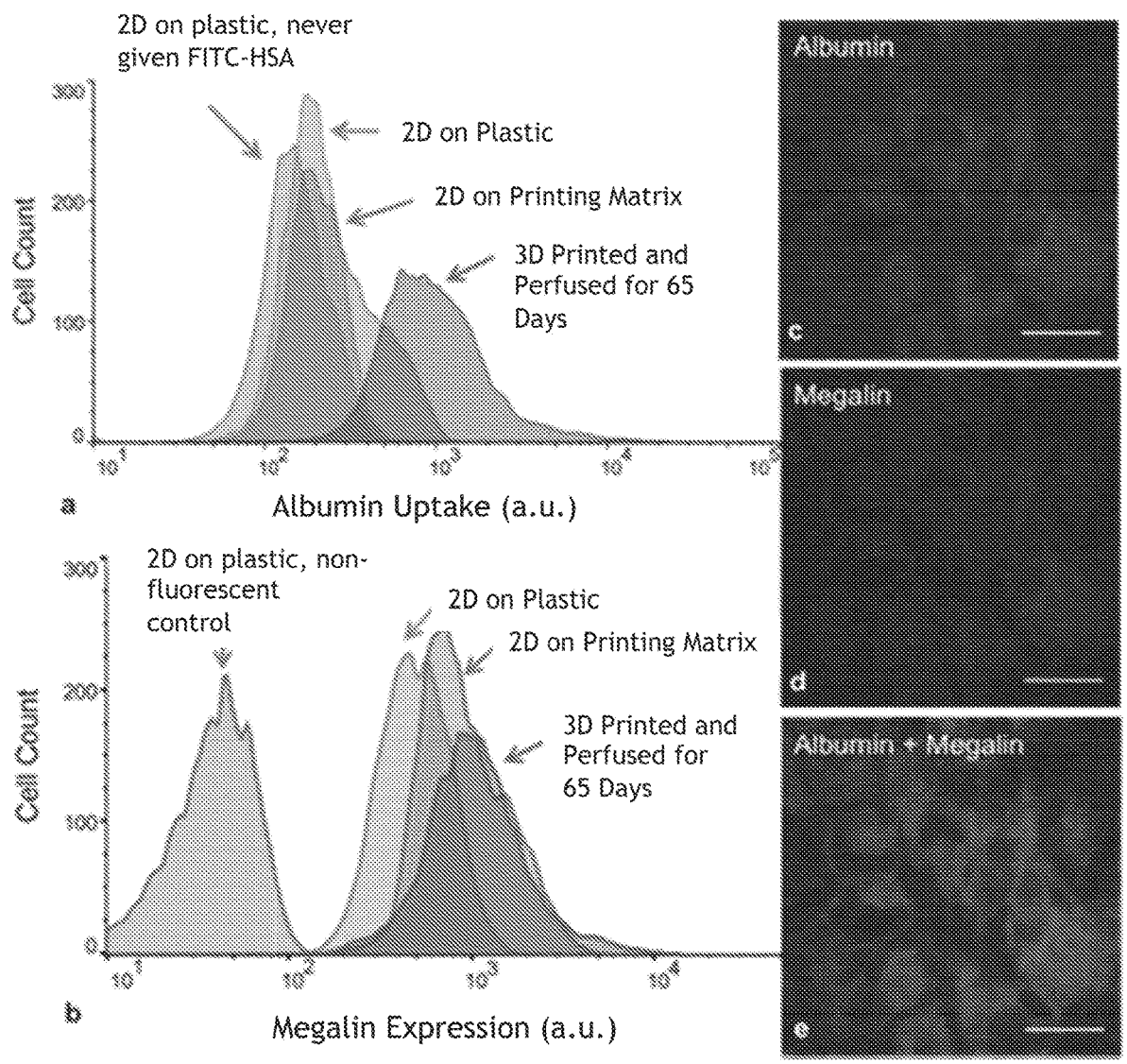

FIG. 48A is a graph showing the flow cytometry data comparing the fluorescence intensity of PTECs fed FITC-labeled human serum albumin for 2 h under several conditions, including 2D controls on bare (blue) and ECM-coated (green) plastic dishes and in 3D PTs perfused for 65 days (magenta).

FIG. 48B depicts a graph of the flow cytometry data comparing the fluorescence intensity of megalin for the same PTEC samples as shown in FIG. 48A.

FIG. 48C depicts a fluorescence image of the 3D PT constructs stained for FITC-labeled albumin (red), scale bars=20 µm.

FIG. 48D depicts a fluorescence image of the 3D PT constructs stained for FITC-labeled megalin (blue), scale bars=20 µm.

FIG. 48E depicts a fluorescence image of the 3D PT constructs stained for FITC-labeled albumin and FITC-labeled megalin (blue), scale bars=20 µm.

Figures 49A, 49B, 49C, 49D:
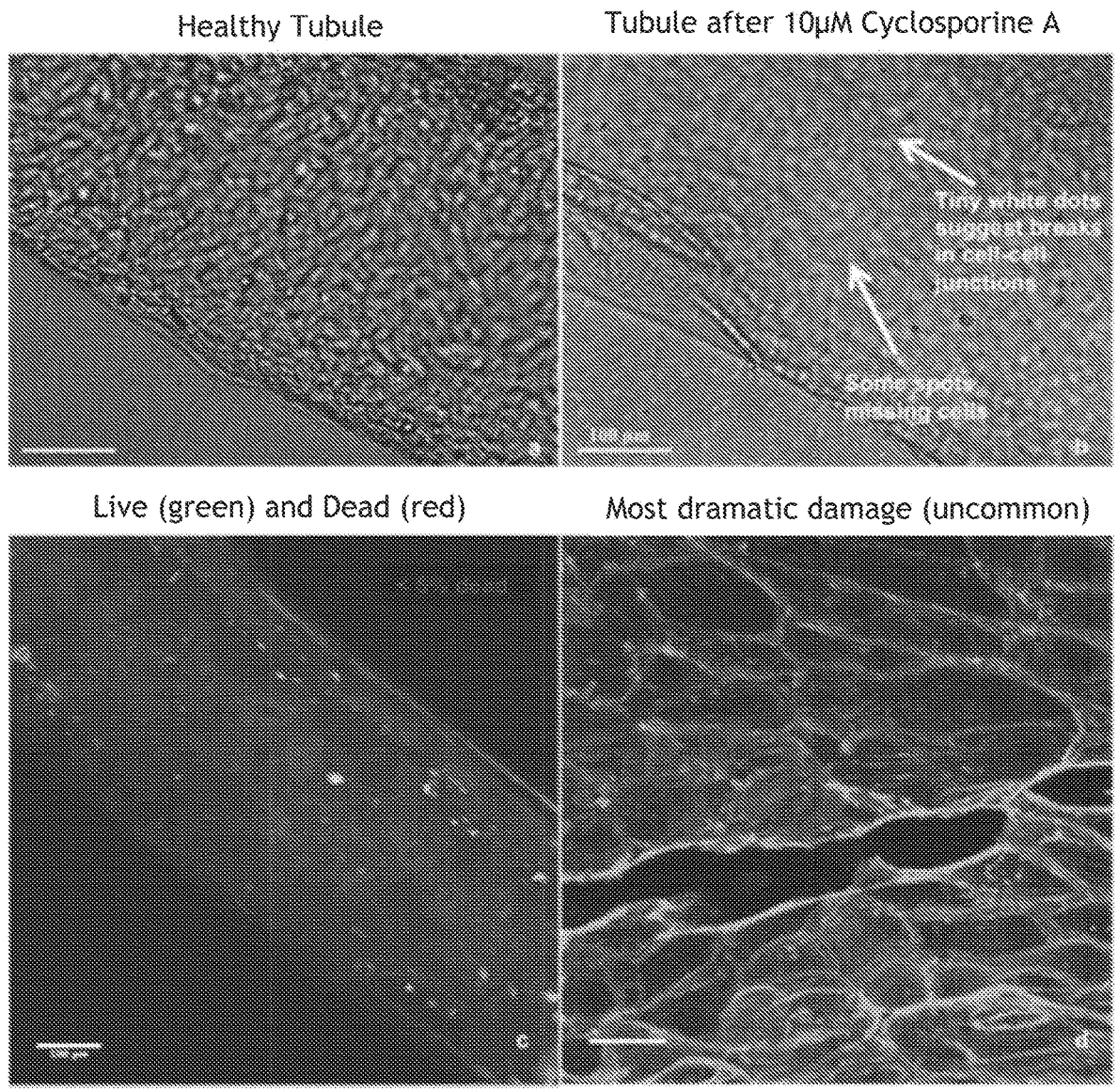

FIG. 49A depicts a brightfield image of a healthy proximal tubule at 4 weeks, scale bar=100 µm.

FIG. 49B depicts a brightfield image of a tubule after 24 h of cyclosporine A exposure, scale bar=100 µm.

FIG. 49C depicts an image showing live (green) and dead (red) staining of the tubule at 24 h after cyclosporine A exposure showing that <5% of the total cells are dead, scale bar=100 µm.

FIG. 49D depicts a high magnification image showing damage observed following dosing with with 10 µM cyclosporine A, where actin (green) and nuclei (blue) are stained, scale bar=20 µm.

DETAILED DESCRIPTION

Figure 1A:
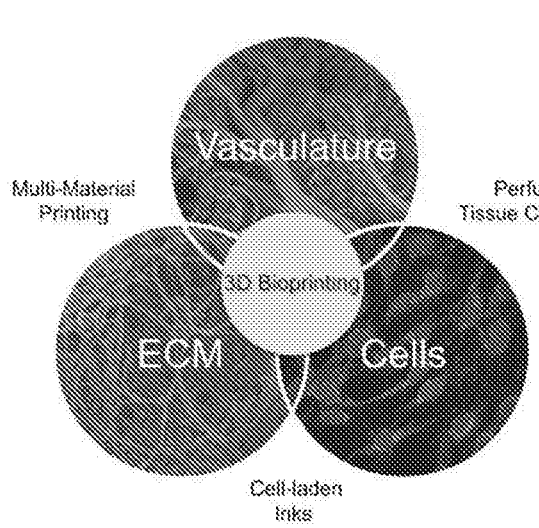
FIG. 1A shows an illustration of a bioprinting concept in which vasculature, an extracellular matrix, and cells may be printed in combination.
Figure 1B:
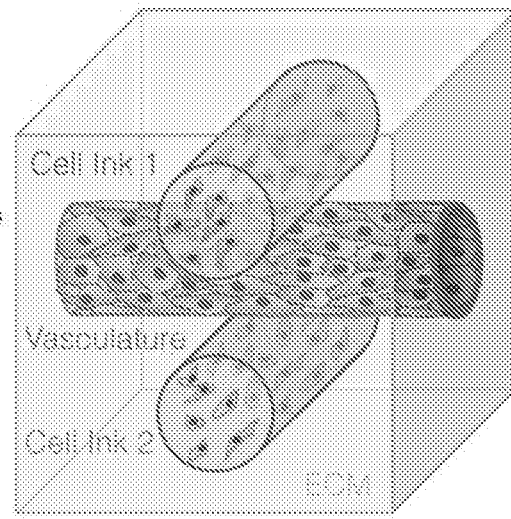
FIG. 1B shows a schematic of 3D printed heterogeneous tissue construct that includes vasculature and multiple cell types precisely placed in three dimensions.

A printed tissue construct including an interpenetrating vasculature and a method of printing such a tissue construct are described herein. FIG. 1A provides an illustration of the bioprinting concept. The printing method may enable the fabrication of heterogeneous 2D and 3D tissue constructs including cells, vasculature, epithelial ducts, and extracellular matrix in predetermined locations for applications ranging from 3D tissue culture and drug screen to organ transplants.

A printed tubular tissue construct, such as a nephron including at least two types of viable cells, each type of viable cells being positioned along a different predetermined location of the tubular tissue construct and methods of 3D printing such tubular tissue constructs are also described. FIGS. 23A-F provide illustrations of a nephron with the various types of cells along its length (A-E) as well as an illustration of an embedded nephron print (F). The constructs may be used, for example, in drug toxicology, whole organ printing, organ supplement, and/or dialysis replacement/supplement.

Figure 2A:
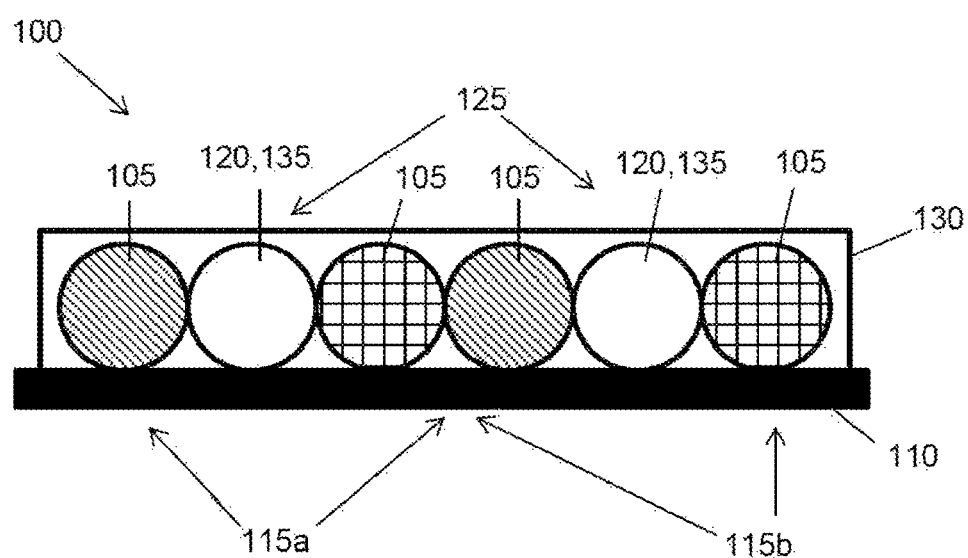
FIG. 2A is a cross-sectional schematic showing a 2D tissue construct including two tissue patterns and an interpenetrating vascular network.
Figure 2B:
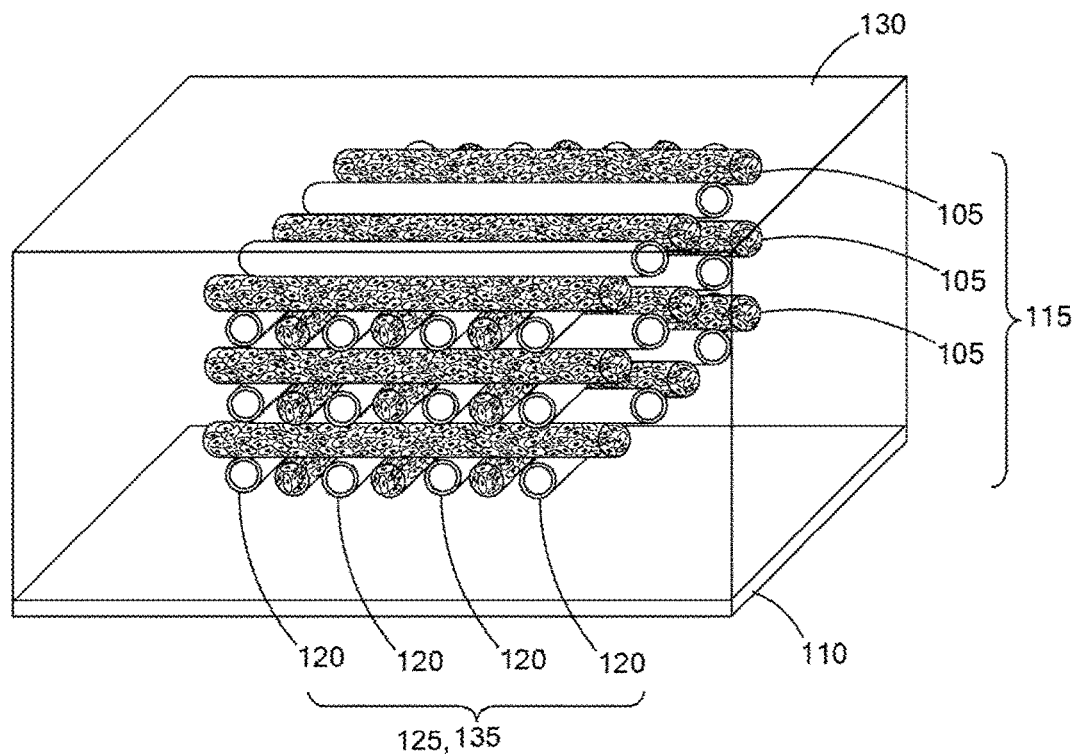
FIG. 2B shows an example of a 3D tissue construct including a tissue pattern and an interpenetrating vascular network.
Figure 2C:
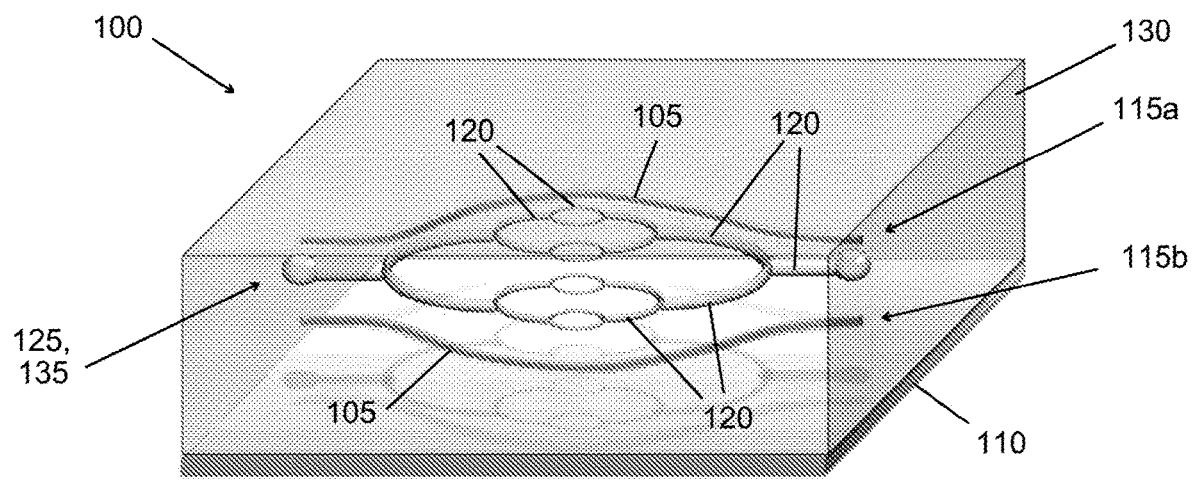
FIG. 2C shows an example of a 3D tissue construct including two tissue patterns and an interpenetrating vascular network.

FIG. 1B and FIGS. 2A-2C provide schematics showing exemplary printed tissue constructs that include vasculature and multiple cell types precisely placed in three dimensions. Referring to FIG. 2A or 2C, an exemplary printed tissue construct 100 comprises a first tissue pattern 115a and a second tissue pattern 115b, where each of the first and second tissue patterns 115a, 115b comprises a plurality of viable cells of one or more predetermined cell types. For example, the first tissue pattern 115a may include cell types A and B, and the second tissue pattern 115b may include cell type C. An arrangement of one or more cell-laden filaments 105 comprising the viable cells and having the predetermined cell types may define each tissue pattern 115a, 115b. In this example, the cell-laden filaments 105 that define the first tissue pattern 115a include cell types A and cell B, and the cell-laden filaments that define the second tissue pattern 115b include cell type C. A network of vascular channels 135 interpenetrates the tissue patterns 115a, 115b. An extracellular matrix composition 130 at least partially surrounds the one or more tissue patterns 115a, 115b and the network of vascular channels 135.

A pattern or network that "interpenetrates" another pattern or network in a printed tissue construct may be understood to comprise one or more filaments, channels or portions that are layered with, partially or completely overlapping, partially or completely underlapping, surrounding, embedded within, and/or interwoven with one or more filaments, channels or portions of the other pattern or network. A filament "deposited on a substrate" may be understood to be deposited directly on the substrate, directly in the substrate, or directly on another filament, channel or portion previously deposited or formed on the substrate.

Referring now to FIG. 2B, a tissue construct comprising an embedded vasculature may be printed by depositing one or more cell-laden filaments 105, where each cell-laden filament 105 comprises a plurality of viable cells, on a substrate 110 to form one or more tissue patterns 115 (one tissue pattern in this example). The tissue pattern 115 comprises cells of one or more predetermined cell types. One or more sacrificial filaments 120, each comprising a fugitive ink, are also deposited on the substrate 110 to form a vascular pattern 125 that interpenetrates the one or more tissue patterns 115. The one or more tissue patterns 115 and the vascular pattern 125 are partially or fully surrounded by an extracellular matrix composition 130. The fugitive ink is then removed to create a network of vascular channels 135 in the extracellular matrix composition 130. Thus, an interpenetrating vascular network is formed in the tissue construct 100.

The tissue construct may include up to n different predetermined cell types. For example, n may satisfy $1 \leq n \leq 300$, $2 \leq n \leq 200$, or $2 \leq n \leq 100$. More typically, n is no more than 50, no more than 30, or no more than 20. For example, there may be 2 or more, 4 or more, 8 or more, 16 or more, or 20 or more predetermined cell types in the tissue construct. Further, one cell type may be printed, such as a multi- or pluripotent stem cells, of any origin, that could turn into 20 or more cells types as directed by either perfusion, matrix cues, or perfused growth factors, small molecules, or other agents.

As illustrated by the examples of FIGS. 2A-2C, each tissue pattern comprises or is defined by a two- or three-dimensional arrangement of one or more cell-laden filaments, and each tissue pattern (and thus each arrangement of cell-laden filaments) may comprise a different subset of the predetermined cell types. For example, in a tissue construct that includes 5 different predetermined cell types (e.g., cell types A, B, C, D, and E) and 3 different tissue patterns (e.g., tissue patterns 1, 2, and 3), tissue pattern 1, which is defined by a first arrangement of one or more cell-laden filaments, may comprise cell type A; tissue pattern 2, which is defined by a second arrangement of one or more cell-laden filaments, may comprise cell types B and C; and tissue pattern 3, which is defined by a third arrangement of one or more cell-laden filaments, may comprise cell types A and E.

In addition to the viable cells, the one or more cell-laden filaments may comprise a synthetic or naturally-derived biocompatible material that may be referred to as an extracellular matrix material. Each of the one or more cell-laden filaments may also or alternatively comprise one or more functional chemical substances (e.g., drugs, toxins, proteins and/or hormones) as described below. Each tissue pattern may include one layer or multiple layers of the cell-laden filament(s), which may in some embodiments be at least partially coalesced at regions of contact therebetween. For example, adjacent layers formed from one or more cell-laden filaments may be partially or fully coalesced depending on filament composition and the deposition (or post-deposition) conditions.

The arrangement of the cell-laden filaments in the tissue construct may be continuous or discontinuous. In a continuous arrangement, the cell-laden filaments of an exemplary tissue pattern (and comprising one or more predetermined cell types) may form a single interconnected tissue network in the tissue construct. For example, a single cell-laden filament comprising viable cells of the predetermined cell type(s) may be deposited in a single layer or in multiple layers to form the continuous arrangement. Alternatively, a plurality of cell-laden filaments comprising viable cells of the predetermined cell type(s) may be deposited in a single layer or in multiple layers to form the continuous arrangement, where each of the cell-laden filaments is in physical contact with, and possibly at least partially coalesced with, another cell-laden filament comprising the same predetermined cell type(s).

In a discontinuous arrangement of cell-laden filaments comprising one or more predetermined cell types, a single interconnected tissue network of the predetermined cell type(s) is not formed within the tissue construct. Instead, the cell-laden filaments comprising the predetermined cell type(s) may be dispersed uniformly or nonuniformly throughout the tissue construct. Consequently, the cells corresponding to the predetermined cell type(s) may also be dispersed uniformly or nonuniformly (e.g., in clumps) throughout the tissue construct. In this embodiment, some, all or none of the cell-laden filaments of a given tissue pattern and cell type(s) may be in physical contact with another cell-laden filament comprising cells of the same cell type(s).

Each of the one or more cell-laden filaments includes at least one viable cell and may include a large number of viable cells. For example, each of the cell-laden filaments may have a cell concentration of at least about 100 cells/ml, at least about 1000 cells/ml, at least about $10^4$ cells/ml, at least about $10^5$ cells/ml, at least about $10^6$ cells/ml, at least about $10^7$ cells/ml, or at least about $10^8$ cells/ml. Typically, the cell concentration is no higher than about $10^9$ cells/ml, or no higher than about $10^8$ cells/ml. Consistent with this, the one or more tissue patterns of the tissue construct may have a cell concentration of at least about 100 cells/ml, at least about 1000 cells/ml, at least about $10^4$ cells/ml, at least about $10^5$ cells/ml, at least about $10^6$ cells/ml, at least about $10^7$ cells/ml, or at least about $10^8$ cells/ml. Typically, the cell concentration in the tissue pattern is no higher than about $10^9$ cells/ml, or no higher than about $10^8$ cells/ml.

The cell concentration may be substantially uniform (e.g., within ±10%, within ±5%, or within ±1%) throughout each of the cell-laden filaments, and the cell concentration may also be substantially uniform throughout each of the tissue pattern(s). Alternatively, it is possible to deposit cell-laden filaments that include aggregates or clusters of cells that may range in size from about 10 cells/cluster to about 1000 cells/cluster, or from about 10 cells/cluster to about 100 cells/cluster. Such clusters may be dispersed uniformly or non-uniformly within the cell-laden filaments (and thus uniformly or non-uniformly throughout the one or more tissue patterns). Overall, the cell concentration may be substantially uniform throughout the tissue construct, or the cell concentration may include predetermined inhomogeneities within the tissue construct that may be defined by the location and morphology of the one or more tissue patterns, and/or by the cell distribution within the one or more tissue patterns.

The vascular network that interpenetrates the one or more tissue patterns is a two- or three-dimensional interconnected arrangement of vascular channels. The network may include one or more-furcations (e.g., bifurcations, trifurcations, etc.) from a parent vascular channel to a plurality of branching vascular channels. The network may have a hierarchical branching structure, where larger diameter channels branch into smaller diameter channels. Some or all of the vascular channels may follow a curved path, and thus may be considered to be curvilinear. All of the vascular channels in the network may have the same diameter, or at least one, some, or all of the vascular channels may have a different diameter. In some cases, one or more of the vascular channels may have a nonuniform diameter along a length thereof.

It is beneficial for the cells of the tissue construct to be close enough to the interpenetrating network of vascular channels to remain viable. One major problem with previous attempts to create tissue and organ-like structures is that necrotic regions could develop in areas without accessible perfusable vasculature. In the present work, each cell-laden filament, and thus each cell, may be placed in a location near to the vascular network, or near to where the vascular network may be formed. For example, at least a portion of the one or more cell-laden filaments forming each tissue pattern, and thus some or all of the viable cells, may be no more than about 1 mm away, no more than about 500 microns away, no more than about 300 microns away, no more than about 200 microns away, no more than about 100 microns away, no more than about 50 microns away, and/or no more than about 10 microns away from a vascular channel. One or more of the cell-laden filaments and thus at least some of the viable cells may be deposited so as to be in direct contact with a vascular channel. It is envisioned that some portion of the vascular network, for example the smallest capillaries, may be formed by angiogenesis and/or tubulogenesis after deposition of the sacrificial filaments and removal of the fugitive ink. For example, cell-laden filaments comprising endothelial cells may be deposited adjacent to the fugitive network to encourage tubulogenesis and/or angiogenesis to generate new capillaries.

Because the printing process described below for deposition of the cell-laden (and other) filaments allows for a high positional accuracy, the placement of the viable cells and/or the extracellular matrix material within the tissue construct may be controlled to within ±200 microns, within ±100 microns, within ±50 microns, within ±10 microns, or within ±1 micron.

Different types of cells may be placed in close proximity to one another by depositing a cell-laden filament that includes cells of more than one cell type, as discussed above. It is also contemplated that, in addition to the interpenetrating vasculature, one or more of the tissue patterns may interpenetrate one or more of the other tissue patterns so that certain types of cells may be positioned in close proximity to another. For example, one or more cell-laden filaments comprising a first type of cells (e.g., epithelial or endothelial cells) may be layered with, partially or completely overlapping, partially or completely underlapping, surrounding, embedded within, and/or interwoven with one or more cell-laden filaments comprising a second type of cells (e.g., smooth muscle cells). In some embodiments, all of the tissue patterns may interpenetrate at least one other tissue pattern, and it is also contemplated that all of the tissue patterns may interpenetrate all of the other tissue patterns.

The extracellular matrix composition may partially or fully surround the one or more tissue patterns, where a tissue pattern that is fully surrounded includes no exposed cell-laden filaments. The extracellular matrix composition may also partially or fully surround the network of vascular channels, where a vascular network that is fully surrounded includes no exposed vascular channels. For example, the network of vascular channels may be fully surrounded by the extracellular matrix composition, while the tissue pattern may be only partially surrounded by (e.g., adjacent to) the extracellular matrix composition. In such an example, the cell-laden filaments may be deposited after the vascular pattern is encapsulated. In some embodiments, the extracellular matrix composition may comprise additional viable cells and/or one or more functional chemical substances, as described below, which may be deposited along with the extracellular matrix composition. Such an extracellular matrix composition may be referred to as a cell-laden matrix. As described below, the extracellular matrix composition may be printed, cast or formed by another method known to one of ordinary skill in the art.

The tissue construct may have any desired 2D or 3D shape. For example, the tissue construct may have a planar geometry constructed from a single layer or multiple layers of cell-laden filaments and an interpenetrating vascular network. Such structures may have any desired height ("thickness"). Typically, the tissue construct has a height of about 100 cm or less, about 10 cm or less, about 1 cm or less, about 1 mm or less, about 500 microns or less, or about 100 microns or less, and typically at least about 10 microns, at least about 100 microns, at least about 200 microns, or at least about 1 mm, with applications ranging from tissue cultures and drug screening to skin constructs and corneal replacements. In certain alternative embodiments, the tissue construct may have thickness of at least 1 cm and, preferably, exceed the thickness of 1 cm. The term "thick" in reference to a tissue construct means thicker than 1 mm.

Alternatively, the tissue construct into which a vascular network is embedded may have an arbitrary or application-dependent 3D size and shape. The tissue construct may have a solid structure, a porous structure, and/or a hollow structure (e.g., tubular or nontubular) and may be fabricated to mimic the morphology and function of particular organ. For example, the tissue construct may have the size and shape of a kidney, heart, pancreas, liver, bladder, vagina, urethra, trachea, esophagus, skin or other bodily organ. The 3D size and shape may in some cases be determined by a mold, as described below.

In general, in a three-dimensional arrangement of cell-laden filaments with an interpenetrating vascular pattern, the sacrificial filaments may have portions that overlie or underlie portions of the cell-laden filaments, and the sacrificial and cell-laden filaments may or may not be confined to an XY plane normal to the vertical direction (as defined by the force of gravity). The sacrificial filaments may be in physical contact with some or all of the cell-laden filaments, and, in some embodiments, the filaments may be partially or fully coalesced at the regions of contact. Both the sacrificial and cell-laden filaments may have spanning portions that extend unsupported between points of contact.

FIGS. 2A-2C show exemplary tissue constructs 100 each comprising one or more tissue patterns 115 interpenetrated by a vascular pattern 125 or a network of vascular channels 135. In FIG. 2A, two tissue patterns 115a, 115b each comprising two cell-laden filaments 105 are deposited on the substrate 110 in a single layer. Adjacent to and/or in physical contact with the cell-laden filaments 105 are sacrificial filaments 120 of the vascular pattern 125, where each sacrificial filament 120 comprises a fugitive ink. After encapsulation with the extracellular matrix composition 130, the fugitive ink may be removed to form the network of vascular channels 135.

FIG. 2B shows a schematic of a tissue construct 100 comprising a 3D lattice structure 115 of cell-laden filaments 105 alternating with sacrificial filaments 120 of an interpenetrating vascular pattern 125. The fugitive ink making up the sacrificial filaments 120 is ultimately removed to create the network of vascular channels 135, which may also be visualized in FIG. 2B.

The tissue construct 100 of FIG. 2C includes two tissue patterns 115a, 115b each defined by a curvilinear cell-laden filament 105 that are interpenetrated by a network of vascular channels 135 (or by a vascular pattern 125 comprising sacrificial filaments 120 if the fugitive ink has not yet been removed). The vascular network 135 has a hierarchical branching structure including curvilinear channels of various lengths and diameters. A solid substrate 110 is shown underlying the tissue construct 100; however, in this and in the other exemplary figures, the underlying solid substrate 110 may not be present.

Figure 3A:
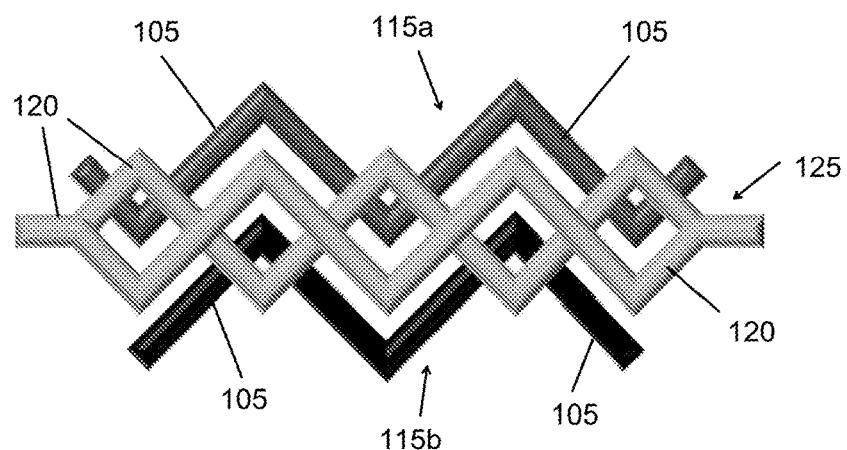
FIGS. 3A and 3B show examples of 3D tissue constructs including two tissue patterns and an interpenetrating vascular network.
Figure 3B:
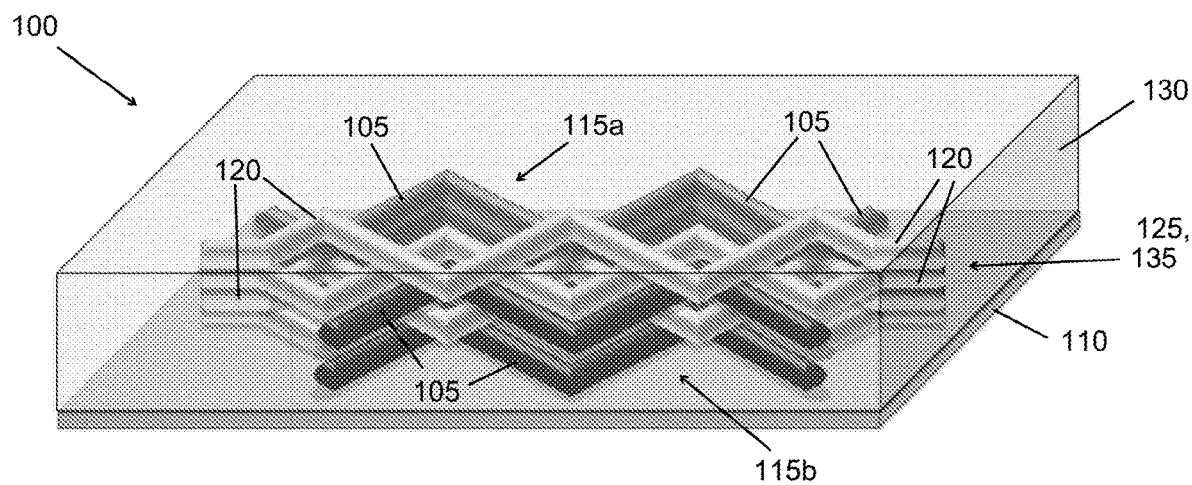

FIG. 3A shows a top view of two exemplary tissue patterns 115a, 115b comprising cell-laden filaments 105 in a semi-woven configuration with sacrificial filaments 120 of a vascular pattern 125. FIG. 3B shows multiple layers of the same tissue patterns 115a, 115b and vascular pattern 125 (or network of vascular channels 135 if the fugitive ink has been removed) surrounded by an extracellular matrix composition 130.

The viable cells and the predetermined cell types in the tissue construct may include any mammalian cell type selected from cells that make up the mammalian body, including germ cells, somatic cells, and stem cells. Depending on the type of cell, cells that make up the mammalian body can be derived from one of the three primary germ cell layers in the very early embryo: endoderm, ectoderm or mesoderm. The term "germ cells" refers to any line of cells that give rise to gametes (eggs and sperm). The term "somatic cells" refers to any biological cells forming the body of a multicellular organism; any cell other than a gamete, germ cell, gametocyte or undifferentiated stem cell. For example, in mammals, somatic cells make up all the internal organs, skin, bones, blood and connective tissue. As such, a cell may include any somatic cell isolated from mammalian tissue, including organs, skin, bones, blood and connective tissue (i.e., stromal cells). Examples of somatic cells include fibroblasts, chondrocytes, osteoblasts, tendon cells, mast cells, wandering cells, immune cells, pericytes, inflammatory cells, endothelial cells, myocytes (cardiac, skeletal and smooth muscle cells), adipocytes (i.e., lipocytes or fat cells), parenchyma cells (neurons and glial cells, nephron cells (i.e., renal proximal tubule cells, loop of Henle cells, renal distal tubule cells, collecting duct cells, and fenestrated glomerular endothelial cells (i.e., podocytes)), hepatocytes, pancreatic cells, lung parenchyma cells) and non-parenchymal cells (e.g., sinusoidal hepatic endothelial cells, Kupffer cells and hepatic stellate cells). The term "stem cells" refers to cells that have the ability to divide for indefinite periods and to give rise to virtually all of the tissues of the mammalian body, including specialized cells. The stem cells include pluripotent cells, which upon undergoing further specialization become multipotent progenitor cells that can give rise to functional or somatic cells.

Examples of stem and progenitor cells include hematopoietic stem cells (adult stem cells; i.e., hemocytoblasts) from the bone marrow that give rise to red blood cells, white blood cells, and platelets; mesenchymal stem cells (adult stem cells) from the bone marrow that give rise to stromal cells, fat cells, and types of bone cells; epithelial stem cells (progenitor cells) that give rise to the various types of skin cells; neural stem cells and neural progenitor cells that give rise to neuronal and glial cells; and muscle satellite cells (progenitor cells) that contribute to differentiated muscle tissue.

In some embodiments, induced pluripotent stem cells (iPSCs) may be used to as starting materials to derive patient-specific predetermined cell types for use in the tissue construct development. iPSCs are a type of pluripotent stem cell that can be generated directly from adult cells, self-renew indefinitely and have unlimited developmental potential. For example, iPSCs can be used to derive patient-specific pro-kidney or individual cell lines present in a nephron (e.g., renal proximal tubule cells, loop of Henle cells, renal distal tubule cells, collecting duct cells, and fenestrated glomerular endothelial cells (i.e., podocytes)).

The tissue construct may also include one or more functional chemical substances selected from among drugs, toxins, proteins and/or hormones, including, but not limited to: growth factors, growth inhibitors, cytokines, steroids, and/or morphogens. Some cell specific examples include: bone morphogenic protein, vascular endothelial growth factor, fibroblast growth factors, including but not limited to VEGF, EGF, TGF-beta. The one or more functional chemical substances may be deposited with the cell-laden filament(s) and/or the sacrificial filaments and may diffuse into the surrounding extracellular matrix composition.

Such an approach may be used to generate gradients of cues within the extracellular matrix composition. Cells respond to gradients of fixed and diffusible chemical cues during development, wound healing and inflammatory responses that can direct cell migration, proliferation and differentiation. One method to introduce gradients of cues is to directly print cell-laden filaments preloaded with cues of interest, as illustrated in FIGS. 12A-12C, which may diffuse out upon encapsulation with an extracellular matrix composition to generate concentration gradients. Such gradients may or may not be anchored to the scaffold by action of transglutaminase. Alternatively, to generate fixed, long-term gradients, the channels formed by removing fugitive ink can be used to introduce factors that may diffuse into the surrounding extracellular matrix composition. For example, the formation of a linear gradient of fluorescently labeled BSA is demonstrated in FIGS. 12D-12F by creating a pair of parallel channels and flowing the fluorescent BSA through only one channel. At 24 hours, a near-linear gradient is apparent between the two channels (FIGS. 12E-12F).

The extracellular matrix material of the cell-laden filaments and the extracellular matrix composition that at least partially surrounds the tissue and vascular patterns may comprise a synthetic or naturally derived biocompatible material. The extracellular matrix material and the extracellular matrix composition may comprise the same or different biocompatible materials. Because the cell-laden filaments and, in some embodiments, the extracellular matrix composition may be deposited in a 3D printing process that entails extrusion through a micronozzle, as described below, it may be beneficial for one or both of the extracellular matrix material and the extracellular matrix composition to: (1) exhibit shear thinning behavior; (2) exhibit a defined yield stress $\tau_y$; and/or (3) have a shear elastic modulus G' and a shear viscous modulus G" modulus where G'>G" at room temperature.

In one example, the extracellular matrix material and/or the extracellular matrix composition may comprise a gel. An ideal gel for bioprinting applications may exhibit a rapid transition from a low viscosity solution to a solid-like gel, which may be seen by an initial increase in shear elastic modulus. Rapid, controllable gelation may enhance printed structure fidelity by minimizing or obviating swelling and dissociation typical of slow gelation processes. The term "gel" may refer to a semi-solid substance that may comprise a gelling agent to provide viscosity or stiffness. The gel may be formed upon use of a gelling agent, such as a thickening agent, crosslinking agent or a polymerization agent, and may comprise a cross-linked structure or a non-cross-linked structure. The gel may be hydrophobic or hydrophilic. Some examples of suitable gels include a hydrogel, thermo-reversible gel, a photo-sensitive gel, a pH sensitive gel, a peptide gel, or a cell type specific gel. Additional examples of gels include silica gel, silicone gel, aloe vera gel, agarose gel, nafion, polyurethane, elastomers (thermoplastic, mineral-oil thermoplastic, etc.), ion-exchange beads, organogels, xerogels and hydrocolloids. Hydrogels include those derived from collagen, hyaluronate, fibrin, alginate, agarose, chitosan, gelatin, matrigel, glycosaminoglycans, and combinations thereof. In one example, the gel may comprise gelatin methacrylate (GelMA), which is denatured collagen that is modified with photopolymerizable methacrylate (MA) groups. Suitable hydrogels may comprise a synthetic polymer. In certain embodiments, hydrogels may include those derived from poly(acrylic acid) and derivatives thereof, poly(ethylene oxide) and copolymers thereof, poly(vinyl alcohol), polyphosphazene, and combinations thereof. The extracellular matrix material and/or the extracellular matrix composition may comprise a naturally derived biocompatible material, such as one or more extracellular matrix components, including collagen (e.g., I, III, and IV), fibrin, fibronectin, fibrinogen, gelatin (e.g., low and high bloom gelatin and/or temperature treated), laminin, hyaluronates (e.g., hyaluronic acid), elastin, and/or proteoglycans. Other suitable biocompatible materials for the extracellular matrix material and/or the extracellular matrix composition may include variations and/or combinations of cellulose, Matrigel, acrylates, acrylamides, polylactic co-glycolic acid, epoxies, aldehydes, ureas, alcohols, polyesters, silk, carbopol, proteins, glycosaminoglycans, carbohydrates, minerals, salts, clays, hydroxyapatite, and/or calcium phosphate. Further examples may include variations and/or combinations of N-Isopropylacrylamide (NIPAAM), Polyethylene glycol (PEG), gelatin methacrylate (GelMA), Polyhydroxyethylmethacrylate (PHEMA). Combinations of the above listed materials are also contemplated for use as the extracellular matrix material and/or the extracellular matrix composition.

In a preferred embodiment, the extracellular matrix material and/or the extracellular matrix composition may comprise gelatin and fibrin. The gelatin and fibrin may form an interpenetrating polymer network that mimics natural extracellular matrix (ECM) and may be optimized for cell attachment, bioprinting, transparency, and biocompatibility. The fibrin-gelatin interpenetrating polymer network may be created by mixing solutions of fibrinogen and gelatin with transglutaminase (TG), a slow-acting $Ca^{2+}$ dependent enzyme, to create a gel-precursor solution that may later be mixed with bovine thrombin to create a fibrin gel backbone, as illustrated in FIGS. 13A-13D. Fibrin may be made from a concentrated fibrinogen solution that has been activated by bovine thrombin and calcium chloride. Fibrin is a rapidly coagulating phase that permits rapid, controllable gelation of a printed structure. Advantageously, fibrin and gelatin can be welded together via mobile surface chain entanglement, while forming a strong interface. Creating monolithic gels of this nature is possible due to the slow crosslinking kinetics of transglutaminase (TG). Although thrombin rapidly induces fibrin gel formation, the gelatin present in the IPN allows one to print sacrificial ink on the already cast layer, and, ultimately, to encapsulate with liquid gelatin-fibrin. The two phases may weld together, creating a monolithic gel. This material system, which is discussed further below in the Examples, can be readily tailored to modify gelation kinetics, interface adhesion, mechanical properties, optical properties, and cell-material interactions.

As described above, one or more sacrificial filaments comprising a fugitive ink may be deposited on and/or in a substrate to form a vascular pattern that interpenetrates one or more tissue patterns. The vascular pattern comprises a two- or three-dimensional interconnected arrangement or network of the one or more sacrificial filaments. Removal of the fugitive ink after partial or complete encapsulation with the extracellular matrix composition creates a perfusable network of vascular channels in the tissue construct. Because, like the cell-laden filaments, the sacrificial filaments may be deposited in a 3D printing process that involves extrusion through a micronozzle, it may be advantageous for the fugitive ink to: (1) exhibit shear thinning behavior; (2) exhibit a defined yield stress $\tau_y$; and/or (3) have a shear elastic modulus G' and a shear viscous modulus G" modulus where G'>G" at room temperature.

The substrate for deposition typically comprises a material such as glass or other ceramics, silicone, PDMS, acrylic, polyurethane, polystyrene or other polymers. In some embodiments, the substrate may comprise living tissue or dehydrated tissue, or one of the extracellular matrix compositions described above. The substrate may be cleaned and surface treated prior to printing. For example, glass substrates may undergo a silane treatment to promote bonding of the cell-laden filaments to the glass substrate. In some embodiments, it is envisioned that the substrate may not be a solid-phase material but may instead be in the liquid or gel phase and may have carefully controlled rheological properties, as described, for example, in W. Wu et al., *Adv. Mater.* 23 (2011) H178-H183, which is hereby incorporated by reference. In the work of Wu et al., a fugitive ink was printed directly into synthetic hydrogels to create network structures. However, these synthetic materials do not support cell attachment and proliferation, limiting their use to non-biological applications. In the present disclosure, an extracellular matrix composition that facilitates cell attachment, migration, proliferation, and tissue-specific function while maintaining the appropriate rheology for printing is described. The cell-laden and sacrificial filaments are embedded in the extracellular matrix composition during printing, and thus the at least partial surrounding of the tissue and vascular patterns with the extracellular matrix composition occurs during deposition of each of the cell-laden and sacrificial filaments, as shown schematically in FIG. 21A. This includes arbitrarily complex 3D structures that may require support material during printing, as shown for example in FIG. 21C. When the forming and embedding of the tissue and vascular patterns occurs simultaneously, as described above, the substrate onto which and/or into which deposition occurs may be considered to be the container that holds the extracellular matrix composition or the extracellular matrix composition itself.

To form the extracellular matrix composition, a microgel (e.g., a poly(acrylic acid) (PAA) microgel) may be used as a rheological modifier and blended with one or more extracellular matrix materials, as set forth previously, such as gelatin methacrylate. A semi-interpenetrating polymer network (semi-IPN) may be formed, as shown schematically in FIG. 21B. Microgels may be understood to comprise colloidal gel particles that are composed of chemically cross-linked three-dimensional polymer networks. Microgels may act as sterically stabilized colloids with only a shell and no core. They can vary in composition and may include PAA, polystyrenes, PEG, and/or other biomaterials. It is contemplated that a natural extracellular matrix or biomaterial may be converted into a microgel form to impart the ideal rheology. Examples of suitable biomaterials include hyaluron, collagen, alginate, fibrin, albumin, fibronectin, elastin, or matrigel. Alternatively, synthetic materials such as PEG, acrylates, urethanes, or silicones may be modified in a similar manner.

Figure 22:
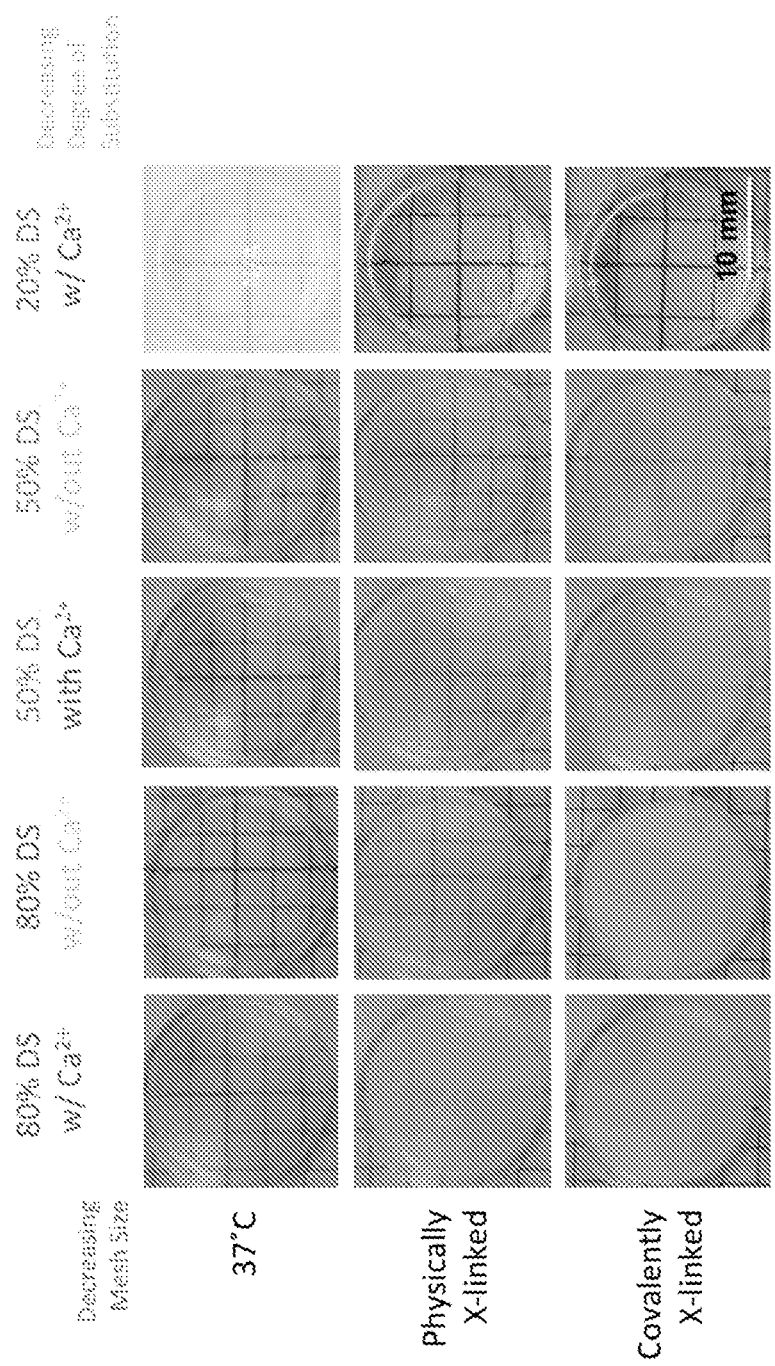
FIG. 22 demonstrates that the transparency of a semi-IPN extracellular matrix composition may be tuned by degree of substitution (DS).

Representative rheological measurements of ink and matrix rheology that are appropriate for embedded printing are shown in FIG. 21D. In one example, a high molecular weight (>1.25 MDa) PAA microgel is used as a rheological modifier and blended with gelatin-methacrylate (GelMa) to create an extracellular matrix composition that supports the creation of complex 3D vascular networks, which can be endothelialized as described previously. The transparency of the extracellular matrix composition may be altered by varying the degree of substitution and mesh size, as shown in FIG. 22. FIG. 21E shows a vascular cube demonstrating the control over the embedded printing of 3D vascular networks, and FIG. 21F shows a printed cell-laden filament within a PAA-GelMA extracellular matrix composition.

The method may further include, prior to surrounding or encapsulating the tissue and vascular patterns with the extracellular matrix composition, depositing one or more structural filaments layer by layer on and/or in the substrate in a predetermined pattern to form a mold. The structural filaments may comprise one or more structural materials selected from among the exemplary extracellular matrix compositions or extracellular matrix materials provided above. The mold may hold the extracellular matrix composition during the encapsulation and may remain as part of the tissue construct, or it may be removed after processing. The structural filaments may define the perimeter of the tissue construct on and/or in the substrate and all or at least a portion of the three-dimensional shape of the tissue construct out of the XY plane.

The mold may also have other functionalities besides defining the shape of the tissue construct. For example, the mold may serve as an interface for perfusion of channels in a printed tissue construct. FIGS. 15A-15D and 15E-15G show exemplary designs of printed molds or interface structures. The exemplary mold shown in FIGS. 15A-15D is designed for passive rocking perfusion. The mold, which may also be referred to as an interface structure, can hold vascularized tissue in place during rocking by immobilizing the tissue construct between a base portion of the mold, which may comprise PDMS, and an overlying cover, which may comprise glass. The perfusion may be for a short time periods (i.e., 14 days). In certain embodiments, vascularized tissues may be perfused on chip for long time periods (>3 months).

In certain embodiments, as described in the Examples section, the tubular tissue construct may be printed and/or embedded into vascularized matrix on a mold, e.g., perfusable chip for arterial and venous circulation.

Figures 26A, 26S:
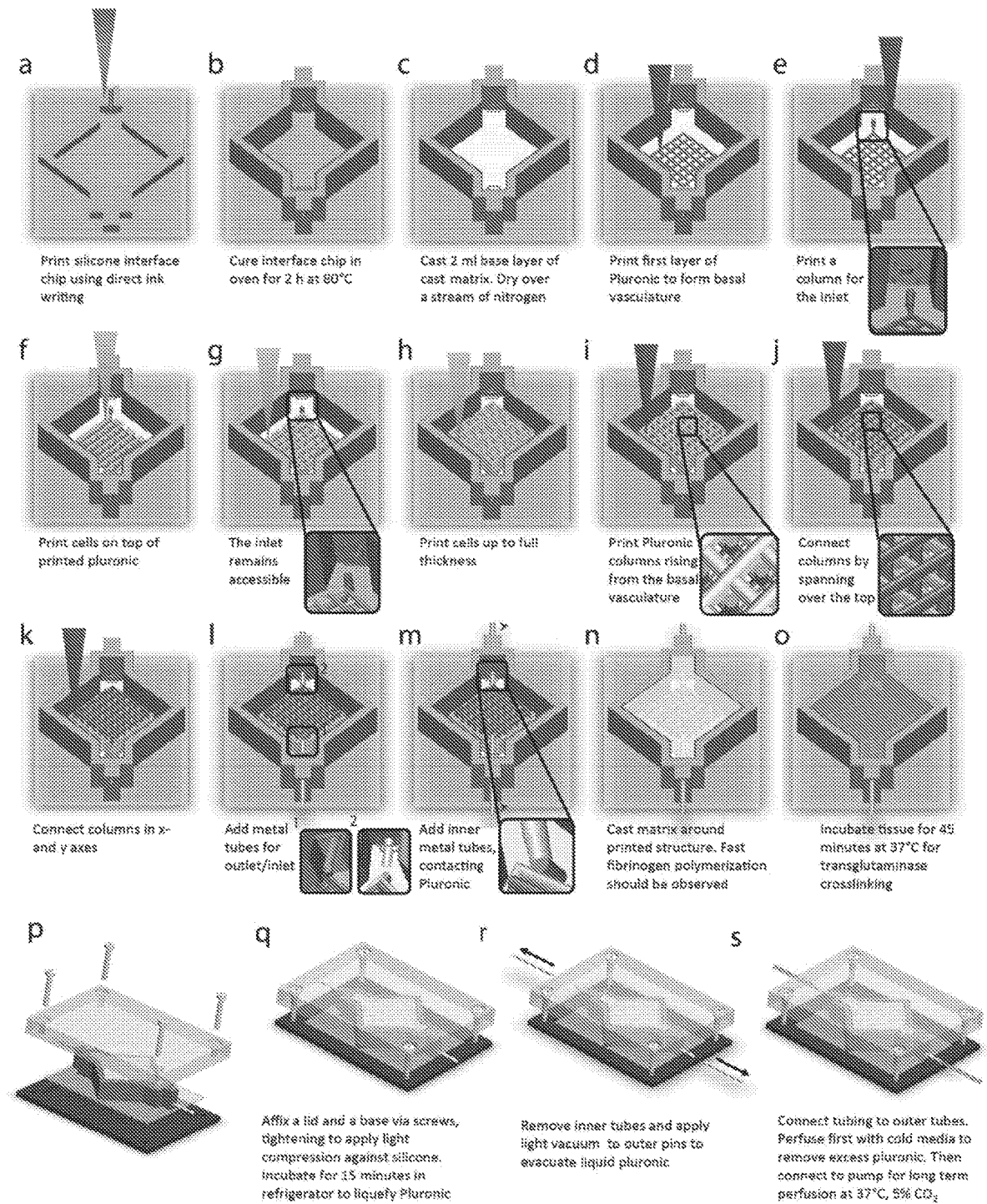
FIGS. 26A-26S depict a schematic illustration of the construction of a silicone interface chip and perfusion of a thick vascularized tissue on the chip.

To manufacture the customized perfusion chips, the silicone ink may be loaded into a syringe, centrifuged to remove air bubbles, and deposited through a tapered nozzle (e.g., 410 µm); printed using a direct ink writing (see FIGS. 26A-B). The gasket design may be created using custom MATLAB software and the structures may be printed onto, e.g., 50 mm×75 mm glass slides. After printing, the chips may be cured at 80° C. in an oven for >1 hour and stored at room temperature.

In certain further embodiments, printing of the tubular tissue construct on a perfusable chip allows for exposing the tubular tissue construct to one or more biological agents, a biological agent gradient, a pressure, and/or an oxygen tension gradient. The one or more biological agents, the biological agent gradient, the pressure, and/or the oxygen tension gradient further direct development, differentiation, and/or functioning of the tubular tissue construct.

Figure 15A:
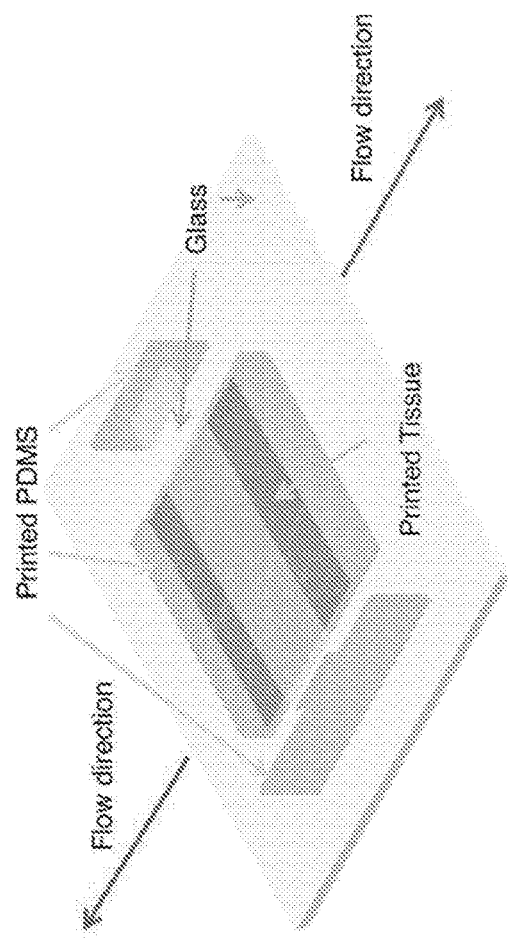
FIGS. 15A-15D show an exemplary mold for passive rocking perfusion of a tissue construct.
Figures 15B, 15C, 15D:
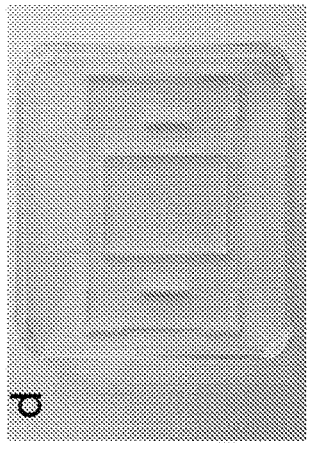
Figure 15E:
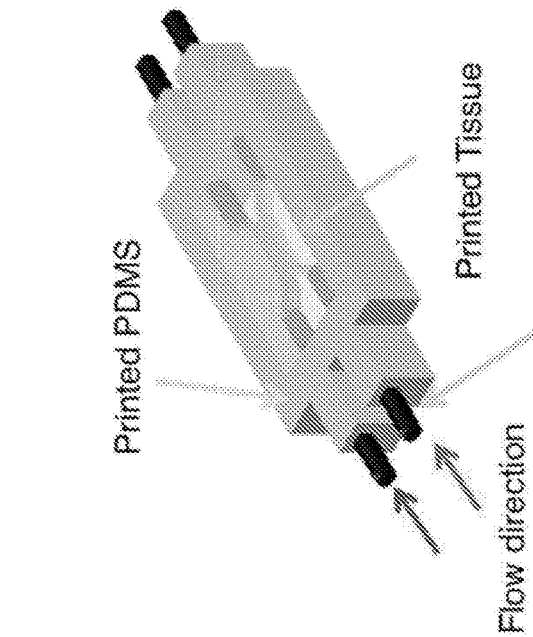
FIGS. 15E-15G show exemplary molds for active pump-based perfusion of a tissue construct.
Figure 15F:
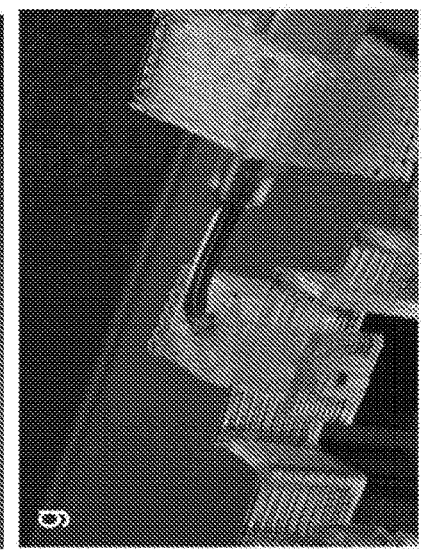
Figure 15G:
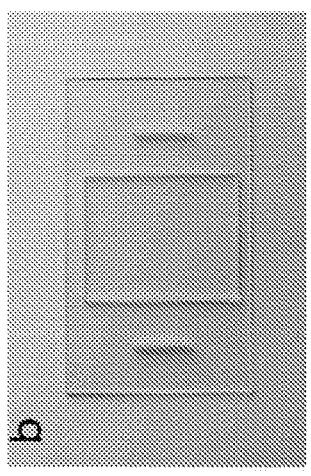

The mold designs of FIGS. 15E-15G enable active pump-based perfusion of a tissue construct and include flow channels that are in fluid communication with (e.g., contiguous with) the vascular channels of the tissue construct. Conduits that serve as flow channels may be partially or fully embedded in the mold itself and hollow pins (e.g., metal pins) may be used to interface with the vascular channels, as shown in FIGS. 15F-15G. The exemplary mold shown in FIG. 15E has a wall with multiple buttresses that contain the flow channels, which include hollow pins extending into the interior of the mold, where the tissue construct is fabricated. The vascular channels of the tissue construct may be contiguous with apertures of the hollow pins to enable flow to be introduced into the vascular channels from tubing connected to the flow channels, and fluid may be removed from the vascular channels through one or more other apertures.

In one example, the mold may be formed of an elastomeric silicone, a structural material known to be viscoelastic, non-toxic, biocompatible, and capable of forming reversible press-to-fit seals. The structural material may be 3D printed to form one or more uncured structural filaments comprising one or more of silicone, epoxies, esters of acrylic acid, or one of the extracellular matrix compositions provided above. After printing is complete, the structural filament(s) may be cured (e.g. by heating or photopolymerizing) for a suitable time duration (e.g., about one hour or more), after which the mold may exhibit the desired material properties.

The encapsulation of the tissue and vascular patterns may comprise casting a liquified matrix precursor into the mold and gelling the matrix precursor to form the extracellular matrix composition. Casting of the matrix precursor may take place at a temperature of from about 25° C. to about 40° C. For example, gelatin methacrylate, or GelMA, may be cast at a temperature of about 37° C. After casting, the matrix precursor may be cooled (e.g., to about 15° C. in the case of GelMA or 4° C. in the case of Gelbrin) to form a rigid physical gel. Alternatively, the encapsulation may occur during deposition of the tissue and vascular patterns in an embedded or omni-directional 3D printing process, as indicated above. It is also contemplated that the extracellular matrix composition may be deposited by filament deposition, similar to the cell-laden and sacrificial filaments. For example, one or more ECM filaments comprising the extracellular matrix composition may be extruded from a nozzle and deposited on and/or in the substrate layer by layer to build up the desired 3D geometry, as described below. In such a case, it may not be necessary to employ a mold to contain the extracellular matrix composition.

The extracellular matrix composition may be cured before or after removal of the fugitive ink to form a permanently chemically cross-linked structure. Depending on the extracellular matrix composition, the curing may entail heating, UV radiation or chemical additives (e.g., enzymatic curing).

Any or all of the filaments deposited on and/or in the substrate—including the cell-laden filaments defining the one or more tissue patterns, the one or more sacrificial filaments defining the interpenetrating vascular pattern or a functional channel pattern, the one or more structural filaments that may define the mold, and/or the one or more ECM filaments that may yield the extracellular matrix composition—may be extruded from a nozzle before being deposited on and/or in the substrate. In the discussion of the extrusion process that follows, the sacrificial filaments, the cell-laden filaments, the structural filaments and/or the ECM filaments may be collectively referred to as "the filaments" since the processing steps may be applicable to any or all of the filament compositions.

Figure 4:
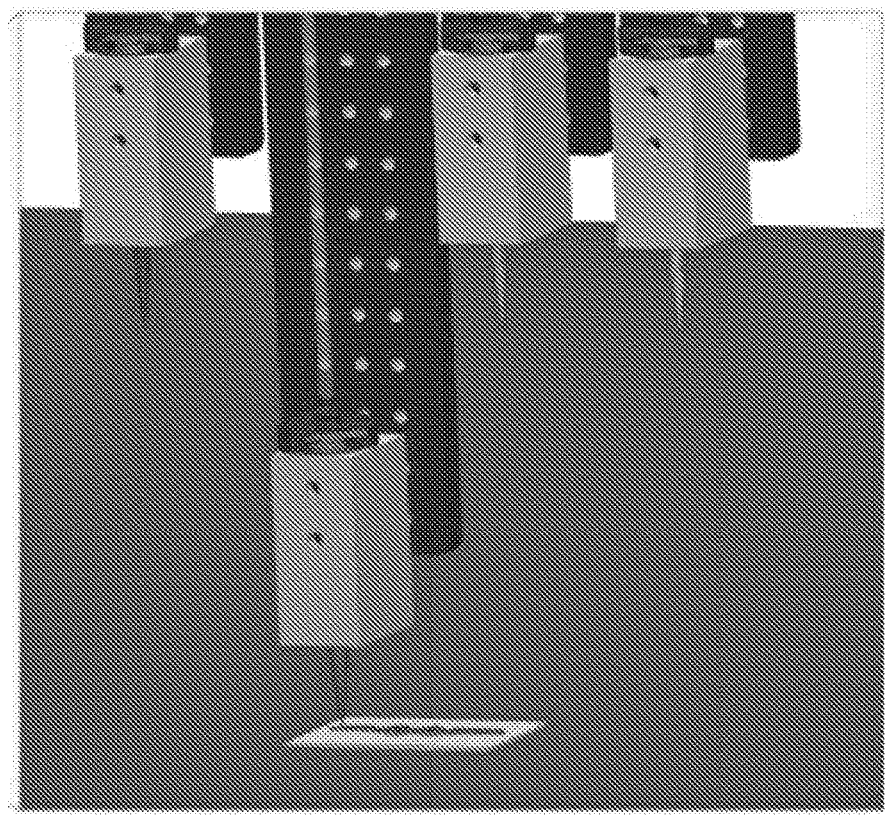
FIG. 4 shows four print heads (nozzles) mounted onto a custom 3D printer where each z-axis is controlled independently.
Figures 5A, 5B, 5C:
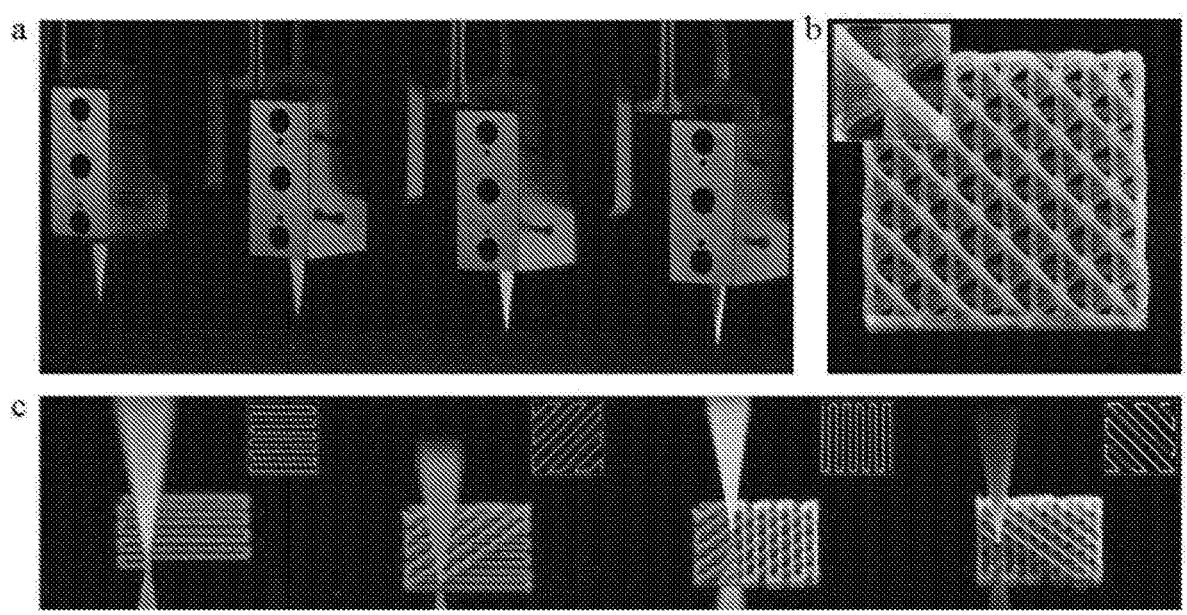
FIG. 5A also shows four print heads (nozzles)
FIG. 5B shows a four-layer microstructure where complex ink patterns are deposited sequentially from four nozzles to form the four-layer microstructure with varied composition.
FIG. 5C shows sequential fabrication images of each layer of the deposition process, where each inset illustrates the geometry of each layer.

FIG. 4 shows four exemplary nozzles or print heads that may be employed to extrude the filaments and deposit them on and/or in the substrate. The nozzles shown are part of a custom-built 3D printer comprising a large build platform (750 mm×650 mm) equipped with four independent z-axes. FIGS. 5A-5C provide a demonstration of the 3D printing of a four-layer, multimaterial construct by sequential deposition of a filament of a different composition from each of the four nozzles. The insets of FIG. 5C show, for each layer, the repeating unit of the 3D structure.

Although there are four nozzles for the exemplary printer of FIGS. 4 and 5A, the number of nozzles employed to form the tissue construct by 3D printing may be lower or higher. In general, 1 or more, 2 or more, 3 or more, 4 or more, 5 or more and up to N nozzles may be used for extruding the filaments, where $1 \leq N \leq 1024$, and more typically N is no more than 512, N is no more than 256, N is no more than 128, or N is no more than 64. The filaments may be extruded from the N nozzles sequentially in a serial deposition process or simultaneously in a parallel deposition process, where each nozzle may contain a different precursor ink (e.g., a cell-laden ink comprising one or more predetermined cell types, a fugitive ink, a structural ink, or an ECM ink). It is also contemplated that the deposition may include both parallel and serial deposition steps. To facilitate sequential or serial printing, the nozzles can be independently controlled in the z-direction, as shown in FIG. 4.

Each nozzle may have an inner diameter of from about 1 micron to about 1 mm in size, and more typically from about 50 microns to about 500 microns. The size of the nozzle may be selected depending on the desired filament diameter. Depending on the injection pressure and the nozzle translation speed, the deposited filament may have a diameter ranging from about 1 micron to about 10 mm, and more typically from about 100 microns (0.1 mm) to about 1 mm. The inks fed to the nozzles may be housed in separate syringe barrels that may be individually connected to a nozzle for printing by way of a Luer-Lok™ or other connector. The extrusion of each of the filaments may take place under an applied pressure of from about 1 psi to about 200 psi, from about 10 psi to about 80 psi, or from about 20 psi to about 60 psi. The pressure during extrusion may be constant or it may be varied. By using alternative pressure sources, pressures of higher than 100 psi or 200 psi and/or less than 1 psi may be applied during printing. A variable pressure may yield a filament having a diameter that varies along the length of the filament. Such an approach may be used, for example, to form the branching, hierarchical vascular network shown in FIG. 2C and in FIGS. 7E-7F, which is formed from sacrificial filaments of various lengths and diameters. The extrusion may be carried out at ambient or room temperature conditions (e.g., from about 18° C. to about 25° C.).

During the extrusion and deposition of each filament, the nozzle may be moved along a predetermined path (e.g., from $(x_1, y_1, z_1)$ to $(x_2, y_2, z_2)$) with a positional accuracy of within ±100 microns, within ±50 microns, within ±10 microns, or within ±1 micron. Accordingly, the filaments may be deposited with a positional accuracy of within ±200 microns, within 100 microns, within ±50 microns, within ±10 microns, or within ±1 micron. The nozzles may be moved and the filaments may be deposited at speeds as high as about 3 m/s (e.g., from about 1 cm/s to about 3 m/s), and are more typically in the range of from about 1 mm/s to about 500 mm/s, from about 1 mm/s to about 100 mm/s, or from about 1 mm/s to about 10 mm/s.

The predetermined path of the nozzle may have an XY boundary area of at least about 2400 cm², at least about 2700 cm² and up to about 1 m² as determined by the size of the build platform of the printer. For example, the build platform may have a length of from about 60 cm to about 100 cm and a width of from about 40 cm to about 100 cm. Each print head may be moved in the z-direction a distance from about 10 cm to about 50 cm, or about 15 to about 30 cm.

The deposited filaments are formed from precursor inks (e.g., cell-laden inks comprising one or more predetermined cell types, fugitive inks, structural inks, or ECM inks) having a suitable composition and rheological properties. The precursor inks may be viscoelastic and comprise a viscosity with a non-linear shear dependence. The viscosity of the precursor inks may fall in the range of from about 0.001 Pa-sec to about 10,000 Pa-sec. The precursor inks may optionally include viscosifiers to help control the rheological properties. Each cell-laden ink, and optionally, the fugitive and/or ECM ink, may include one or more cells of one or more predetermined cell types in a carrier that may be a liquid or a gel. The carrier may include, in addition to an extracellular matrix material as described above, one or more functional chemical substances as described above. The carrier may also or alternatively include a cell culture medium designed to support the growth of cells. In one example, to form a cell-laden ink comprising viable cells mixed with a hydrogel, a predetermined amount of a hydrogel precursor powder is mixed with a cell culture medium to form a solution of an appropriate composition. The cells of interest are then dispersed in the solution at the desired cell concentration (e.g., any of the cell concentrations set forth above for the cell-laden filaments), and mixed thoroughly. Steps to prepare exemplary cell-laden GelMA inks, cell-laden gelatin-fibrin inks, Pluronic F127 fugitive inks, and PDMS structural inks are described in the Examples below.

After encapsulation of the tissue and vascular patterns, the fugitive ink may be removed to form a network of vascular channels in the extracellular matrix composition. The fugitive ink may comprise a biocompatible material and may be designed for compatibility with the cell-laden formulations and the extracellular matrix composition during room temperature deposition. Suitable fugitive inks may include, for example, Pluronic F127, Pluronic F123, agarose, sugar, wax, and fatty oils (e.g., animal fat derived oils such as Crisco). If a hydrogel is employed for the extracellular matrix composition (and/or the extracellular matrix material), and a hydrogel such as Pluronic F127 is employed as the fugitive ink, it may be advantageous for the fugitive ink and the matrix hydrogel to have similar water contents (e.g., within ±30%) to avoid distortion of the fugitive ink after printing. The fugitive ink and the extracellular matrix composition may also be selected to have complementary thermal transitions, as discussed further below.

Pluronic F127 is an FDA-approved material that is biologically inert to multiple cell types over the short time periods needed to complete the fabrication process. The material includes a hydrophobic poly(propylene oxide) (PPO) segment and two hydrophilic poly(ethylene oxide) (PEO) segments arranged in a PEO-PPO-PEO configuration. Pluronic F127 undergoes thermally reversible gelation above a critical micelle concentration (CMC; about 21 wt. %) and the gelation temperature. The gelation temperature decreases from approximately 10° C. to 4° C. as the PEO-PPO-PEO concentration increases. When both of these critical parameters are exceeded, micelles form as the hydrophilic PEO segments self-assemble into corona that are well solvated by water, while the hydrophobic PPO segments tightly associate within the micelle cores. However, below the gelation temperature, the hydrophobic PPO units are hydrated, such that individual PEO-PPO-PEO species become soluble in water giving rise to a gel-to-fluid transition for systems whose concentration exceeds the CMC. Thus, the material liquifies upon cooling below the gel point.

It is important that the patterned cells and surrounding extracellular matrix composition are not damaged during deposition of the sacrificial filaments or removal of the fugitive ink, and thus it is preferred that harsh solvents and/or elevated temperatures are not utilized during the removal process. With proper selection of the fugitive ink and the extracellular matrix composition/material, the fugitive ink may be removed without damage to the tissue construct. For example, if the fugitive ink undergoes a gel-to-fluid transition as described above, cooling of the vascular pattern after encapsulation may be effective for removal of the fugitive ink. To remove Pluronic F127, the vascular pattern may be cooled to a temperature of no more than about 1° C., depending on the concentration. It is also contemplated that the fugitive ink may be dissolved in a suitable aqueous solution for removal. Once the fugitive ink is liquefied or dissolved, a vacuum may be applied to an exposed end of the vascular pattern to extract the ink.

Figure 16A:
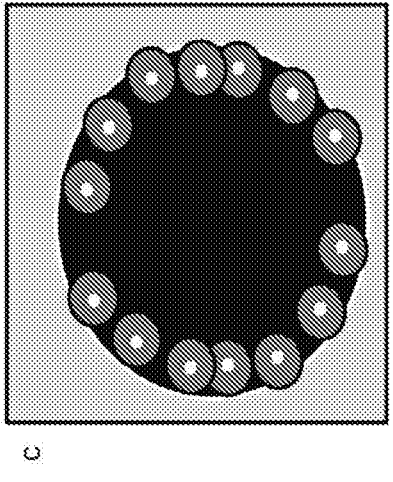
FIGS. 16A-16C show schematically the deposition of endothelial cells within a sacrificial filament formed from a fugitive ink, encapsulation of the sacrificial filament with an extracellular matrix composition, and evacuation of the fugitive ink to form a channel with endothelial cells lining the channel wall.
Figure 16B:
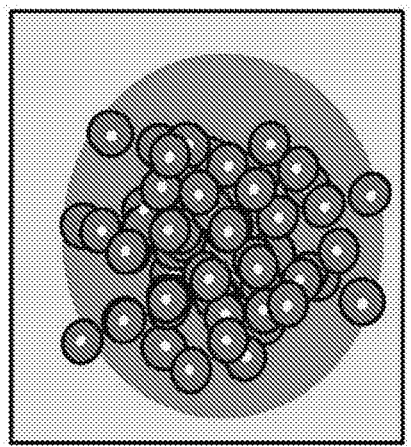
Figure 16C:
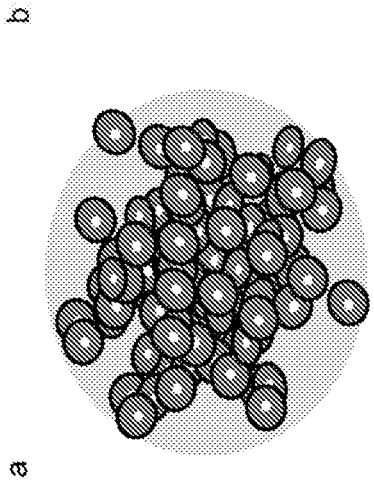
Figure 16D:
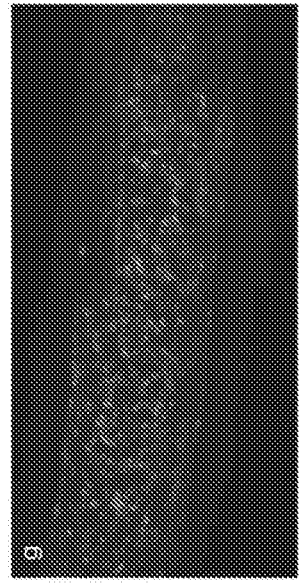
FIG. 16D shows an as-printed fugitive ink (Pluronic F127) comprising a dispersion of HUVECs.
Figure 16E:
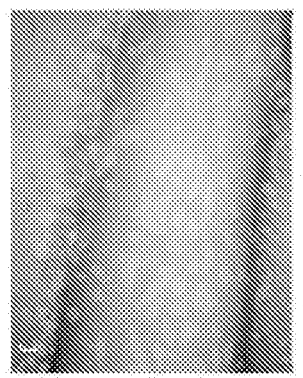
FIG. 16E shows the fugitive ink after casting and liquefying.
Figure 16F:
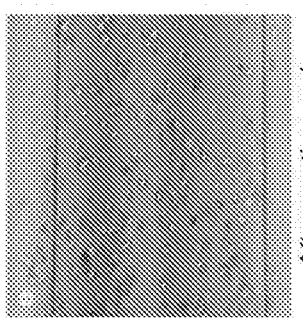
FIG. 16F shows the vascular network after 1 day of incubation of the HUVECs.

Advantageously, the tissue constructs may be designed to support the attachment and proliferation of endothelial cells, which line vascular channels providing a barrier to fluid diffusion, while simultaneously facilitating homeostatic functions and helping establish vascular niches specific to the various tissues. To promote endothelialization, in some embodiments the sacrificial filament(s) comprising the fugitive ink may further include a plurality of endothelial cells or other viable cells. The cells may be deposited along with the sacrificial filament and may remain in the vascular channels after removal of the fugitive ink, as illustrated in FIGS. 16A-16C. Direct cellularization of the channels can be achieved if the cells adsorb to the channel walls after liquidation of the fugitive ink. This approach may allow one to incorporate viable cells into highly tortuous networks or small channels that may be difficult to infill using direct injection due to an increased resistance to flow. An exemplary printed tissue construct including a channel formed by evacuation of a fugitive ink comprising endothelial cells and Pluronic F127 is shown in FIGS. 16D-16G, and is further described in the Examples. In another example, epithelial cells may be delivered in a fugitive ink and used to create tubular epithelial tissues present in the mammary gland, kidney or liver.

In addition to or as an alternative to depositing endothelial and/or other viable cells with the fugitive ink, endothelialization may be effected by injecting a suspension of viable cells (e.g., endothelial cells) into the vascular channels after removing the fugitive ink. Using one or both of these approaches, an endothelial layer having up to 100% confluency may be formed lining the wall of one or more of the vascular channels, where 100% confluency means that the wall is completely covered by endothelial cells. Each endothelial layer formed in the network of vascular channels may have a confluency of at least about 80%, at least about 90%, at least about 95%, at least about 98%, at least about 99%, or 100%, so that the vascular channels may function as actual blood vessels. As described in the Examples below, it has been shown that representative hierarchical bifurcating networks may be successfully injected with a human umbilical vein endothelial cell (HUVEC) suspension followed by gentle rocking (see FIG. 7J). After 48 h, these cells retained greater than 95% viability and assembled into a nearly confluent layer, as determined by live/dead staining coupled with confocal imaging within a representative, bifurcated microchannel.

Multiple types of cells may be injected into the vascular channels. In vivo, every blood vessel having a diameter larger than a capillary contains an outer fibrous tissue layer, a smooth muscle layer, and an inner layer of endothelial cells. One or more other types of cells, such as fibroblasts, may be injected into the vascular channels along with the endothelial cells after removing the fugitive ink. As described in the Examples below, the vascular channels may be co-seeded with fibroblasts and HUVECs, two cell types which may self-assemble into stromal and endothelial layers, respectively, mimicking the anatomy of native blood vessels.

It is also contemplated that the same or a different fugitive ink may be deposited as a sacrificial filament and removed as described above to form channels, ducts and/or compartments in addition to or in lieu of the vascular channels within the tissue construct. In other words, one or more additional sacrificial filaments may be deposited to form a functional channel pattern on and/or in the substrate, either in addition to or in lieu of the vascular pattern. This is shown schematically in FIG. 17A.

Figure 17A:
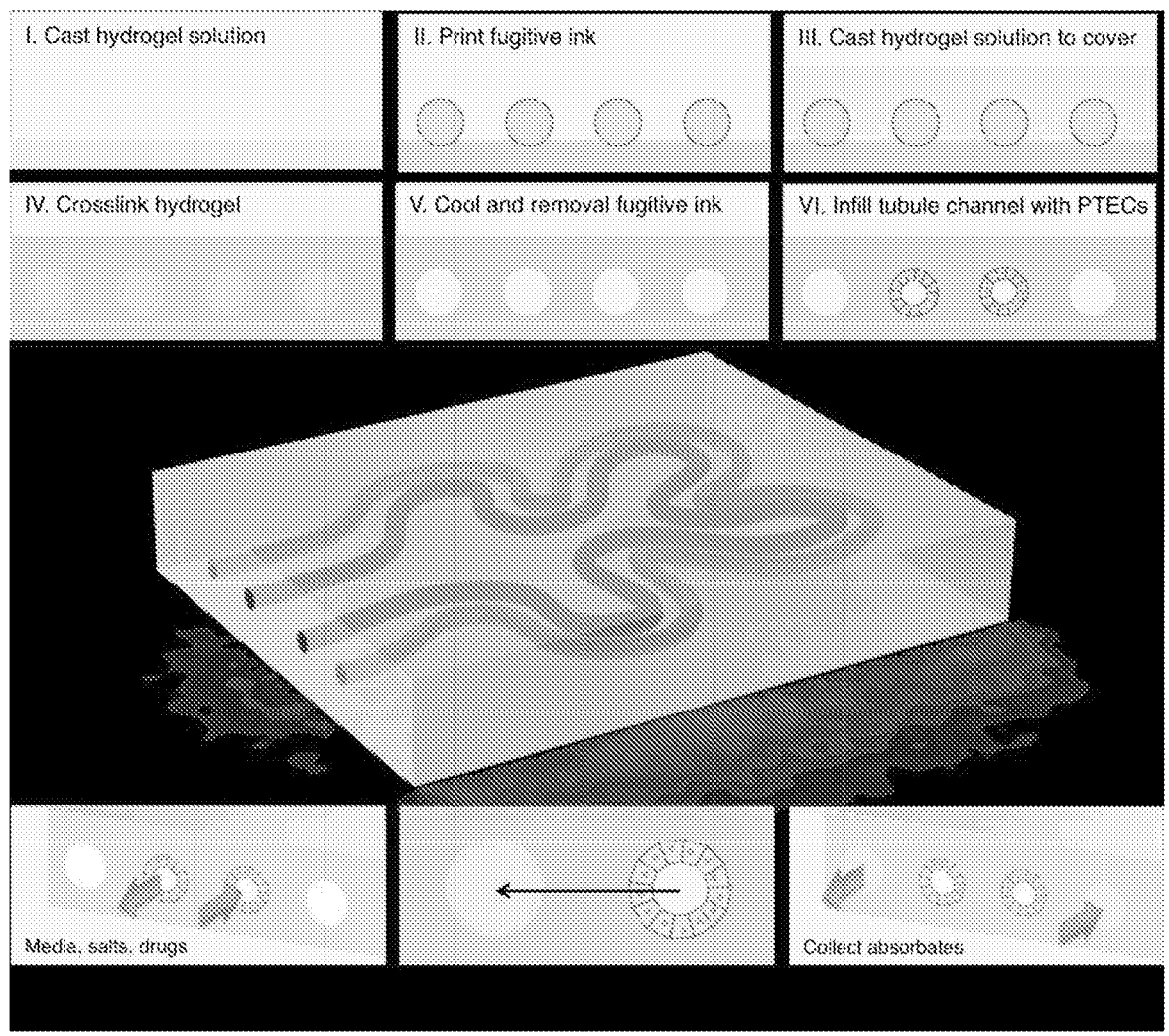
FIG. 17A illustrates the creation of one or more functional channels in an extracellular matrix composition to form a functional channel network in a tissue construct (specifically, in this example, an epithelial tissue construct). The steps include deposition of one or more sacrificial filaments comprising a fugitive ink (which may be a cell-laden fugitive ink) to form a functional channel pattern, at least partial encapsulation of the channel pattern with an extracellular matrix composition, removal of the fugitive ink to form the functional channels, and an optional seeding approach for lining the functional channels with epithelial cells.

Each additional sacrificial filament may comprise a second fugitive ink, which is the same as or different from the fugitive ink used to define the vascular pattern (if the vascular pattern is present). After deposition, the functional channel pattern may be at least partially surrounded with the extracellular matrix composition (e.g., the hydrogel solution shown in step III of FIG. 17A), as described above in reference to the vascular pattern. It is also contemplated that the at least partial surrounding of the functional channel pattern with the extracellular matrix composition may occur during deposition of the one or more sacrificial filaments, such that the one or more functional channel patterns are simultaneously formed and embedded in the extracellular matrix composition. When the forming and embedding of the functional channel patterns occurs simultaneously, the substrate onto which and/or into which deposition occurs may be considered to be the container that holds the extracellular matrix composition or the extracellular matrix composition itself. The second fugitive ink may then be removed, as illustrated in step V of FIG. 17A and as described above in reference to the vascular channels, to create one or more functional channels in the extracellular matrix composition. Thus, a functional channel network may be formed in the tissue construct, which in this example is an epithelial tissue construct, as shown in FIGS. 17A (center) and 17B. One or more types of viable cells (e.g., epithelial cells) may be deposited with the additional sacrificial filaments, and at least a portion of the viable cells may remain in the one or more functional channels after removal of the second fugitive ink. Also or alternatively, after removing the second fugitive ink, a suspension of viable cells (e.g., epithelial cells) may be injected into the functional channels, as shown in step VI of FIG. 17A.

The functional channels may define tubular tissues or tissue components. Examples of tubular structures that can be formed via 3D printing and epithelialization include, but are not limited to, a nephron (of the kidney), the tubule portion of the nephron (of the kidney), intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph. Such a printed epithelial tissue construct may comprise one or more functional channels comprising an epithelial layer thereon, and an extracellular matrix composition may at least partially surround the one or more functional channels, as illustrated in FIGS. 17A (center) and 17B. A stromal layer may also be present on the epithelial layer. The printed epithelial tissue construct may further comprise one or more tissue patterns, each comprising a plurality of viable cells of one or more predetermined cell types, in the extracellular matrix composition, as set forth above. The viable cells and the one or more predetermined cell types may comprise epithelial cells and/or another cell type described previously. The printed epithelial tissue construct may further comprise a network of vascular channels in the extracellular matrix composition, also as described above.

For example, a network of vessels (channels) of the lymphatic system may be created using sacrificial filaments comprising a fugitive ink. In another example, compartments of any desired geometry may be embedded within the tissue construct by depositing a predetermined arrangement of sacrificial filaments. Such embedded compartments may be used for containing growth factors, additional cells and/or supplemental scaffold materials that may in some embodiments be deposited with the sacrificial filaments to direct cell behavior, differentiation, function, movement and/or growth.

Figure 17B:
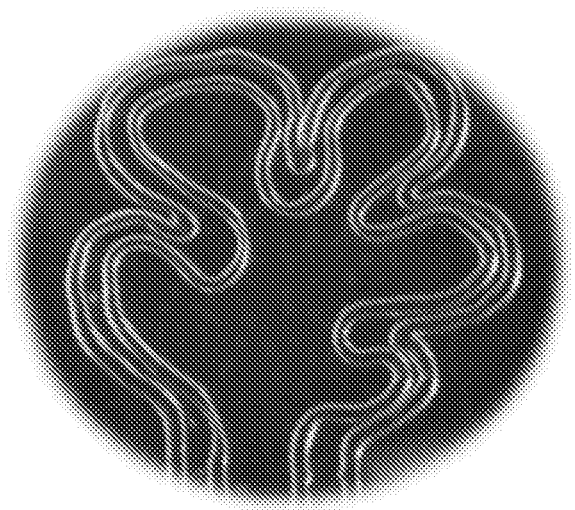

A printed epithelial tissue construct comprising a functional channel that is subsequently seeded with epithelial cells (epithelialization) is shown in FIGS. 17A-17F. Referring to FIGS. 17A-17B, the printed tissue construct is a proximal convoluted tubule, a portion of the nephron. It can be printed in a simple or convoluted shape and seeded with epithelial cells, which thrive and circumscribe the functional channels, as shown in FIGS. 17C-17F. The cells employed are human renal proximal tubule cells (PTEC); however, this approach may be applied to any of a number of types of epithelial tissue. For example, in vitro models may be fabricated for tissue-specific disease and toxicity studies. This type of functional human tissue mimic can be used as a building block for the growth of larger organs or for high throughput drug toxicity and screening.

A printed tubular tissue construct, such as a nephron described below, including at least two types of viable cells, each type of viable cells being positioned along a different predetermined location of the tubular tissue construct and methods of 3D printing the tubular tissue construct are described.

Figures 23A, 23B, 23C, 23D, 23E:
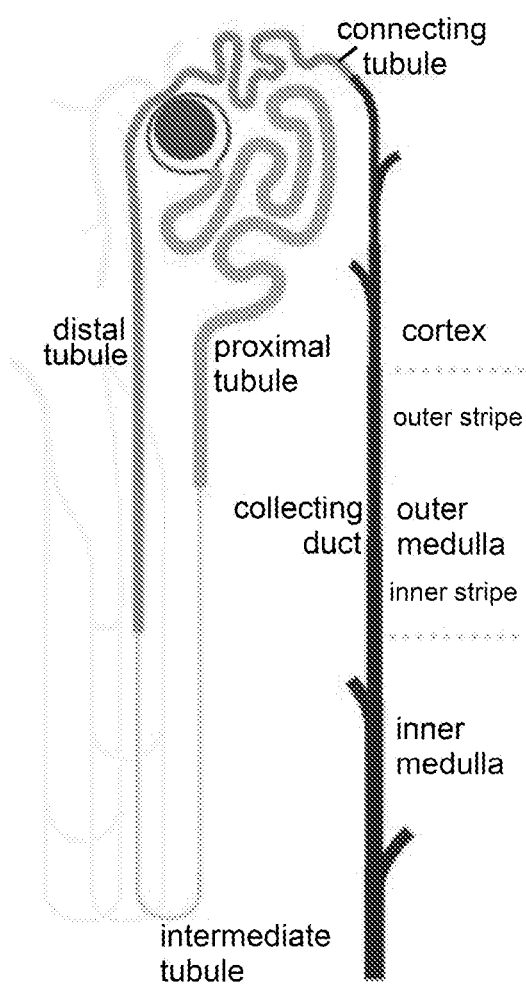
FIG. 23A is an illustration of a nephron.
FIGS. 23B-E are photographs depicting cross-sectional views of the nephron showing types of cells present in the nephron.

A kidney consists of two regions: an outer region (cortex) and an inner region (medulla). The cortex and medulla are composed on nephrons (which are the functional units of the kidney), blood vessels, lymphatics, and nerves. Each kidney contains approximately 1.2 million nephrons, which are hollow tubes composed of a single cell layer. As shown in FIG. 23A, each nephron consists of a renal corpuscle, a proximal tubule, a loop of Henle, a distal tubule, and a collecting duct system.

The first step in urine formation begins with the ultrafiltration of plasma across the glomerular capillaries (i.e., glomerulus). The glomerulus consists of network of capillaries supplied by the afferent arteriole and drained by the efferent arteriole. The capillaries are covered by epithelial cells, called podocytes, which form the visceral layer of Bowman's capsule. The visceral cells are reflected at the vascular pole to form the parietal layer of Bowman's capsule. The space between the visceral layer and the parietal layer is called Bowman's space, which at the urinary pole of glomerulus, becomes the lumen of the proximal tubule. The endothelial cells of glomerular capillaries are covered by a basement membrane, which is surrounded by podocytes.

The proximal tubule initially forms several coils, followed by a slight piece that descends toward the medulla. The next segment is Henle's loop (noted as "intermediate tubule" in the figure), which is composed of the straight part of the proximal tubule, the descending thin limb, the ascending thin limb (only in nephrons with long loops of Henle), and the thick ascending limb. The last segment before the collecting duct system is the distal tubule.

Each nephron segment is composed of cells that are uniquely suited to perform specific transport functions (FIGS. 23B-E). Proximal tubule cells have an extensively amplified apical membrane (the urine side of the cell, called the brush border), which is only present in the proximal tubule. The basolateral membrane (the blood side of the cell) is highly invaginated. These invaginations contain many mitochondria. In contrast, the descending thin limb and ascending thin limb of Henle's loop have poorly developed apical and basolateral surfaces and few mitochondria. The cells of the thick ascending limb and the distal tubule have abundant mitochondria and extensive infoldings of the basolateral membrane. The collecting duct is composed of two types of cells: principal cells and intercalated cells. Principal cells have a moderately invaginated basolateral membrane and contain few mitochondria. Intercalated cells have a high density of mitochondria. The final segment of the nephron, the inner medullary collecting duct, is composed of inner medullary collecting duct cells.

A printed tubular tissue construct that, in certain embodiments, resembles and functions as a nephron, is described. The printed tubular tissue construct includes one or more functional channels comprising a patterned cell layer thereon along the length of the functional channels, where the patterned cell layer includes the one or more types of viable cells, each type of viable cells positioned along different predetermined location of the functional channel. The patterned cell layer may include a plurality of viable cells of at least two predetermined types (as described, e.g., immediately above); alternatively, a plurality of viable cells of at least three predetermined types; and alternatively, a plurality of viable cells of at least four or more predetermined types. In certain embodiments, the patterned cell layer may include renal proximal tubule cells, loop of Henle cells and/or renal distal tubule cells, collecting duct cells, and fenestrated glomerular endothelial cells (i.e., podocytes)), mesangial cells, renal microvascular cells, renal cell progenitors, pluri or multipotent stem cells, other endothelial lineage cells, each distributed along a different predetermined location of the construct, thereby forming a nephron. In certain other embodiments, patient-specific iPSCs may be used as starting materials to derive patient-specific predetermined cell types for use in the tissue construct development. For example, patient specific iPSCs can be used to derive a pro-kidney or individual cell lines present in a nephron (e.g., renal proximal tubule cells, loop of Henle cells and/or renal distal tubule cells, collecting duct cells, and fenestrated glomerular endothelial cells (i.e., podocytes)). iPSCs-derived cells lines may then be used as the predetermined types of cells for printing patient-specific tubular tissue constructs.

Figure 23F:
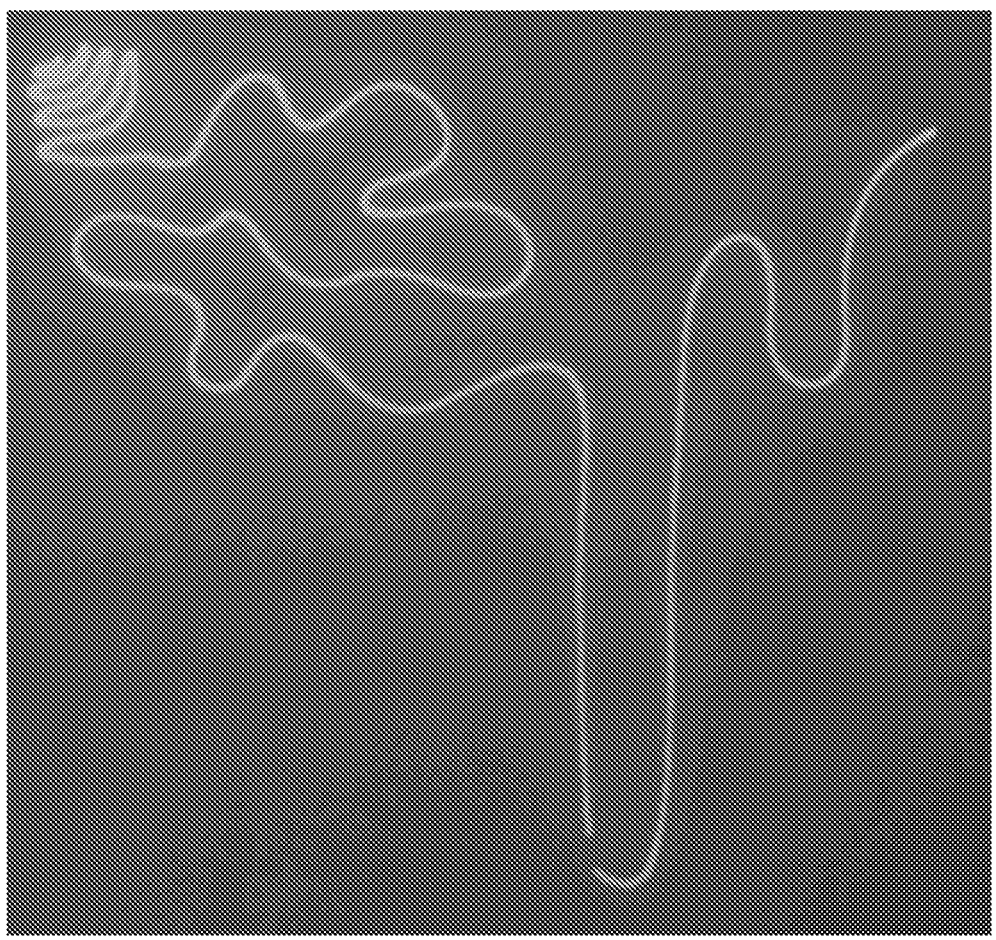
FIG. 23F is a photograph of an embedded nephron print (pluronic with fluorescent dye in Polydimethylsiloxane (PDMS)).

FIG. 23F depicts a picture of an embedded nephron print (pluronic with fluorescent dye in PDMS).

Specifically, in certain embodiments, a printed tubular tissue construct includes functional channels comprising a patterned cell layer thereon along the length of the functional channel, the patterned cell layer comprising one or more types of viable cells, each type of viable cells being positioned along a different predetermined location of the functional channel. The printed tubular tissue construct also includes an extracellular matrix composition at least partially surrounding the functional channels. The patterned cell layer may include a plurality of viable cells of at least two predetermined types (as described above). In certain embodiments, the extracellular matrix composition at least partially surrounds the one or more tissue patterns. The extracellular matrix composition may include a naturally derived biocompatible material, such as one or more extracellular matrix components, including collagen (e.g., I, III, and IV), fibrin, fibronectin, fibrinogen, gelatin (e.g., low and high bloom gelatin and/or temperature treated), laminin, hyaluronates (e.g., hyaluronic acid), elastin, and/or proteoglycans. Other suitable biocompatible materials for the extracellular matrix composition may include variations and/or combinations of cellulose, Matrigel, acrylates, acrylamides, polylactic co-glycolic acid, epoxies, aldehydes, ureas, alcohols, polyesters, silk, carbopol, proteins, glycosaminoglycans, carbohydrates, minerals, salts, clays, hydroxyapatite, and/or calcium phosphate. Further examples may include variations and/or combinations of N-Isopropylacrylamide (NIPAAM), Polyethylene glycol (PEG), gelatin methacrylate (GelMA), Polyhydroxyethylmethacrylate (PHEMA). In certain embodiments, the printed tubular tissue construct may also include a network of vascular channels in the extracellular matrix composition. In certain embodiments, the functional channels may also include immune cells, fibroblast, stem cells, iPSCs, or the like, which could lead to improved physiology or disease state modeling.

A printed tubular tissue construct with embedded vasculature may include functional channels comprising a patterned cell layer thereon along the length of the functional channel. The patterned cell layer includes one or more types of viable cells, each type of viable cells being positioned along a different predetermined location of the functional channel. In certain embodiments, the patterned cell layer includes a plurality of viable cells of at least two predetermined cell types. The extracellular matrix composition at least partially surrounds the tissue patterns. In certain embodiments, the patterned cell layer includes a plurality of viable cells of at least two predetermined cell types, wherein the extracellular matrix composition at least partially surrounds the one or more tissue patterns. The printed tubular tissue construct also includes a network of vascular channels interpenetrating functional channels and an extracellular matrix composition at least partially surrounding the functional channels and the network of vascular channels. The extracellular matrix composition may include a naturally derived biocompatible material, such as one or more extracellular matrix components, including collagen (e.g., I, III, and IV), fibrin, fibronectin, fibrinogen, gelatin (e.g., low and high bloom gelatin and/or temperature treated), laminin, hyaluronates (e.g., hyaluronic acid), elastin, and/or proteoglycans. Other suitable biocompatible materials for the extracellular matrix composition may include variations and/or combinations of cellulose, Matrigel, acrylates, acrylamides, polylactic co-glycolic acid, epoxies, aldehydes, ureas, alcohols, polyesters, silk, carbopol, proteins, glycosaminoglycans, carbohydrates, minerals, salts, clays, hydroxyapatite, and/or calcium phosphate. Further examples may include variations and/or combinations of N-Isopropylacrylamide (NIPAAM), Polyethylene glycol (PEG), gelatin methacrylate (GelMA), Polyhydroxyethylmethacrylate (PHEMA). In certain embodiments, the tubular tissue construct is a nephron, where the patterned cell layer includes at least two cell types selected from renal proximal tubule cells, loop of Henle cells, renal distal tubule cells, collecting duct cells, fenestrated glomerular endothelial cells, mesangial cells, renal microvascular cells, renal cell progenitors, pluri or multipotent stem cells, other endothelial lineage cells, induced pluripotent stem cells (iPSCs), and/or iPSCs-derived patent-specific pro-kidney or individual cell lines present in a nephron, or a combination thereof. In certain alternative embodiments, the printed tubular tissue construct with embedded vasculature may be intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph. In certain embodiments, the functional channels may also include immune cells, fibroblast, stem cells, iPSCs (including patient-specific iPSCs), or the like, which could lead to improved physiology or disease state modeling.

Different approaches may be used to generate tubular tissue constructs, such as nephrons, that include a plurality of multiple cell types along their lengths. In this regard, 3D printing methods to pattern functional cell types along the length of a single tube are described.

The first approach relates to printing a tubular tissue construct by directly depositing a plurality of cells types via a fugitive ink. Specifically, the method of printing a tubular tissue construct includes depositing sacrificial filaments on and/or in a substrate to form a functional channel pattern, each sacrificial filament comprising a fugitive ink and a plurality of predetermined types of viable cells. Each predetermined type of viable cells is deposited at a different predetermined location along a length of the sacrificial filament. Next, the functional channel pattern is at least partially surrounded with an extracellular matrix composition. Next, the fugitive ink can be removed to create functional channels in the extracellular matrix composition, at least a portion of each different predetermined type of viable cells remaining at the different predetermined location after removal of the fugitive ink, thereby forming a tubular tissue construct. Additional steps may include depositing one or more sacrificial filaments on and/or in the substrate to form an interpenetrating network of tubes, each of the sacrificial filaments comprising a second fugitive ink, and removing the second fugitive ink, thereby forming the interpenetrating network of tubes in the tubular tissue construct. A suspension of viable epithelial or endothelial cells may be injected into the one or more tubes. In certain embodiments, the interpenetrating network of tubes comprises a vascular channel pattern interpenetrating the functional channel pattern. The term "interpenetrating," in the context of the present invention means that the channel patterns may or may not be in fluid contact with each other. For example, the functional channel pattern may be in close proximity to the vascular pattern but not in fluid contact with each other (i.e., independently addressable interpenetrating networks). In certain embodiments, the at least partial surrounding of the functional channel pattern with the extracellular matrix composition may occur during deposition of the one or more sacrificial filaments, the functional channel patterns thereby being formed and embedded simultaneously in the extracellular matrix composition. As described previously, the fugitive ink can be removed by cooling the sacrificial filaments. In additional, optional step of the method, cell-laden filaments, each comprising a plurality of viable cells may be deposited on and/or in the substrate to form tissue patterns, each of the tissue patterns comprising predetermined cell types.

In certain embodiments, the sacrificial filaments can be extruded through a single printhead before being deposited on and/or in the substrate. Methods of extruding sacrificial filaments using a single printhead were previously described in U.S. Provisional Patent Application Ser. No. 62/133,039, entitled "Printhead and Method for 3D Printing of Multiple Materials," filed Mar. 13, 2015, which is incorporated herein in its entirety. Alternatively, the sacrificial filaments can be extruded through multiple printheads. Methods of extruding sacrificial filaments using multiple printheads were previously described in U.S. Pat. Pub. No. 2014/0314954, which is incorporated by reference in its entirety.

Specifically, to print a nephron, continuous sacrificial filaments are deposited on and/or in a substrate to form functional channels. Each sacrificial filament includes a first fugitive ink formulation over a first length of the sacrificial filament, a second ink formulation over a second length of the sacrificial filament, and a third ink formulation over a third length of the sacrificial filament. Additional fugitive ink formulations may also be used. The first fugitive ink formulation comprises a fugitive ink and a first type of cells, e.g., renal proximal tubule cells; the second fugitive ink formulation comprises the fugitive ink and a second type of cells, e.g., loop of Henle cells; and the third fugitive ink formulation comprises the fugitive ink and a thirst type of cells, e.g., renal distal tubule cells, etc. Additional fugitive ink formulations may include collecting duct cells, fenestrated glomerular endothelial cells, mesangial cells, renal microvascular cells, renal cell progenitors, pluri or multipotent stem cells, other endothelial lineage cells, induced pluripotent stem cells (iPSCs), and/or iPSCs-derived patent-specific pro-kidney or individual cell lines present in a nephron. Next, the functional channel pattern is at least partially surrounded with an extracellular matrix composition. The fugitive ink is then removed to create functional channels in the extracellular matrix composition, at least a portion of the renal proximal tubule cells remaining along the first length of the one or more functional channels after removal of the first ink, at least a portion of the loop of Henley cells remaining in the second length of the one or more functional channels after removal of the second ink, and at least a portion of the renal distal tubule cells remaining in the third length of the one or more functional channels after removal of the third ink, thereby forming a nephron. In certain embodiments, continuous sacrificial filaments are deposited on and/or in a substrate through a single printhead.

To deposit sacrificial filaments that include a plurality of multiple cell types along their lengths through a single printhead a nozzle body comprising multiple ink delivery channels (e.g., a first ink delivery channel, a second ink delivery channel, a third ink delivery channel, etc.) in fluid communication with a nozzle outlet is used. The first ink formulation is forced to flow through the first ink delivery channel while preventing the second ink formulation and the third ink formulation from flowing through the second delivery channel and the third delivery channel, respectively, thereby extruding through the nozzle outlet the continuous sacrificial filament comprising the first ink formulation over the first predetermined length thereof. Once a sufficient first length of the continuous sacrificial filament comprising the first ink formulation is deposited, a withdrawal pulse is then applied to the first ink delivery channel while applying an infusion pulse to the second ink delivery channel, thereby forcing the second ink formulation to flow through the second ink delivery channel while preventing the first ink formulation and the third ink formulation from flowing through the first delivery channel and the third delivery channel, respectively, thereby extruding through the nozzle outlet the continuous sacrificial filament comprising the second ink formulation over the second predetermined length thereof. Once a sufficient second length of the continuous sacrificial filament comprising the second ink formulation is deposited, a withdrawal pulse is applied to the second ink delivery channel while applying an infusion pulse to the third ink delivery channel, thereby forcing the third ink formulation to flow through the third ink delivery channel while preventing the first ink formulation and the second ink formulation from flowing through the first delivery channel and the second delivery channel, respectively, thereby extruding through the nozzle outlet the continuous sacrificial filament comprising the third ink formulation over the third predetermined length thereof, thereby 3D printing the continuous sacrificial filaments comprising multiple cell types over different predetermined lengths of the filaments. In an alternative embodiment, the continuous sacrificial filaments can be deposited on and/or in a substrate through multiple printheads. The method of printing tissue constructs using multiple printheads was previously described in U.S. Pat. Pub. No. 2014/0314954, which is incorporated by reference in its entirety.

The second approach to generate tubular tissue constructs, such as nephrons, that include a plurality of multiple cell types along their lengths includes direct depositing specific "binding domains" or "ligands" for various target cells to be deposited in the tubular tissue construct. There are various types of binding domains or ligands that may be used to target specific cells for placement in a tubular tissue construct. Examples of specific binding domains or ligands include peptides, proteins, e.g., antibodies, small peptides, amino acids, DNA, RNA, aptamers, nanoparticles, small molecules, chemical functional groups, and/or bacteria.

In the context of this invention, a binding domain is a part of a molecule or structure with physico-chemical features or properties allowing the molecule or structure to bind with a site on a protein, a specific atom or molecule (i.e., "receptor") expressed by or associated with a predetermined type of target cells. A receptor is a chemical group or molecule (as a protein) on the surface or in the interior of a predetermined type of cells that has an affinity for a specific binding domain or ligand, such as a chemical group, molecule, bacteria, or virus. The receptor specifically binds, with high affinity, to its ligand.

All proteins bind to other molecules. The ability of a protein to bind to or interact with a ligand depends on the formation of weak, non-covalent bonds between them. This process relies on the sequence of amino acids in each protein and the way in which their side chains (or R groups) interact with each other. Different side chains can form different bonds. Because of this, protein interactions can be very specific. As such, proteins may be deposited as binding domains or ligands to bind to a site on a protein ("receptor") expressed or associated with a predetermined type of target cells via protein-protein interaction or binding. One example of proteins that may be deposited as binding domains includes antibodies.

Antibodies are "Y" shaped proteins that recognize and bind to other proteins (intracellular and extracellular proteins), called "antigens." Antigens, in the context of this invention, are differentiation molecules that are expressed by or associated with a predetermined type target cells. Antibodies display remarkable specificity for antigens. The antibody systems that may be used to bind target cells include antibodies that will bind directly with an antigen present on the target cell. Different types of cells express different combinations of antigens and/or differentiation molecules on their surface, and produce different intracellular and secretable proteins, which can be targeted by the antibodies. Specifically, each tip of the "Y" of an antibody contains a paratope that is specific for one particular epitope (similarly analogous to a key) on a differentiation molecule, allowing these two structures to bind together with precision. Using this binding mechanism, an antibody can identify or immobilize target cells. Antibodies for direct binding cells may be purchased directly from various antibody suppliers.

Receptors expressed by different types of cells can also bind to and interact with DNA or RNA. As such, in certain embodiments, DNA and/or RNA can function as binding domains. Helical DNA's backbone is made of sugar-phosphate-sugar linkages, where phosphates in di-ester groups have negative charges. Base pairs A-T and G-C in a specific sequence provide interactive surfaces in the major groove and less commonly in the minor groove. Though the N and O atoms are involved in base pairing to each other by hydrogen bonds, the other groups NH and O groups do provide atomic surfaces for the side chains of amino acids in proteins. Proteins have charged amino acids, which can bind to specific bases or to charged phosphates or to both. But the binding to phosphate group in the back bone is not sequence specific but just interactive charges. As such, in certain embodiments, DNA molecules can be deposited as binding domains for a predetermined type of cells. In certain alternative embodiments, RNA molecules can be deposited as binding domains for a predetermined type of cells.

A binding domain may also be a small molecule, such as a pharmaceutical drug, or parts of the outside of a virus or microbe.

The biding domains may also include chemical functional groups.

In certain embodiments, aptamers, which are oligonucleotide (DNA and RNA) or peptide molecules that bind to a specific target molecules expressed by or associated with a predetermined type of cells or even whole cells, may be used as binding domains for the predetermined type of cells. Aptamers are usually created by selecting them from a large random sequence pool. Aptamers show robust binding affinities (meaning that they discriminate for their specific targets with high precision—once they have determined their target, they then bind to it with a strong bond) for their various targets. One example of peptide aptamers includes affimers, which are small, highly stable proteins engineered to display peptide loops which provide a high affinity binding surface for a specific target protein/receptor, which in the context of this invention, are expressed by or associated with a predetermined type of cells.

Nanoparticles may also be used as binding domains for the predetermined type of cells. In some embodiments, nanoparticles can include coatings and/or can be linked to biological molecules that can act as binding domains (such as monoclonal antibodies, aptamers, streptavidin or peptides) to allow for cell binding. Multivalent nanoparticles, bearing multiple targeting groups, can cluster receptors, which can give stronger anchoring. As such, in certain embodiments, cell-targeting nanoparticles that include ligands (coated on or attached to the outsides of nanoparticles) may be used as binding domains for a predetermined type of cells. These ligands are special in that they can recognize and bind to complementary molecules, or receptors, found on the surface of cells.

In certain further embodiments, the extracellular matrix surrounding the patterned sacrificial filaments may include predetermined coupling moieties to capture the binding domains from the sacrificial filament. The coupling moieties are chemically reactive to the binding domains, thereby locally capturing said binding domains upon contact before, during, or subsequent to the evacuation of the sacrificial filament. The coupling moieties comprise native extracellular matrix binding domains, antibodies, peptides, proteins, DNA, RNA, aptamers, nanoparticles, small molecules, chemical functional groups, and bacteria.

As mentioned previously, the second approach to generate tubular tissue constructs, such as nephrons, includes depositing one or more sacrificial filaments on and/or in a substrate to form a functional channel pattern, each sacrificial filament comprising a fugitive ink and a plurality of predetermined types of binding domains. The various types of binding domains were described in detail above. Each of the predetermined type of binding domain is deposited at a different predetermined location along a length of the sacrificial filament and is capable of binding to a predetermined type of target cell. The functional channel pattern can then be surrounded (partially or wholly) with an extracellular matrix composition (as described in detail above). In certain embodiments, the functional channel pattern can be surrounded with the extracellular matrix composition during deposition of the one or more sacrificial filaments, the one or more functional channel patterns thereby being formed and embedded simultaneously in the extracellular matrix composition. Once the extracellular matrix composition is in place, the fugitive ink can be removed to create one or more functional channels in the extracellular matrix composition. It is important that at least a portion of the different predetermined types of binding domains remains at the different predetermined locations after removal of the fugitive ink. Next, a suspension comprising at least one predetermined type of target cells can be injected into the functional channel. The target cells will bind to corresponding predetermined types of binding domains, thereby forming a tubular tissue construct, such as a nephron. In certain embodiments, the suspension can include multiple (3 or more) predetermined types of target cells. The cells may be individual cell lines normally present in the tubular organ or a portion of the tubular organ to be printed and/or iPSC-derived cells. As discussed in detail above, the binding domains for the target cells can be proteins, e.g., antibodies; DNA; RNA; aptamers; nanoparticles; bacteria; or any other suitable binding domain, or a combination thereof.

In certain embodiments, to create a vascular pattern interpenetrating the functional channel pattern, sacrificial filaments can be deposited on and/or in the substrate, where each of the sacrificial filaments comprises a second fugitive ink. Next, the second fugitive ink can be removed to create vascular channels in the extracellular matrix composition, thereby forming an interpenetrating vascular network in the tubular tissue construct, such as a nephron. A suspension of viable epithelial cells may be injected into the vascular channels. In certain embodiments, wherein the at least partial surrounding of the functional channel pattern with the extracellular matrix composition occurs during deposition of the sacrificial filaments, the functional channel patterns can be thereby formed and embedded simultaneously in the extracellular matrix composition. In certain embodiments, cell-laden filaments each comprising a plurality of viable cells may also be deposited on and/or in the substrate to form tissue patterns, where each of the tissue patterns includes one or more predetermined cell types.

To print a nephron using an approach that utilizes binding domains, one or more continuous sacrificial filaments are deposited on and/or in a substrate to form a functional channel, where each sacrificial filament includes: a first fugitive ink formulation over a first length of the sacrificial filament, a second ink formulation over a second length of the sacrificial filament, and a third ink formulation over a third length of the sacrificial filament. The first fugitive ink formulation includes, for example, a fugitive ink and a first predetermined type of binding domains to target a first types of cells, e.g., renal proximal tubule cells. The second fugitive ink formulation includes, for example, the fugitive ink and a second predetermined type of binding domains to target a second type of cells, e.g., loop of Henle cells. The third fugitive ink formulation includes, for example, the fugitive ink and a third predetermined type of binding domains to target a third type of cells, e.g., renal distal tubule cells. Next, the functional channel pattern is at least partially (or wholly) surrounded with an extracellular matrix composition. The fugitive ink is then removed to create functional channels in the extracellular matrix composition. At least a portion of the first predetermined type of binding domains remains along the first length of the one or more functional channels after removal of the ink. At least a portion of the second predetermined type of binding domains remains in the second length of the one or more functional channels after removal of the ink. At least a portion of the third predetermined type of binding domains remains in the third length of the one or more functional channels after removal of the ink. Next, a suspension comprising at least one type of predetermined cells, such as renal proximal tubule cells, loop of Henle cells and renal distal tubule cells, collecting duct cells, fenestrated glomerular endothelial cells is injected into the functional channel, wherein the cells bind to their corresponding predetermined binding domains, thereby forming a nephron. In certain embodiments, the suspension includes some or all of the predetermined types of cells. The binding domains may be peptides proteins, e.g., antibodies; DNA; RNA; aptamers; nanoparticles; small molecules, chemical functional groups, bacteria or any other suitable binding domain, or a combination thereof.

Also, sacrificial filaments comprising a second fugitive ink can be deposited on and/or in the substrate to form a vascular pattern interpenetrating the functional channel pattern. The second fugitive ink may then be removed to create vascular channels in the extracellular matrix composition, thereby forming an interpenetrating vascular network in the tubular tissue construct. A suspension of viable epithelial cells can be injected into the vascular channels. A single printhead or multiple printheads may be used to deposit continuous sacrificial filaments on and/or in a substrate.

In another approach of printing a tubular tissue construct, cell-laden filaments, each including a plurality of predetermined types of viable cells, can be deposited on and/or in a substrate to form tissue patterns. Each of the tissue patterns includes at least two predetermined cell types, wherein each predetermined type of viable cells is deposited at a different predetermined location along a length of the cell-laden filament. The predetermined cell types can be any cells described herein, including kidney cells (e.g., renal proximal tubule cells, loop of Henle cells and renal distal tubule cells, collecting duct cells, fenestrated glomerular endothelial cells) and/or iPSC-derived patient-specific pro-kidney or patient-specific cell lines. The sacrificial filaments including a fugitive ink can also be deposited on and/or in the substrate to form a functional channel pattern interpenetrating the tissue patterns. Next, the tissue patterns and the functional channel pattern can be at least partially or wholly surrounded with an extracellular matrix composition and the fugitive ink can be removed to create functional channels in the extracellular matrix composition, thereby forming an interpenetrating channel network in a tissue construct. In certain embodiments, the cell-laden filaments may also include an extracellular matrix material. The extracellular matrix material can include gelatin, fibrin, gelatin methacrylate, collagen I, collagen III, collagen IV, fibrinogen, matrigel, laminin, carbopol, N-isopropylacrylamide, polyethylene glycol, gelatin methacrylate, polyhydroxyethylmethacrylate, silk, hyaluronic acid, and/or combinations thereof. The cell-laden filaments may also include functional chemical substances selected from the group consisting of: drugs, small molecules, toxins, proteins, and hormones. In certain embodiments, the sacrificial filaments including a second fugitive ink can be deposited on and/or in the substrate to form a vascular pattern interpenetrating the functional channel pattern, and the second fugitive ink can be removed to create vascular channels in the extracellular matrix composition, thereby forming an interpenetrating vascular network in the tubular tissue construct. A suspension of viable epithelial cells can be injected into the vascular channels. The tissue construct may be a nephron, and the plurality of predetermined types of viable cells can include renal proximal tubule cells, loop of Henle cells, renal distal tubule cells, collecting duct cells, fenestrated glomerular endothelial cells, iPSCs, and/or iPSCs-derived patient-specific pro-kidney or individual cells lines present in a nephron. In certain other embodiments, the tubular tissue construct may be intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph.

Additional embodiments contemplate integrating (by 3D printing) lymphatics and nerves to improve physiology of the 3D printed tubular structures, such as nephrons.

Figure 17G:
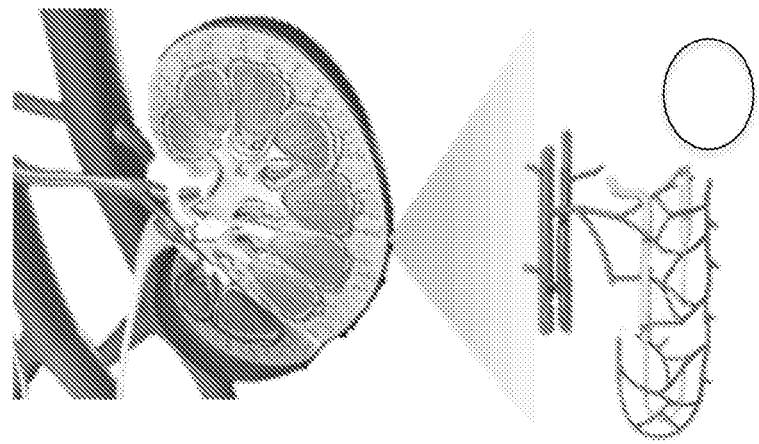
FIGS. 17G-I show the renal proximal tubule (circled in black) with epithelial cells (FIG. 17G). Printing of a convoluted path to make the proximal tubule is shown in FIG. 17H and a close up view of a typical epithelialized tubule is shown stained for nuclei (blue) and ATPase (green) is shown in FIG. 17I.
Figure 17H:
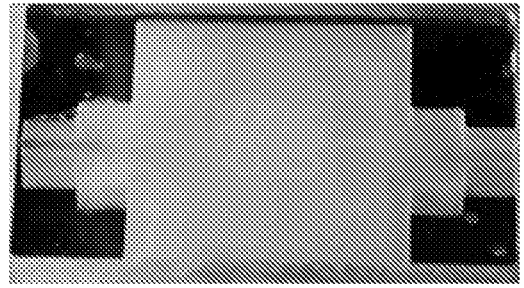
Figure 17I:
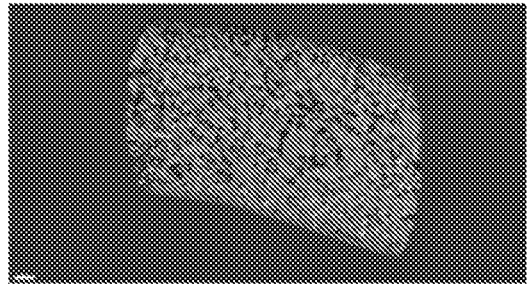

As shown in FIGS. 17G-I, the ability to epithelialize is demonstrated using the renal proximal tubule (FIG. 17G; circled in black). Printing of a convoluted path to make the proximal tubule is shown below (FIG. 17H; bottom left) and a close up view of a typical epithelialized tubule is shown stained for nuclei (blue) and ATPase (green) (FIG. 17I).

FIGS. 17J-N show proximal tubule epithelial cells (PTECs) stained using immunofluorescence for several functional properties on a 2D dish (AQPI, ATPase, Cilia, ZO-I) and the presence of domes in culture.

FIGS. 17O-T show perfused tubule constructs stained using immunofluorescence for several functional properties on a 2D dish (AQPI, ATPase, Cilia, ZO-I). The properties were retained or enhanced in the perfused tubule constructs.

FIGS. 17 U-X show SEM and TEM images of the tubules highlighting the confluent nature of the cells in the constructs, primary cilia, and formation of a brush border.

EXAMPLES

Example 1

Fugitive Ink

Figures 6A, 6B, 6C, 6D, 6E, 6F:
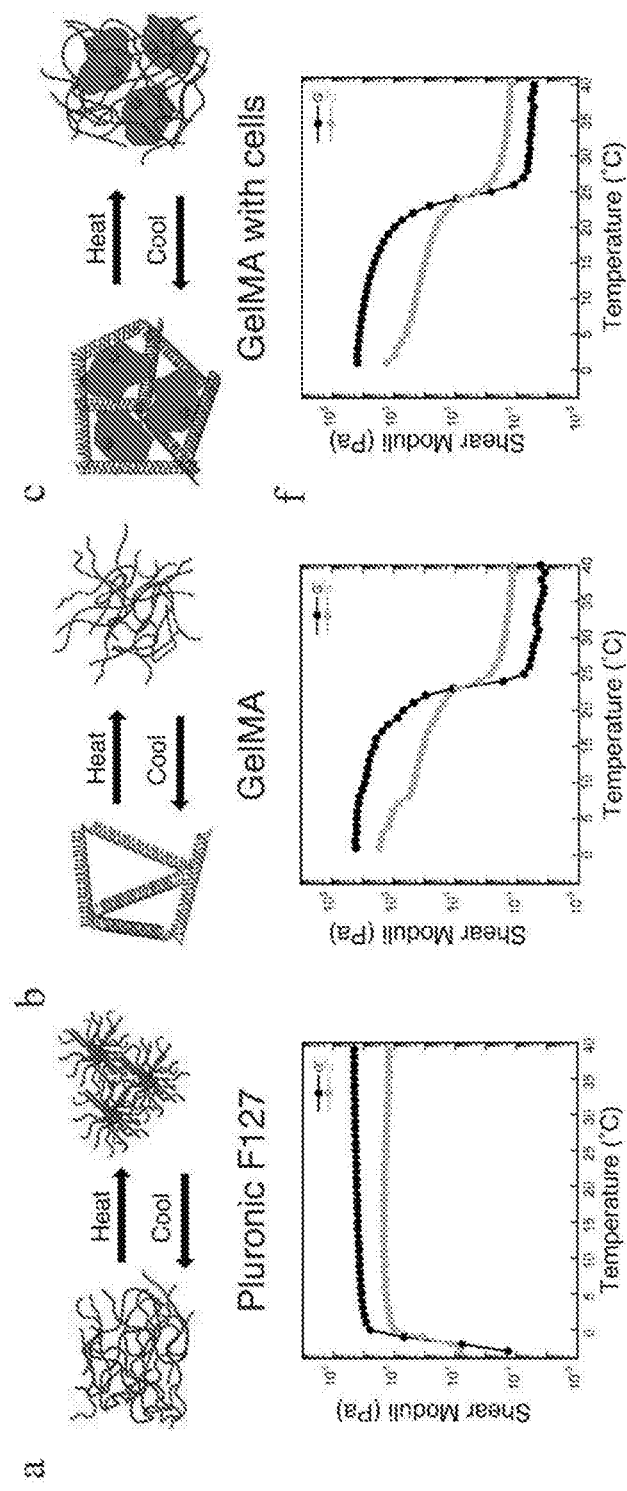
FIG. 6A shows a schematic of the sol-gel transition of Pluronic F127.
FIG. 6B shows the temperature dependence on the shear moduli (G' and G") of 40 wt. % Pluronic F127 ink.
FIG. 6C shows a schematic of the helix-to-coil transition characteristic of GelMA.
FIG. 6D shows the thermal dependence of GelMA shear moduli.
FIG. 6E shows GelMA laden with cells.
FIG. 6F shows the shear moduli as function of temperature for GelMA laden with 10T1/2 fibroblast cells.

Referring to FIG. 6A, highly concentrated (40 wt. %) Pluronic F127A, which exhibits a strong shear-thinning response when the applied shear stress exceeds the shear yield stress ($\tau_y$) (e.g., during printing), as well as a plateau shear elastic modulus (G') that exceeds the shear viscous modulus (G") when the applied shear stress is below $\tau_y$ (e.g., after printing), is selected as the fugitive ink for an exemplary system. The fugitive ink elasticity is found to be about $2 \times 10^4$ Pa at 22° C., as shown in FIG. 6B. Below the CMT (about 4° C.), the ink liquefies and its elasticity decreases by several orders of magnitude, thereby facilitating its removal from the tissue construct.

As described above, the sacrificial filaments formed from the fugitive ink may include one or more additional cells, growth factors, drugs, etc. For example, endothelial, epithelial and/or other cells may be dispersed within the fugitive ink and deposited with the sacrificial filaments. When the fugitive ink is removed to form the vascular (or other) channels, the cells may remain, lining walls of the channels.

Figure 16G:
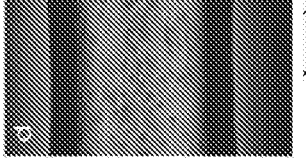
FIG. 16G shows the vascular network after active perfusion for 24 hours.

This approach is demonstrated with a highly concentrated endothelial cell-laden fugitive (pluronic) ink ($1 \times 10^7$ cells/ml). The fugitive ink is deposited and encapsulated with an extracellular matrix composition. Upon removal of the fugitive ink to form vascular channels, the endothelial cells remain affixed to walls of the channels, as shown schematically in FIGS. 16A-16C and experimentally in FIGS. 16D-16G. FIG. 16G shows a simple channel created using this approach that has been perfused for over 24 hours. The endothelial cells appear to line the channel and look qualitatively similar to those created using a conventional seeding approach. This technique provides an alternative to seeding existing vascular channels with endothelial cells, particularly in the case of highly branched vascular networks where cells may clog and inhibit flow, leading to non-uniform seeding.

Extracellular Matrix Composition and Material

As set forth above, an interpenetrating polymer network based on gelatin and fibrin has been developed that mimics natural ECM, and which may be used for the extracellular matrix composition and/or the extracellular matrix material of the tissue construct.

FIGS. 13A-13D show fabrication of a gelatin-fibrin interpenetrating polymer network, or gelatin-fibrin matrix. First, the gel precursors are first mixed together. Polymerizing fibrinogen via the enzyme thrombin forms a fibrin gel or network. This phase provides initial mechanical strength and rigidity, as indicated by an increase in shear elastic modulus. The second phase (gelatin) is then formed around the fibrin gel, and the two phases are slowly crosslinked together via transglutaminase (TG). FIGS. 13E and 13F show shear modulus versus time (G' and G") and a stress-strain curve for the gelatin-fibrin interpentrating polymer network.

Figure 14:
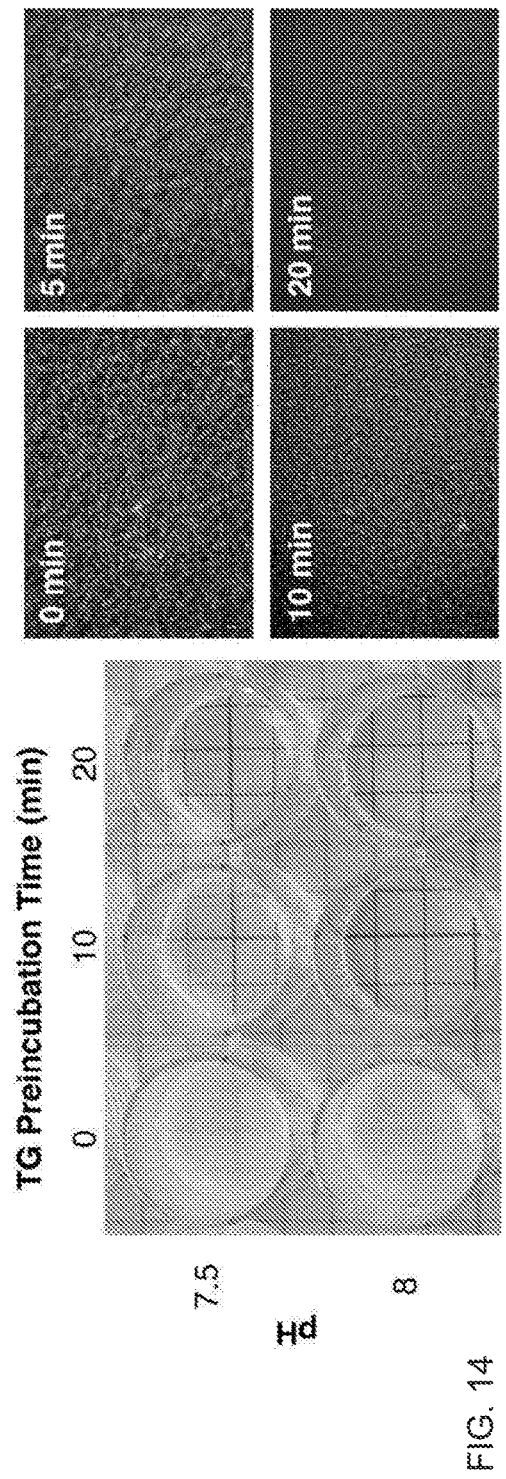
FIG. 14 illustrates the influence of TG incubation time on the optical properties of the fibrin-gelatin interpenetrating polymer network. Transparency is determined by the final pore architecture of the fibrin gel, which is visualized using a rhodamine tagged fibrinogen and confocal microscopy.

TG is a naturally occurring enzymatic protein crosslinker with myriad biological functions; for example, it may be up-regulated during wound healing in vivo. By varying TG incubation time, the optical properties (e.g., transparency) of the fibrin gel can be tailored. The transparency is dictated by the final pore architecture of the fibrin gel, which is visualized using a rhodamine-tagged fibrinogen and confocal microscopy. It is also of interest to determine if TG and gelatin disrupt natural fibrin polymerization. Confocal microscopy images reveal that the fibrillar nature of fibrin is preserved and can be precisely tuned by varying different processing conditions, such as incubation time, as illustrated in FIG. 14. A longer fibrin-TG incubation time leads to a more dense fibrillar network and, subsequently, higher optical transparency.

Besides fabrication considerations, cell material-interactions play an important role in materials selection. The gelatin-fibrin matrix has been shown to be compatible with many different cell types, including fibroblasts (connective tissue), smooth muscle cells, endothelial cells, and renal proximal tubule cells (epithelial). The adhesivity of the gelatin-fibrin matrix has been quantified by comparing the projected area of cells on various substrates. The gelatin-fibrin matrix outperformed all other materials including native fibrin, tissue culture polystyrene (TCPS), and gelatin methacrylate (GelMa). FIGS. 13G-13I show various cells essential for creating blood vessels—fibroblasts, endothelial cells, and smooth muscle cells—on an exemplary gelatin-fibrin matrix surface. To highlight the diversity of the adhesivity, tissue-specific epithelial cells were grown on the surface, as illustrated in FIG. 13J.

In a second example, gelatin methacrylate (GelMA), which is biocompatible, easily processed and inexpensive, is selected for use as both the extracellular matrix material for the cell-laden formulation and as the extracellular matrix composition for the encapsulation step. GelMA is denatured collagen that is modified with photopolymerizable methacrylate (MA) groups, which allows the matrix to be covalently cross-linked by UV light after printing. Physical gelation arises from the assembly of intermolecular triple helices that possess a structure similar to collagen, as illustrated in FIG. 6C. By varying the concentration, degree of methacrylation, and temperature, the shear yield stress and elastic modulus of aqueous GelMA systems can be systematically tuned.

The extracellular matrix composition is produced by dissolving 15 wt. % GelMA in cell culture media. Above approximately 25° C., the composition is a low viscosity fluid with a G' value below $10^{-1}$ Pa. Upon cooling below 25° C., the composition undergoes gelation, yielding a clear, viscoelastic extracellular matrix material. The elasticity of the extracellular matrix composition increases with decreasing temperature, with G' values of about $10^3$ Pa and $2 \times 10^4$ Pa observed at 22° C. and 2° C. (FIG. 6D), which correspond to typical conditions for printing and fugitive ink removal, respectively.

The same aqueous GelMA composition is used to create cell-laden inks that contain viable cells for printing. Prior studies have shown that cells adhere, remodel, and migrate through GelMA due to the presence of integrin-binding motifs and matrix metal-proteinase sensitive groups. It is found that the incorporation of a moderate concentration, e.g., $2 \times 10^6$ cells/mL, of 10T1/2 fibroblast cells into the 15 wt. % GelMA ink (FIGS. 6E and 6F) does not significantly alter the temperature at which gelation ensues or the elasticity of the composition over the temperature range of interest, e.g., 2° C. to 40° C. Hence, both pure and cell-laden GelMA inks can be printed and further processed, as needed, in the same manner.

The differences in thermally reversible gelation observed for the fugitive Pluronic F127, pure GelMA, and cell-laden GelMA inks give rise to three distinct processing windows. Between approximately 4° C. and 25° C., each ink is stiff and exhibits a solid-like response, where G'>G". At T≥25° C., the Pluronic F127 fugitive ink is stiff and solid-like (G'>G"), while the pure and cell-laden GelMA inks are liquids that flow readily. Below about 4° C., the Pluronic F127 fugitive ink is a liquid that flows readily, while the pure and cell-laden GelMA inks are stiff and solid-like (G'>G").

Printing of Vascular Patterns

Figures 7A, 7B, 7C, 7D, 7E, 7F, 7G, 7H, 7I, 7J, 7K:
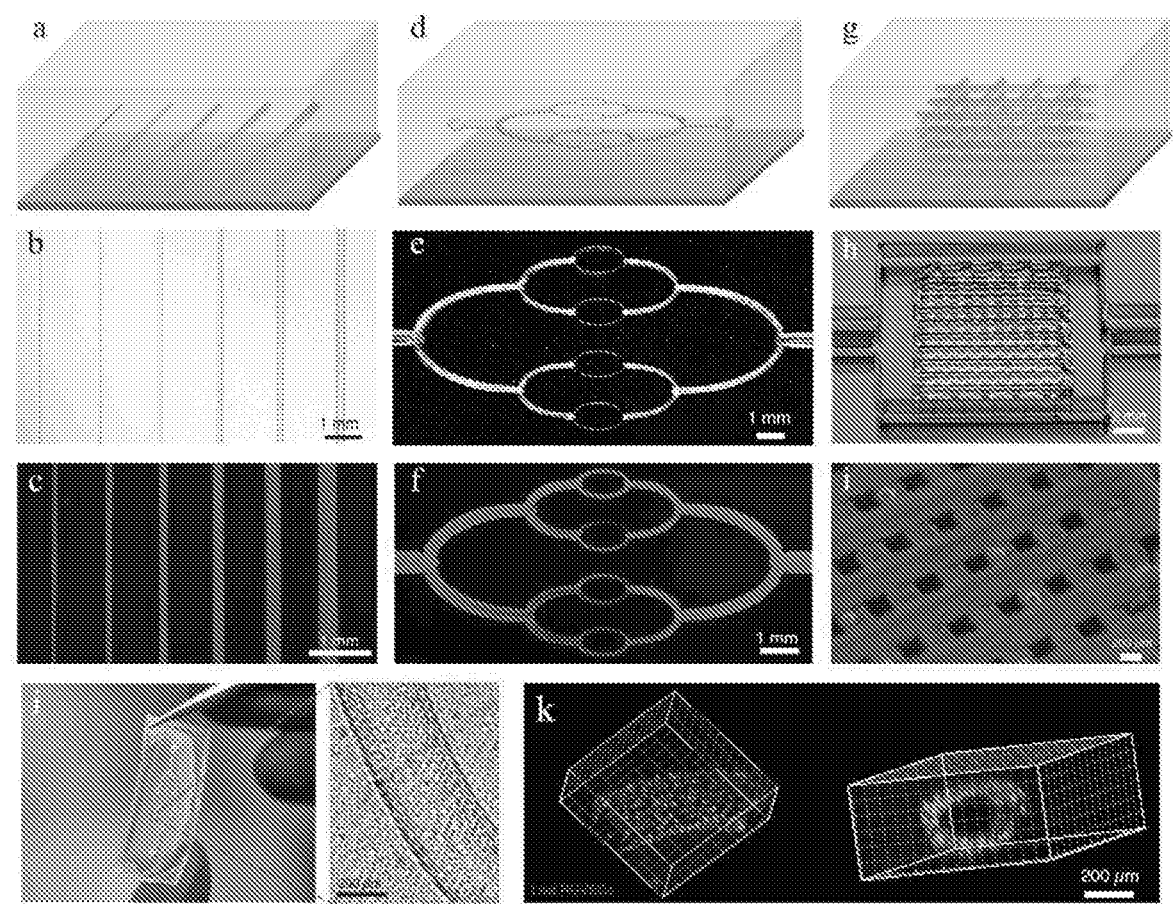
FIGS. 7A and 7B show 1D channels formed in GelMA, where diameters range from 115 μm to 500 μm.
FIG. 7C shows the channels perfused with a water-soluble fluorescent dye for visualization.
FIGS. 7D-7E show a 2D hierarchical branching network with curvilinear filaments printed using a single 30 μm glass capillary.
FIG. 7F shows the structure perfused with red fluorescent dye for visualization.
FIGS. 7G-7I show a highly periodic 3D lattice printed from sacrificial filaments to create a 3D vascular pattern that can be perfused after evacuation of the fugitive ink.
FIG. 7J shows an optical image of representative microchannel within a 2D vascular network perfused with a HUVEC suspension.
FIG. 7K shows a confocal image of the microchannel shown in FIG. 7J with live HUVEC cells lining the microchannel walls.

The complimentary thermal behavior described above for the Pluronic F127-GelMA system is exploited to print representative vascular patterns comprising a plurality of sacrificial filaments which are then encapsulated in an acellular extracellular matrix composition (pure GelMA). FIGS. 7A-7K illustrate the formation of 1D, 2D and 3D vascular networks and endothelialization of the channels, with schematic views and corresponding optical images of each vascular network design. After removing the fugitive ink, each vascular network is perfused with a fluorescent red dye to aid in visualization (FIGS. 7C, 7F and 7I). Within each tissue construct, the diameter of the sacrificial filaments can be altered as desired by modifying the printing pressure, speed, and/or nozzle height. For example, I-D microchannel arrays with diameters increasing from 45 µm to 500 µm are printed using a single 30 µm nozzle simply by increasing the printing pressure and nozzle height in a stepwise fashion between each printed feature (FIGS. 7A-7B).

Figures 8A, 8B:
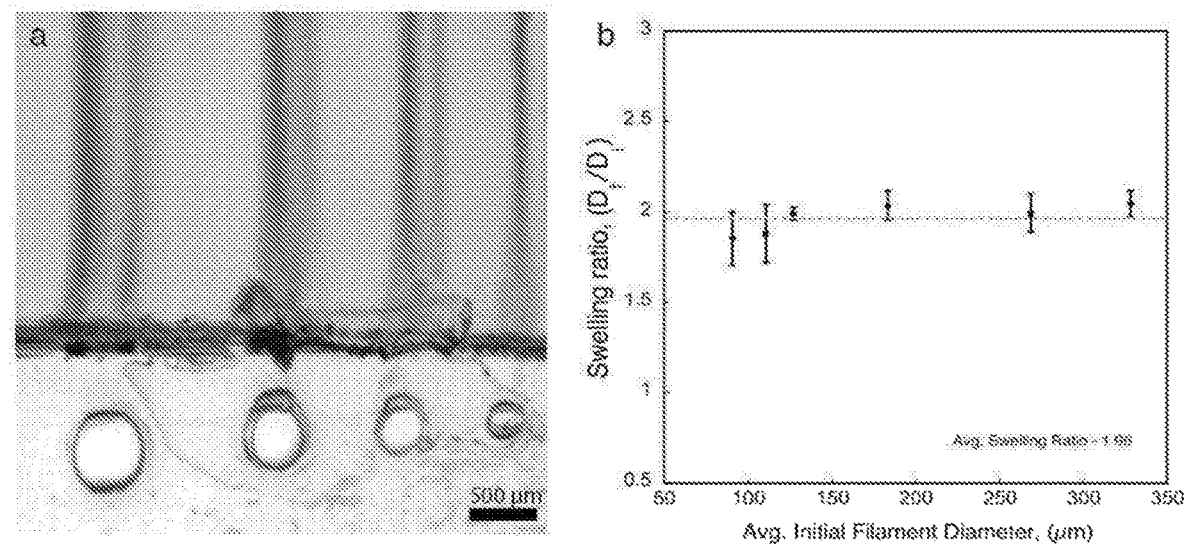
FIG. 8A shows representative cross-sections of various channel diameters created by depositing sacrificial filaments and removing the fugitive ink.
FIG. 8B is a plot showing the swelling ratio ($D_{FINAL}/D_{initial}$) of various printed sacrificial filaments comprising Pluronic F127. Each data point is an average of six samples, each deposited at a fixed speed, pressure, and nozzle height (z axis). The diameters are measured directly after printing and again after evacuation via top-down optical microscopy.
Figures 9A, 9B, 9C, 9D:
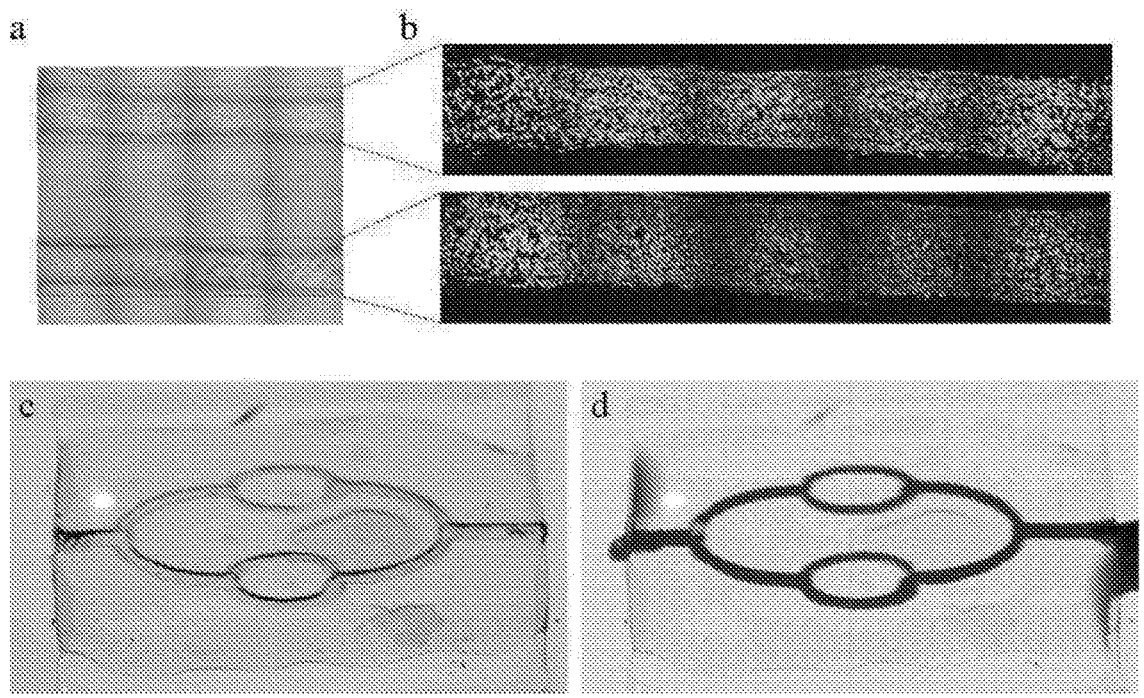
FIGS. 9A-9B show that endothelialized vascular channels can be created in fibrin gel, as shown.
FIGS. 9C and 9D show before and after photographs of animal blood infiltration in a fabricated bifurcating vascular network.

After photopolymerizing the GelMA matrix, the fugitive ink is removed by cooling the printed constructs below 4° C., yielding open I-D microchannels. Representative cross-sectional images of these I-D channels, shown in FIG. 8A, reveal that their final diameters range from about 100 µm to about 1 mm. Since the GelMA ink has a higher water content than the fugitive ink, the printed vascular features may swell as water diffuses into the fugitive ink (Pluronic F127) from the surrounding matrix. Indeed, the diameters nearly double in size, with a swelling ratio that is independent of initial microchannel diameter (FIG. 8B) for this material system.

The 2-D vascular network design mimics the hierarchical, bifurcating motifs found in biological systems, large channels bifurcate to form smaller channels that maximize efficient blood flow, nutrient transport, and waste removal while minimizing the metabolic cost. These 2D hierarchical vascular networks are printed using a single nozzle of 30 microns (e.g., FIGS. 7E and 7F). The as-printed, largest channels (650 µm in diameter) provide a single inlet and outlet for perfusion, while the smallest channels (45 µm) in diameter) reduce the characteristic diffusion distance between adjacent conduits. Finally, a 3D microvascular network design, which is shown in FIGS. 7G, 7H and 7I and includes a 3D periodic array of uniform microchannels, is printed. Because the embedded microchannels are interconnected in all three dimensions, the fugitive ink can be removed from the surrounding GelMA matrix quickly and with high fidelity.

Seeding of Vascular Channels

Multiple types of fluids may be flowed through embedded vascular networks to demonstrate their perfusable nature. For example, the 2D hierarchical bifurcating networks are injected with a human umbilical vein endothelial cell (HUVEC) suspension followed by gentle rocking. After 48 h, it is found that the cells retained greater than 95% viability and assembled into a nearly confluent layer, as determined by live/dead staining coupled with confocal imaging within a representative, bifurcated microchannel.

Figure 18A:
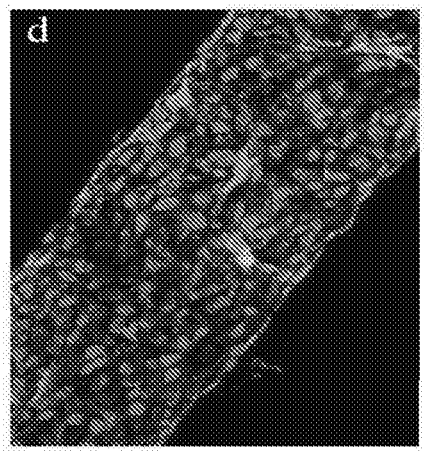
FIGS. 18A-18C highlight the initially uniform distribution of HUVECs (red) and HNDFs (green) at 3 days post-seeding.
Figure 18B:
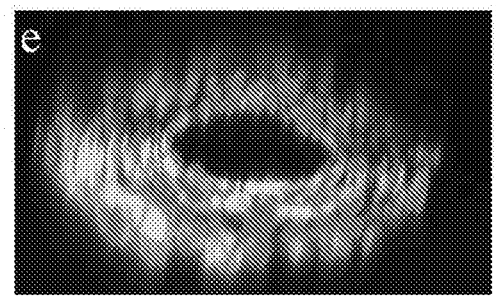
Figure 18C:
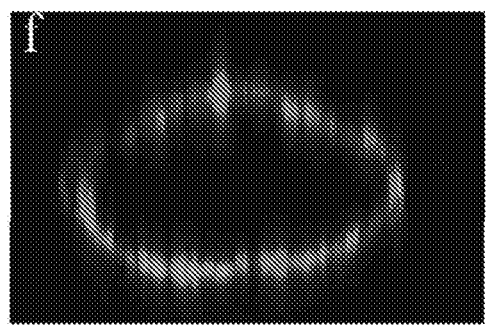
Figure 18D:
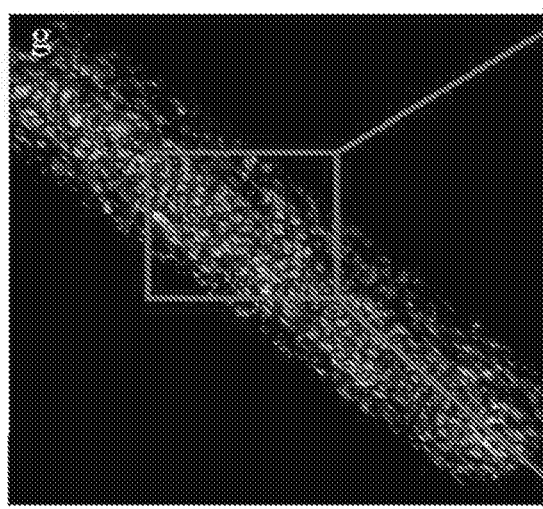
FIGS. 18D-18E shows the same channel after eight days, at which time the channel comprises a distinct outer stromal (HNDF) layer and a confluent endothelial (HUVEC) layer.
Figure 18E:
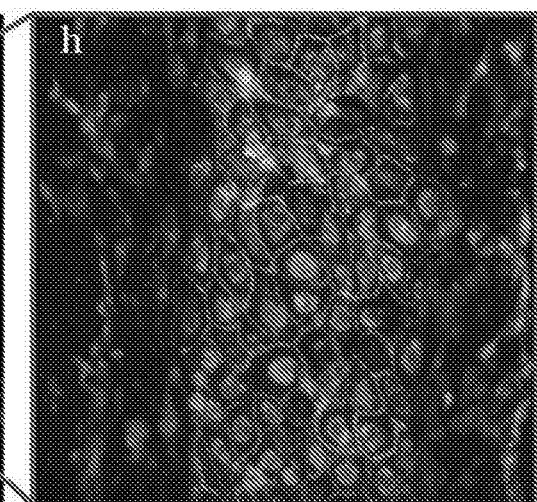

The vascular channels may be seeded with multiple cell types, such as fibroblasts or smooth muscle cells in addition to HUVECs. Here, fibroblasts are co-seeded with HUVECs. It is found that, after about one week of perfusion culture, uniformly co-seeded endothelial cells and fibroblasts self assemble into two distinct layers of outer enveloping stroma (human dermal fibroblasts; HNDFs) and confluent inner endothelium (HUVECs). FIGS. 18A-18C highlight the initially uniform distribution of HUVECs (red) and HNDFs (green) at 3 days post-seeding. FIGS. 18D-18E shows the same channel after eight days, at which time the channel comprises a distinct outer stromal (HNDF) layer and a confluent endothelial (HUVEC) layer. The confluent endothelium is visualized using immunohistochemistry to stain for vascular endothelial cadherin (VE-Cad), an endothelial-specific junction protein expressed when cells form confluent networks (shown in magenta).

To further promote the attachment and proliferation of the endothelial cells along the fabricated channel walls, the interior of the walls may be coated by perfusing a fibronectin solution through the channels prior to introducing the HUVEC suspension, as shown in FIGS. 9A-9D. Also, when animal blood is directly injected into the inlet of the 2-D vascular network it rapidly flows through the entire network to outlet. These initial demonstrations illustrate the potential to create perfusable vasculature of nearly any arbitrary design.

Printing of Cell-Laden Filaments Including More than One Cell Type

Figure 20A:
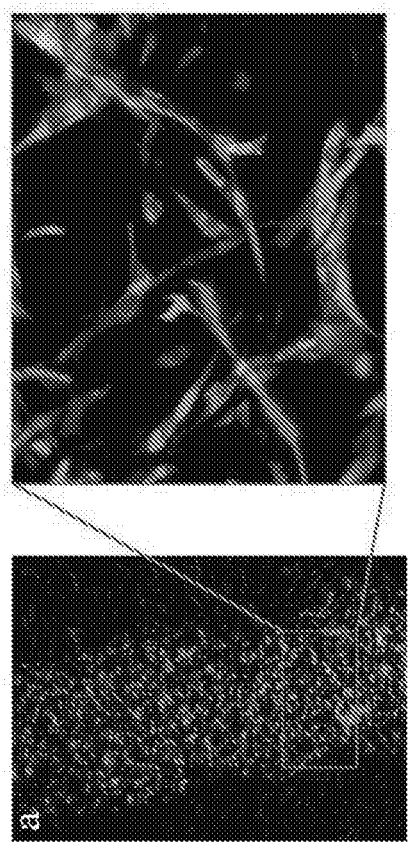
FIGS. 20A-20C are confocal microscopy images that show spontaneous neovasculature formation in a printed cell-laden filament comprising two cell types (HNDFs and HUVECs dispersed within a gelatin-fibrin extracellular matrix material).
Figure 20B:
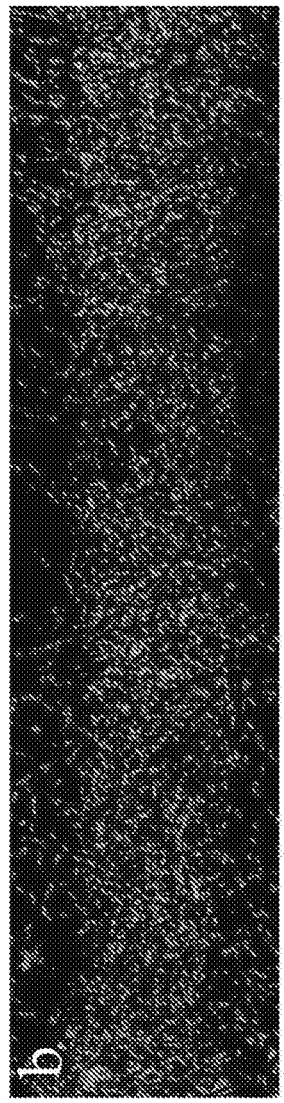
Figure 20C:
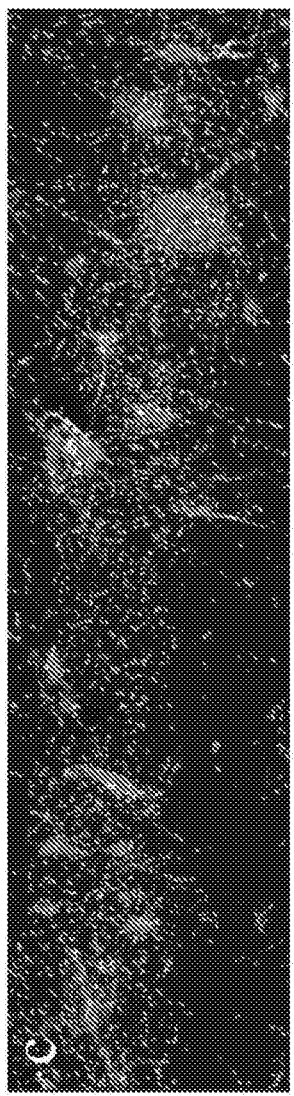

The printing of cell co-culture inks that allow the delivery of two or more cell types within a single ink filament is demonstrated. It is observed that a cell-laden ink including, in this example, a dispersion of HNDFs and HUVECs in a gelatin-fibrin matrix material, leads to spontaneous neovasculature formation in the printed filament, as evidenced in FIGS. 20A-20C. This is not observed in printed filaments based on a monoculture of HUVECs. This approach suggests cell-laden filaments comprising more than one cell type, including tissue-specific cell types (e.g., hepatocytes, islets, podocytes, neurons, etc.) or stem cells (e.g., iPSCs, MSCs, etc.), may be used to achieve desired heterogeneity and also to enhance function.

Printing of Fugitive Ink onto a Cell-Laden Matrix

As in the previous example, HNDFs and HUVECs are dispersed within an extracellular matrix composition (specifically, a gelatin-fibrin matrix material) to form a cell-laden matrix. A fugitive ink is printed directly onto the cell-laden matrix and then encapsulated by the gelatin-fibrin matrix material. The fugitive ink is evacuated to form vascular channels, and the vascular channels are seeded with HUVECs. Over time, it is found that the HUVECs assemble into capillary structures within the printed cell-laden filament. FIGS. 19A-19D show that the endothelial cells become attached to the vascular channels and form confluent layers, and FIGS. 19E-19F show evidence of angiogenic sprouting of small capillaries from the confluent blood vessels indicating that the process is conducive to cellular remodeling and higher-level biological processes.

Two effects are hypothesized to contribute to this observed behavior. First, fibroblasts have been shown numerous times to be pro-angiogenic support cells in vitro through specific chemical cues such as fibroblast growth factor (FGF), often leading to neovascularization processes. Additionally, the concentrated population of proliferative cells within the matrix has extensive metabolic requirements that are likely not met by diffusion alone. It is widely accepted that cells that are not within a few 100 microns of blood vessel will become oxygen stressed and eventually necrotic. In vivo, the recruitment of host vasculature into avascular structures to prevent necrosis has been observed.

Printing of Tissue Constructs Including Interpenetrating Vasculature

To demonstrate the fabrication of tissue constructs replete with blood vessels, multiple types of cells, and an extracellular matrix composition, 3D heterogeneous structures of varying design are printed.

The first structure is composed of semi-woven features printed in and out of plane (FIGS. 10A-10G). This four-layer tissue construct includes two tissue patterns each comprising a different cell type and a vascular pattern formed from sacrificial filaments comprising a fugitive ink. The tissue construct is produced in a layer by layer build sequence by printing four inks: PDMS, fugitive Pluronic F127 and two different cell-laden GelMA inks, followed by depositing pure GelMA ink at 37° C. to fully encapsulate the printed features, and finally photopolymerization to cross-link the GelMA matrix. This 3D architecture was conceived and fabricated to demonstrate the printing capabilities and also facilitate confocal imaging through the entire 4-layer, printed construct.

Figures 10A, 10B, 10C, 10D, 10E, 10F, 10G:
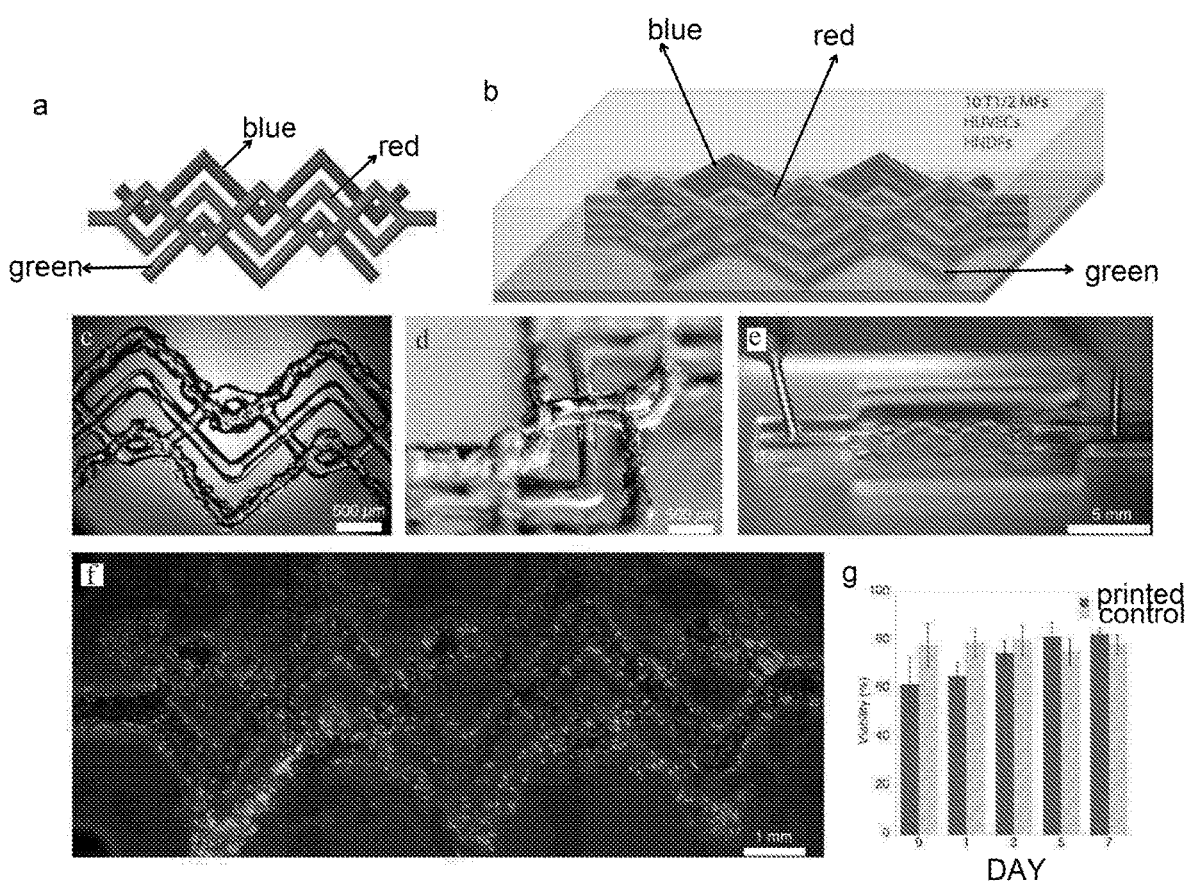
FIG. 10A provides a top-down view of a final 3D printed heterogeneous tissue constructs structure that is printed from four separate inks.
FIG. 10B provides an angled view of the complex toolpath used to create the tissue construct shown in FIG. 10A, where the green filaments comprise GFP HNDF-laden GelMA, the blue filaments comprise 10T1/2 fibroblast-laden GelMA, and the red filaments comprise the Pluronic ink that may be endothelialized with RFP HUVECs. The gray shaded region corresponds to pure GelMA matrix that encapsulates the 3D printed construct.
FIG. 10C is a bright field microscopy image overlaid with the green fluorescent channel of the structure of FIG. 10A directly after printing.
FIG. 10D is a photograph illustrating the spanning and out-of-plane nature of the printed structure.
FIG. 10E shows a demonstration of the fugitive ink evacuation process.
FIG. 10F provides a composite image of the three fluorescent channels: 10T1/2 fibroblasts (blue), HNDFs (green), HUVECs (red) from the structure of FIG. 10A.
FIG. 10G shows cell-viability assay results of printed 10T1/2 fibroblasts compared with a non-printed control.
Figures 11A, 11B, 11C:
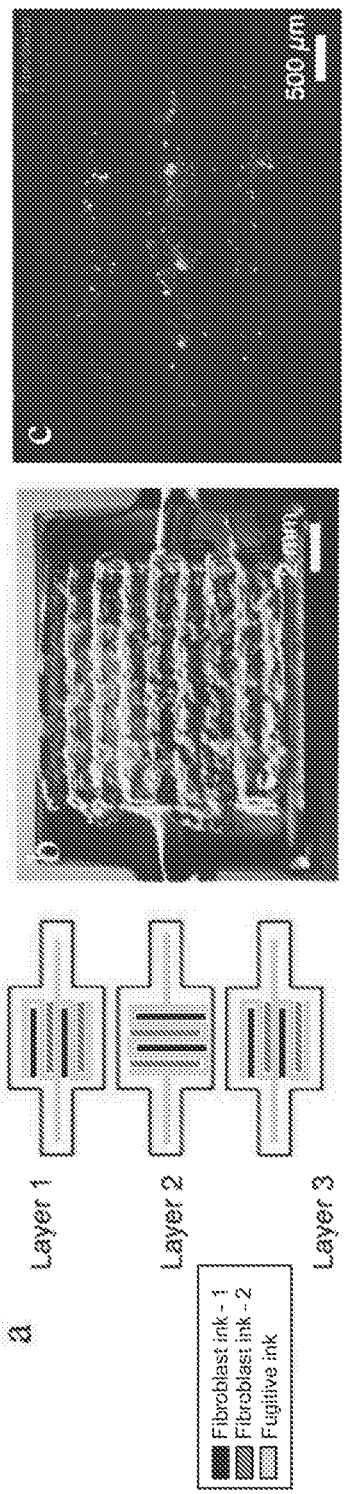
FIG. 11A shows a schematic of a three-layered structure containing multiple cell-laden filaments and sacrificial filaments comprising a fugitive ink.
FIG. 11B shows a photograph of the evacuated microstructure before endothelialization.
FIG. 11C shows an epifluorescent image of GFP HNDFs (green) and RFP HUVECs (red) after two days in culture.

As indicated previously, the PDMS ink is first printed in the form of a high-aspect ratio border that surrounds each tissue construct and serves as a mold for the pure GelMA ink used for the encapsulation step. The fugitive ink and both cell-laden GelMA inks, which contain either green fluorescent protein expressing human neonatal dermal fibroblasts (HNDFs) or non-fluorescent 10T1/2s, an established mouse fibroblast line, are co-printed at concentrations of $2 \times 10^6$ cells/mL through 200 μm nozzles in a predefined sequential process. FIG. 10C shows an image of the 3D structure directly after printing. Only the green fluorescent channel is overlaid onto the bright field image so that the printed cell channel can be easily visualized. After fabrication, the fugitive ink is liquefied and removed from the 3D construct. The evacuation procedure involves placing empty syringe tips into the inlet and outlet microchannels and then suctioning out the entire vascular network under a modest vacuum. The removal process is rapid and yields a high fidelity, interpenetrating vasculature, which is then endothelialized as described above.

Characterization of the Tissue Constructs

Using microscopy, the locations of the three cell types that are independently stained (green-GFP HNDFs, blue-10T1/2, and red-HUVECs) are identified. The semi-woven nature of this engineered tissue construct is clearly visible in the schematics and images shown in FIGS. 10B-10D. Using confocal laser scanning microscopy, it is possible to fully interrogate this 3D tissue construct and determine the precise locations of each cell. Confocal microscopy images of the 3-D printed structure in XY, XZ, and YZ after 2 days of culture are shown in FIG. 10G. To demonstrate the versatility of this approach, other 3D tissue construct were also designed and printed. Although it is difficult to obtain confocal images due the dense, interpenetrating nature of the cell-laden filaments, both the green fluorescent protein expressing HNDFs in GelMA and the red-HUVECs that line the 3-D vasculature network are visible.

Investigation of Cell Viability

As a final step, the viability of the printed 10T1/2 fibroblast cells over the course of one week was investigated. At Day 0, the cell viability was 61%; however, it increased to 82% after 7 days. While there is lower initial cell viability compared with the control (78% on Day 0), the printed cells do proliferate and spread over time leading to similar levels of viability after 1 week in culture. The decreased initial viability could arise from the shear or extensional stress experienced by the cells during the printing process. Applied pressure, nozzle diameter, cell type, and environmental conditions may affect cell viability after printing. Another critical parameter is the total build time required to print the desired engineered tissue construct. There may be a maximum time over which the cell-laden inks can be stored in the ink reservoir prior to being harmed. However, implementation of multinozzle print heads that were reported previously (j. A. Lewis et al., "Multinozzle Deposition System for Direct Write Applications," International Patent Application No. PCT/US2012/044794, filed Jun. 29, 2012, which is hereby incorporated by reference) for high-throughput, multimaterial printing, may reduce the characteristic build times by two orders of magnitude in comparison with single nozzle printing. For example, printing an engineered tissue construct with a volume of 1000 cm³, comparable to a typical adult human liver, could require approximately 72 h using a single 200 μm nozzle at typical printing speeds. However, implementation of a 64-multinozzle array may reduce the respective build time to about 1 h.

Example 2: 3D Bioprinting of Thick Living Tissues

Central to the fabrication of thick living tissues is the design of biological, sacrificial, and elastomeric inks for multimaterial 3D bioprinting.

Methods

Solution Preparation:

Matrix and ink precursor solutions were prepared before creating tissue engineered constructs. A 15 wt/v % gelatin solution (Type A, 300 bloom from porcine skin, Sigma) was produced by warming in DPBS (IX Dulbelco's phosphate buffered saline without calcium and magnesium) to 70° C. (unless otherwise noted) and then gelatin powder was added to the solution while vigorously stirring. The gelatin was allowed to fully dissolve by stirring for 12 h at 70° C. (unless otherwise noted), and the pH was then adjusted to 7.5 using 1M NaOH. The warm gelatin solution was sterile filtered and stored at 4° C. in aliquots for later usage (<3 months).

Fibrinogen solution (50 mg mL$^{-1}$) was produced by dissolving lyophilized bovine blood plasma protein (Millipore) at 37° C. in sterile DPBS without calcium and magnesium. The solution was held at 37° C. undisturbed for 45 minutes to allow complete dissolution.

The transglutaminase (TG) solution (60 mg mL$^{-1}$) was prepared by dissolving lyophilized powder (Moo Glue) in DPBS without calcium and magnesium and gently mixing for 20 sec. The solution was then placed at 37° C. for 20 minutes and sterile filtered before using.

A 250 mM CaCl$_2$ stock solution was prepared by dissolving CaCl$_2$ powder in DPBS without calcium and magnesium (Corning).

To prepare stock solution of thrombin, lyophilized thrombin (Sigma Aldrich) was reconstituted at 500 U mL$^{-1}$ using sterile DPBS, aliquotted and stored at −20° C. The thrombin aliquots were thawed immediately prior to use.

Matrix Formulations:

To create gelatin-fibrin IPNs, solutions of fibrinogen, gelatin, calcium and TG were mixed together at various concentrations at 37° C. A typical final concentration was 10 mg mL$^{-1}$ fibrinogen, 7.5 wt % gelatin, 2.5 mM CaCl$_2$ and 0.2 wt % TG. For printing the large-scale tissues (FIG. 33), 1 wt % TG was used to account for diffusion and dilution into printed cell filaments. The amount of time these components were allowed to sit before mixing with thrombin determined matrix optical clarity (FIG. 24 A through 24D). This wait step, termed "TG preincubation time," was typically 15-20 minutes. After TG preincubation time, the solution was rapidly mixed with thrombin at a ratio of 500:1 resulting in a final concentration of 1 U mL$^{-1}$. After mixing, the matrix was cast within 30 sec, as irreversible, enzymatically driven polymerization of fibrinogen into fibrin gel occurs rapidly.

Ink Formulations:

Several inks were created for 3D bioprinting of thick vascularized tissues.

The first ink, which is used to create customized perfusion chips, was composed of a two-part silicone elastomer (SE 1700, DOW Chemical) with a 10:1 base to catalyst (by weight) that was homogenized using a mixer (2000 speed, AE-310, Thinky Corp, Japan). The silicone ink was printed within two hours of mixing with catalyst.

The second ink, which was a fugitive ink used to print the vasculature, was composed of 38 wt % Pluronic F127 (Sigma) and 100 U mL$^{-1}$ thrombin in deionized, ultrafiltrated (DIUF) water. To prepare this ink, 40% stock Pluronic F127 was homogenized using a Thinky mixer until the powder was fully dissolved, and subsequently stored at 4° C. Prior to use, a 2000 U mL$^{-1}$ thrombin solution was added to the fugitive (Pluronic) ink at a ratio of 1:200, and homogenized using a Thinky mixer. This ink was then loaded in a syringe (EFD Inc., East Providence, R.I.) at 4° C. and centrifuged to remove any air bubbles. Before printing, this ink was brought to room temperature.

The third ink, a cell-laden printable ink, was composed of 7.5 wt/vol % gelatin and 10 mg ml$^{-1}$ fibrinogen, unless otherwise noted. Notably, ink stiffness was tuned by varying the gelatin process temperature (70° C.-95° C.) (FIG. 25A though 25I). This ink was prepared similarly to the IPN matrix, however, no TG or thrombin was used in this formulation.

Crosslinking of printed ink was achieved through diffusion of thrombin and TG from the surrounding matrix after casting. To uniformly disperse cells into the ink, the fibrinogen-gelatin blend was maintained in a liquid state at 37° C. and then cell suspensions with concentrations greater than 2×10$^6$ Cells mL$^{-1}$ were mixed via gentle pipetting. After the ink was thoroughly mixed, the ink was held at 4° C. for 15 min to drive thermal gelation of the gelatin phase. Next, the ink was removed from the refrigerator and allowed to equilibrate to room temperature for at least 15 min, mounted to the 3D bioprinter and used immediately for up to 2 h.

Fibrinogen-Fluorophore Conjugation:

To visualize the fibrin network in printed filaments and the casting matrix, fibrinogen was conjugated to two fluorophores. Specifically, 1 g of bovine fibrinogen was dissolved in 100 ml of 50 mM borate buffer, pH 8.5 (Thermo Scientific) to form a 10 mg ml$^{-1}$ solution. To this solution, N-hydroxysuccinimide (NHS), conjugated with either fluorescein or rhodamine was added at a molar ratio of 10:1 dye:fibrinogen. After reacting for 2 h at room temperature, the labeled fibrinogen was separated from unconjugated dye by dialysis using 10 kDa MWCO dialysis tubing in a 2 L bath against PBS for 3 days, changing the PBS in the bath twice daily. After dialysis was complete, the fluorescently conjugated fibrinogen was frozen at −80° C., lyophilized, and stored at −20° C. before use.

Rheological Characterization:

The ink rheology is measured using a controlled stress rheometer (DHR-3, TA Instruments, New Castle, Del.) with a 40 mm diameter, 2° cone and plate geometry. The shear storage (G') and loss (G") moduli are measured at a frequency of 1 Hz and an oscillatory strain (γ) of 0.01. Temperature sweeps were performed using a Peltier plate over the range from −5° C. to 40° C. Samples were equilibrated for 5 min before testing and for 1 min at each subsequent temperature to minimize thermal gradients throughout the sample. Time sweeps were conducted by rapidly placing a premixed solution onto the temperature-controlled Peltier plate held at 37° C. or 22° C., unless otherwise noted. It was important to minimize bubble generation during mixing, because the solution rapidly gels upon casting.

Cell Culture and Maintenance:

Human bone-marrow derived mesenchymal stem cells (hMSCs) (Rooster Bio) were cultured in Booster Media (Rooster Bio) and were not used beyond 2 passages.

Green fluorescent protein-expressing human neonatal dermal fibroblast cells (GFP-HNDFs, Angio-Proteomie) were cultured in Dulbelco's modified Eagle medium containing high glucose and sodium pyruvate (DMEM) (GlutaMAX™, Gibco) and supplemented with 10% fetal bovine serum (FBS) (Gemini Bio-Products).

Primary red fluorescent protein expressing human umbilical vein endothelial cells (RFP-HUVECs) (AngioProteomie) were cultured in EGM-2 media (complete EGM™-2 BulletKit™, Lonza).

All the cell cultures were passaged per the respective vendor's instructions. GFP-HNDFs and RFP HUVECs were not used beyond the fifteenth and ninth passages, respectively.

3D Perfusion Chip Fabrication:

All vascularized tissues were created on a custom-designed multimaterial 3D bioprinter equipped with four independently addressable printheads mounted onto a 3-axis, motion-controlled gantry with build volume 725 mm×650 mm×125 mm (AGB 10000, Aerotech Inc., Pittsburgh, Pa. USA). Each ink was housed inside a separate syringe barrel to which nozzles of varying size (i.e., 100 μm-410 μm diameter) were attached via a leur-lock (EFD Inc., East Providence, R.I., USA). Inks were extruded through each deposition nozzle by applying air pressure (800 Ultra dispensing system, EFD Inc., East Providence, R.I., USA), ranging from 10-140 psi, corresponding to print speeds from 1 mm s$^{-1}$ to 5 cm s$^{-1}$. Prior to printing, the relative X-Y offsets of the four printheads were determined using orthogonally mounted optical micrometers (LS-7600 series, Keyence, Japan).

To manufacture the customized perfusion chips, the silicone ink was loaded into a 10 ml syringe, centrifuged to remove air bubbles, and deposited through a tapered 410 μm nozzle. The gasket design was created using custom MATLAB software and the structures were printed onto 50 mm×75 mm glass slides. After printing, the chips were cured at 80° C. in an oven for >1 hour and stored at room temperature.

Figures 24A, 24B, 24C, 24D:
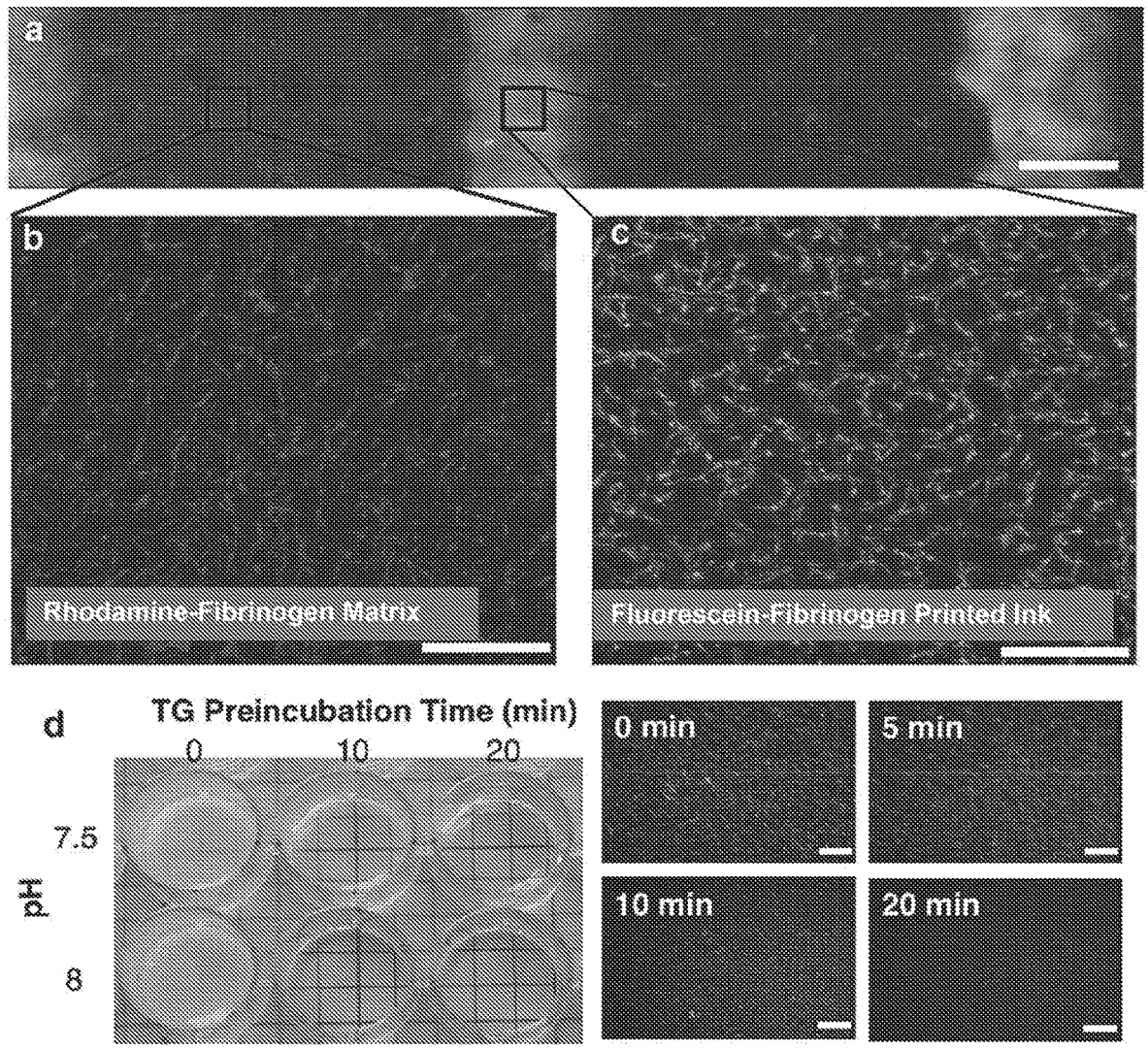
FIGS. 24A-C depict images of fibrin structure within the printed ink and matrix.
FIG. 24D depicts photographs showing TG preincubation time before adding thrombin; the TG concentration used in these gels is 0.2% wt, scale bar=50 μm.

To produce thick vascularized tissues, multiple inks were sequentially co-printed within the customized perfusion chips. To form a base layer, a thin film of gelatin-fibrin matrix, containing 0.1% wt TG, was cast onto the base of the perfusion chip and allowed to dry. Next, the fugitive Pluronic F127 and cell-laden inks were printed onto the surface. The fugitive (Pluronic F127) and cell-laden inks were printed using 200 μm straight and tapered nozzles, respectively. After printing, stainless metal tubes were fed through the guide channels of the perfusion chip and pushed into physical contact with printed vertical pillars composed of the fugitive ink, which were positioned at the inlets and outlets (FIGS. 26A-26S). Prior to encapsulation, TG was added to the molten 37° C. gelatin-fibrin matrix solution and preincubated for 2-20 min depending on the desired matrix transparency (FIG. 24D). To form a cell-laden matrix, the molten 37° C. gelatin-fibrin matrix was first mixed with HNDF-GFP cells and then mixed with thrombin. Next, this matrix was immediately cast within the perfusion chip to fully encapsulate the printed tissue, where it underwent rapid gelation due to thrombin activity. The tissues were then stored at 37° C. for 1 h to allow fibrin polymerization to terminate and TG to crosslink the network. The entire structure was then cooled to 4° C. to liquefy the printed fugitive ink, which was then flushed through the device using cold cell media, leaving behind open conduits that serve as the desired vascular network embedded within the printed tissue and surrounding cell-laden matrix.

The 3D perfusion chips were loaded onto a machined stainless steel base, and a thick acrylic lid was placed on top. The lid and base were clamped together by four screws, forming a seal around the silicone 3D printed gasket top. Next, sterile two-stop peristaltic tubing (PharMed BPT) was filled with media and connected to the outlet of a sterile filter that was attached to a 10 ml syringe (EFD Nordson), which served as a media reservoir. Media that has been equilibrating for >6 h in an incubator at 37° C., 5% $CO_2$ was added to the media reservoir, and by means of gravity, was allowed to flow through the filter and peristaltic tubing, until all the air was displaced, before connecting the peristaltic tubing to the inlet of each perfusion chip. To complete the perfusion circuit, silicone tubing was connected between the outlet of the perfusion chip and an inlet at the top of the media reservoir. Hose pinch-off clamps were added at the inlet and outlet of the perfusion chip to prevent uncontrolled flow when disconnected from the peristaltic pump, which can damage the endothelium or introduce air bubbles to the vasculature. The media reservoir was allowed to equilibrate with atmospheric pressure at all times by means of a sterile filter connecting the incubator environment with the reservoir.

Endothelialization of Vascular Networks:

With the peristaltic tubing removed from the chip outlet, 50-500 μL HUVEC suspensions ($1 \times 10^7$ cells $mL^{-1}$) were injected via pipette to fill the vascular network. Then, the silicone tubing was replaced on the chip outlet and both the outlet and inlet pinch-clamp were sealed. The perfusion chip was incubated at 37° C. to facilitate cell adhesion to the channels under zero-flow conditions. After 30 min, the chip was flipped 180° to facilitate cell adhesion to the other side of the channel, and achieve circumferential seeding of cells in the channel. Finally, the cells were further incubated for between 5 h and overnight at 37° C. before commencing active perfusion.

Active Perfusion:

After endothelial cell seeding, the peristaltic tubing was affixed to a 24-channel peristaltic pump (Ismatec), after which the inlet and outlet hose clamps were unclipped to prepare for perfusion. The peristaltic pump was then started at a desired perfusion rate. For single vascular channels, the perfusion rate was set at 13 μL $min^{-1}$, while for the thick, large-scale tissues it was set at 27 μL $min^{-1}$.

Cell Viability Assay:

Cell viability was determined post-printing by printing inks with $2 \times 10^6$ cells $mL^{-1}$ for each condition. For printed cell viability, the printed filaments were deposited onto a glass substrate and then stained using calcein-AM ("live", 1 μL $mL^{-1}$, Invitrogen) and ethidium homodimer ("dead", 4 μL $mL^{-1}$, Invitrogen) for 20 minutes prior to imaging via confocal microscopy (n=3 unique samples, imaged n=10 times). Live and dead cell counts were obtained using the 3D objects counter plugin in ImageJ software. The results were averaged and standard deviations determined for each sample.

Imaging and Analysis:

Macroscopic photographs and videos of printing and assembly of tissues were collected using a DSLR camera (Canon EOS, 5D Mark II, Canon Inc., USA). Fluorescent dyes were used to improve visualization of Pluronic F127 (Red, Risk Reactor) and gelatin-fibrin ink (Fluorescein, Sigma Aldrich). Various microscopes were used to visual printed tissue structures including a Keyence Zoom (VHX-2000, Keyence, Japan), an inverted fluorescence (Axiovert 40 CFL, Zeiss), and an upright confocal microscope (LSM710, Zeiss). ImageJ was used to generate composite microscopy images by combining fluorescent channels. 3D rendering and visualization of confocal stacks was performed in Imaris 7.6.4, Bitplane Scientific Software and ImageJ software. Cell counting was performed using semi-automated native algorithms in Imaris and ImageJ counting and tracking algorithms.

Immuno-Staining:

Immuno-staining and confocal microscopy were used to assess the 3D vascularized tissues. Printed tissues were first washed with phosphate buffered saline (PBS) via perfusion for several minutes. Next, 10% buffered formalin was perfused through the 3D tissue for 10 to 15 min. The tissue was removed from the perfusion chip and bathed in 10% buffered formalin. Time of fixation with formalin varied with tissue construct thickness; approximately 2 h of fixation was required for a 1 cm thick tissue. The 3D tissues were then washed in PBS for several hours and blocked overnight using 1 wt % bovine serum albumin (BSA) in PBS. Primary antibodies to the cell protein or biomarker of interest were incubated with the constructs for 2 days at the dilutions listed in Table 1 below in a solution of 0.5 wt % BSA and 0.125 wt % TritonX.

TABLE 1

| Antibody or stain: | Source | Catalog # | Host Species & Reactivity | Concentration |
| --- | --- | --- | --- | --- |
| CD31 | abcam | ab24590 | Mouse anti-human | 1:200 |
| VECadherin | Cell Signaling Technology | D87F2 | Rabbit anti-human | 1:250 |
| von Willebrand Factor | abcam | ab194405 | Mouse anti-human | 1:250 |
| Alpha-smooth muscle actin | abcam | ab18147 | Mouse anti-human | 1:250 |
| Osteocalcin | abcam | ab13418 | Mouse anti-human | 1:200 |
| Collagen I | abcam | ab34710 | Rabbit anti-human | 1:400 |
| ActinGreen | Life Technologies | R37110 | N/A | 2 drops per mL |

TABLE 1-continued

| Antibody or stain: | Source | Catalog # | Host Species & Reactivity | Concentration |
|---|---|---|---|---|
| NucBlue | Life Technologies | R37605 | N/A | 2 drops per mL |
| Fast blue | Sigma Aldrich | B5655 | N/A | 20 mg per mL |
| Alizarin Red | Sigma Aldrich | A5533 | N/A | 50 µg per mL |

Removal of unbound primary antibodies was accomplished using a wash step against a solution of PBS or 0.5 wt % BSA and 0.125 wt % TritonX in PBS for 1 day. Secondary antibodies were incubated with the constructs for 1 day at the dilutions listed in Table 1 above in a solution of 0.5 wt % BSA and 0.125 wt % TritonX in PBS. Samples were counter-stained with NucBlue or ActinGreen for 2 h and then washed for 1 day in PBS prior to imaging. Confocal microscopy was performed using an upright Zeiss LSM 710 with water immersion objectives ranging from 10× to 40× employing spectral lasers at 405, 488, 514, 561, and 633 nm wavelengths. Image reconstructions of z-stacks were performed in ImageJ using the z-project function with the maximum pixel intensity setting. Three dimensional image reconstructions were performed using Imaris software.

hMSC Staining:

Fast Blue (Sigma Aldrich) and alizarin red (SigmaFast, Sigma Aldrich) were used to visualize AP activity and calcium deposition. One tablet of Fast Blue was dissolved in 10 mL of DI water. This solution was stored in the dark and used within 2 hours. Cells were washed using 0.05% Tween 20 in DPBS without calcium and magnesium and fixed as described above. The samples were then covered with Fast Blue solution and incubated in the dark for 5-10 min and washed using PBS-Tween buffer. To assess mineralization, 2% alizarin red solution was dissolved in DI water, mixed vigorously, filtered, and used within 24 hours. Samples were equilibrated in DI water and incubated with Alizarin Red solution for 2-5 minutes, then the staining solution was removed, and samples were washed 3× in DI water or until background dye was unobservable.

FITC-Dextran Permeability Testing:

To assess barrier function of the printed vasculature, diffusional permeability was quantified by perfusing culture media in the vascular channel, while alive, containing 25 µg/mL FITC-conjugated 70 kDa dextran (FITC-Dex, Sigma product 46945) at a rate of 20 µL min$^{-1}$ for 3 min and 1 µL min$^{-1}$ thereafter for ~33 min. The diffusion pattern of FITC-Dex was detected using a wide-field fluorescent microscope (Zeiss Axiovert 40 CFL). Fluorescence images were captured before perfusion and every 3 to 5 min after for 33 min. Diffusional permeability of FITC-Dex was calculated by quantifying changes of fluorescence intensity over time using the following equation:

$$P_d = \frac{1}{I_1 - I_b}\left(\frac{I_2 - I_1}{t}\right)\frac{d}{4}$$

where Pd is the diffusional permeability coefficient, $I_1$ is the average intensity at an initial time point, $I_2$ is an average intensity after some time (t, ~30 min), $I_b$ is background intensity (image taken before perfusion of FITC-Dex), and d is diameter of the channel (Price G, Tien J (2011) Methods in Molecular Biology ed khademhosseini A (Humana Press)).

The permeability measurement was performed on two types of channel structures: 1) perfused channel with cell lining, 2) perfused channel without cell lining (empty channel). For each type, the diffusional permeability was calculated from the measurement of three independent samples (n=3).

Discussion

To satisfy the concomitant requirements of processability, heterogeneous integration, biocompatibility, and long-term stability, we first developed new printable cell-laden ink and castable extracellular matrix (ECM) comprising a blend of gelatin and fibrinogen (Lee K Y, Mooney D J (2001) Hydrogels for Tissue Engineering. *Chem Rev* 101(7):1869-1880).

Figures 27A, 27B, 27C, 27D, 27E, 27F, 27G, 27H, 27I, 27J, 27K, 27L:
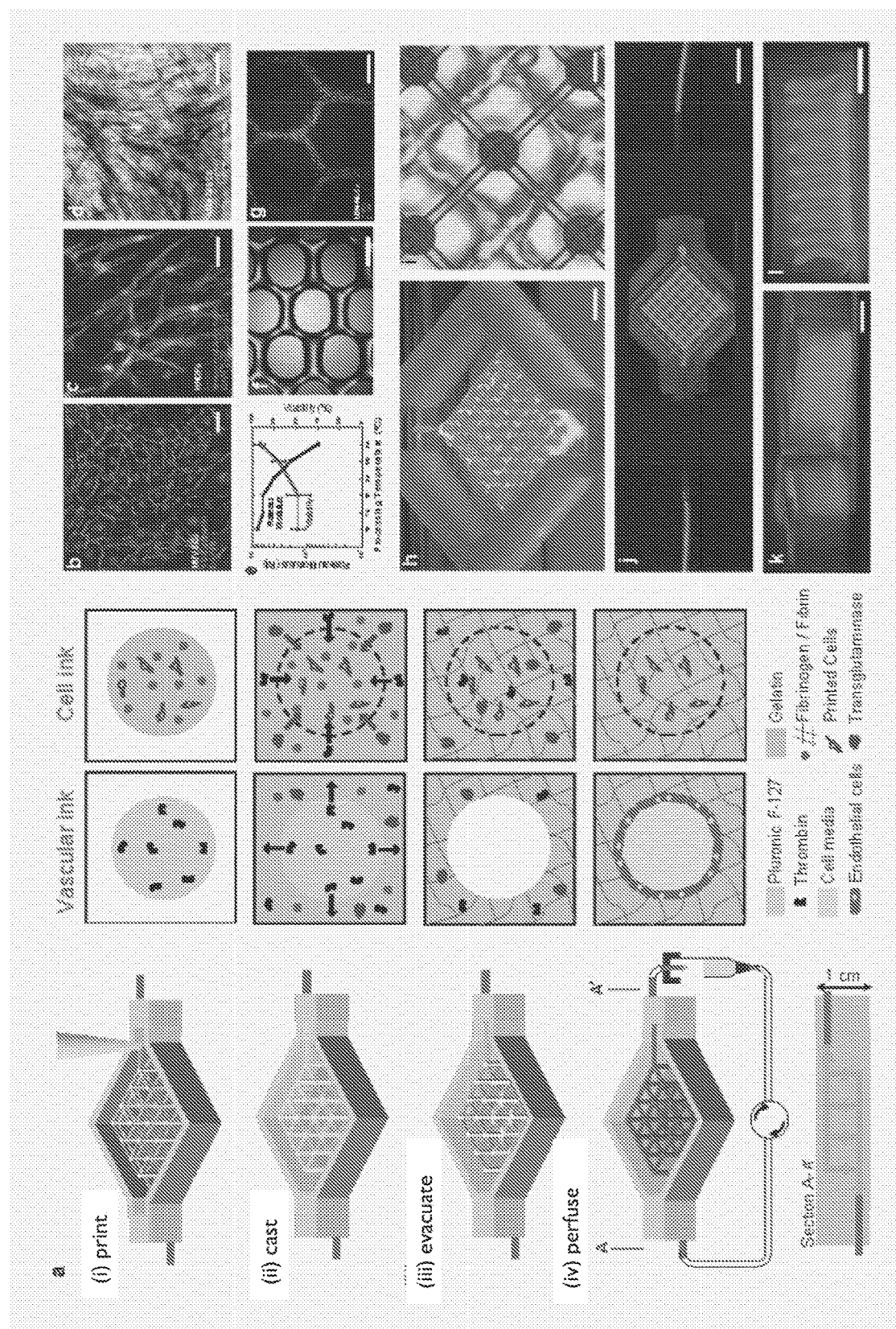
FIGS. 27A-27F depict 3D vascularized tissue fabrication.
FIG. 27G shows that gelatin processing temperature affects the plateau modulus and cell viability after printing. Higher temperatures lead to lower modulus and higher HNDF viability post-printing.
FIG. 27H is a photograph of interpenetrated sacrificial (red) and cell inks (green) as printed on chip, scale bar=2 mm.
FIG. 27I depicts a top-down bright field image of sacrificial and cell inks, scale bar=50 μm.
FIG. 27J depicts a photograph of a completed construct housed within a perfusion chamber.
FIGS. 27K and 27L depict corresponding cross sections of a completed construct housed within a perfusion chamber, scale bars=5 mm.
Figures 28A, 28B, 28C, 28D, 28E, 28F:
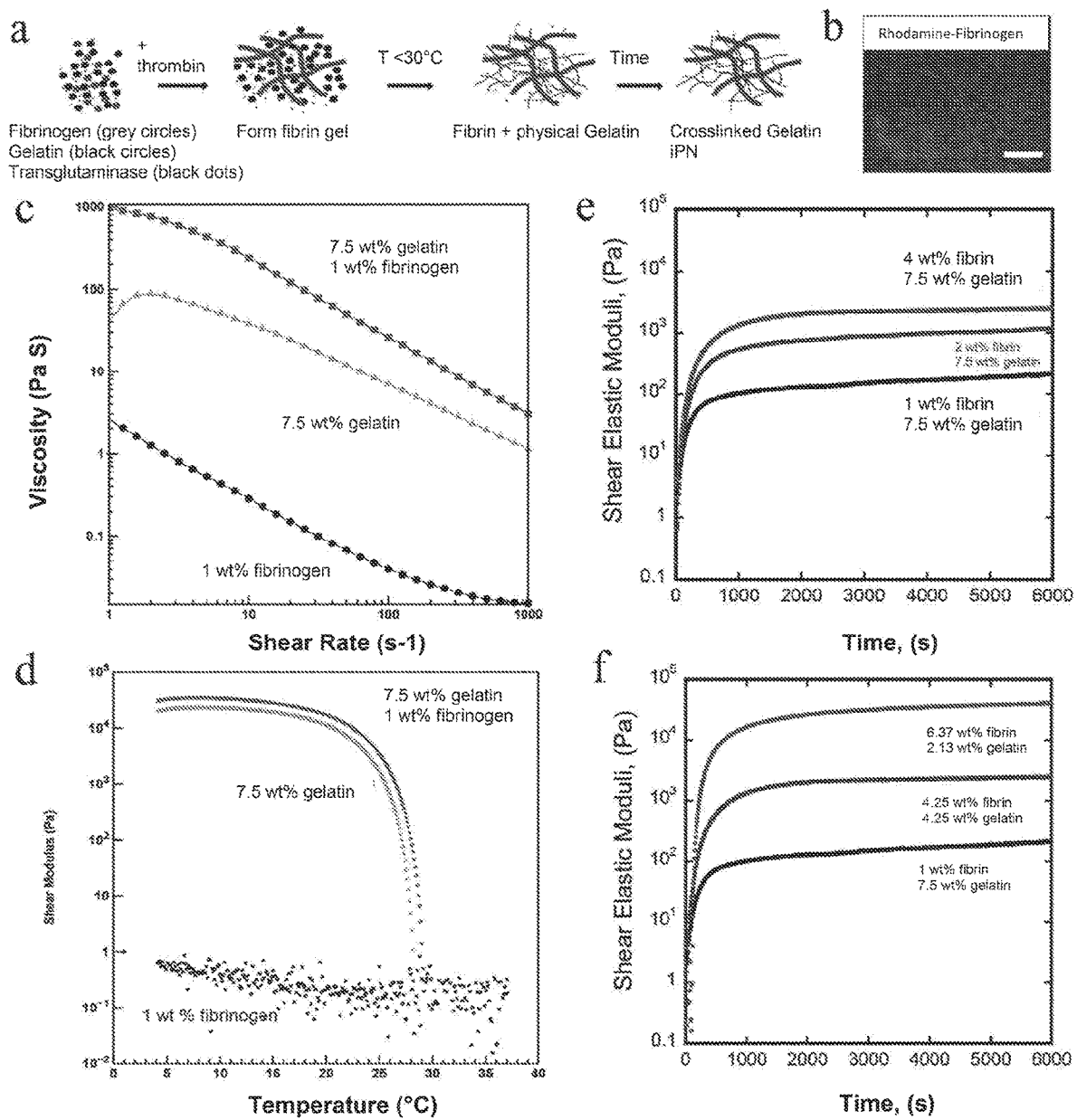
FIG. 28A depicts a schematic showing the three-step gelation of gelatin-fibrin.
FIG. 28B depicts a fluorescent image of rhodamine labeled fibrinogen within a gelatin-fibrin IPN demonstrating that a dense fibrillar network of fibrin is formed upon addition of thrombin, scale bar=50 μm.
FIG. 28C depict a graph showing that, at 37° C., fibrinogen increases the solution viscosity of gelatin upon addition, yet only marginally alters the shear plateau modulus of the resulting gel at room temperature.
FIG. 28D depict a graph showing that viscoelastic behavior of gelatin fibrin inks is highlighted by several orders of magnitude of shear elastic modulus. At room temperature (22° C.) and below, the modulus of printable gelatin-fibrinogen inks is between IE4-IE5 Pa. When the temperature is increased above 30° C. the solution is rheologically suitable for cell dispersion and casting—the solution exists in the viscous state with a shear elastic modulus approaching zero.
FIGS. 28E and 28F depict graphs showing that the dynamic shear elastic modulus of fibrin-gelatin rapidly increases with time upon addition of thrombin, indicating fibrin network formation, while the plateau elastic modulus increases with increasing fibrin content (FIG. 28E) within a fibrin-gelatin composite, the fibrin phase of the IPN imparts more stiffness to the resulting gel (FIG. 28F).
Figures 29A, 29B:
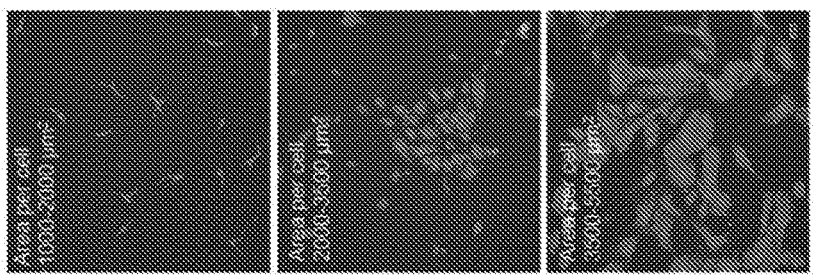
FIG. 29A depicts a table showing the adhesion behavior and relative cell spreading on various matrix formulations.
FIG. 29B shows fluorescent micrographs of RFP-HUVECs showing examples of low, medium, and high levels of cell spreading on gels. Fibrinogen is gelled at pH 7 to generate an opaque fibrin gel, and at pH 7.5 to generate a transparent or "clear" fibrin gel. pH is adjusted using 1M NaOH, scale bar=50 μm.

Specifically, these materials form a tough interpenetrating polymer network (IPN) composed of gelatin-fibrin cross-linked by a dual-enzyme, thrombin and transglutaminase, strategy (FIGS. 26, and 27A through 27L). The cell-laden inks must simultaneously facilitate printing of self-supporting filamentary features under ambient conditions and subsequent infilling of the printed tissue architectures by casting without dissolving or distorting the patterned cell-laden and fugitive (vasculature) inks (FIG. 27A). The thermally reversible gelation of the gelatin-fibrinogen network enables its use in both printing and casting, where gel and fluid states are required, respectively (FIGS. 28A though 28F). Thrombin is used to rapidly polymerize fibrinogen (Mosesson M W (1998), Semin Thromb Hemost 24(2):169-174), while TG is a slow-acting $Ca^{2+}$-dependent enzymatic crosslinker that imparts mechanical and thermal stability to the gel in culture (Chen R-N, Ho H-O, Sheu M-T (2005) Characterization of collagen matrices crosslinked using microbial transglutaminase. Biomaterials 26(20):4229-4235), enabling long term perfusion. Notably, the printed cell-laden ink does not contain either enzyme to prevent polymerization during printing. While the castable (matrix) ink contains both thrombin and TG, which diffuse into adjacent printed filaments forming a continuous interpenetrating polymer network (IPN), in which the native fibrillar structure of fibrin is preserved (FIG. 24). Importantly, our approach allows arbitrarily thick tissues to be fabricated, since these inks do not require UV irradiation to cure, which has a low penetration depth within scattering tissue (Jayakumar M K G, Idris N M, Zhang Y (2012) Remote activation of biomolecules in deep tissues using near-infrared-to-UV upconversion nanotransducers. *Proceedings of the National Academy of Sciences* 109(22):8483-8488).

The gelatin-fibrin matrix supports multiple cell types of interest to both 2D and 3D culture conditions, including human umbilical vein endothelial cells (HUVECs), human neonatal dermal fibroblasts (HNDFs), and human bone marrow-derived mesenchymal stem cells (hMSCs) (FIGS. 27B-D and FIGS. 29A-B).

We found that endothelial cells express vascular endothelial-cadherin (VE-Cad) (FIG. 27B), and HNDFs (FIG. 27C) and hMSCs (FIG. 27D) proliferate and spread on this matrix surface and in bulk.

Moreover, the printed cell viability can be as high as 95% depending on how the gelatin is preprocessed. At higher temperatures, the average molecular weight of gelatin is reduced (69 kDa at 70° C. processing to 32 kDa at 95° C. processing) resulting in softer gels with lower viscosity, shear yield stress, and shear elastic modulus that can be printed with ease (FIG. 27E and FIG. 25). Upon printing, hMSCs within this soft gelatin-fibrinogen matrix continue to spread, proliferate, and contract into dense, cellular architectures that align along the printing direction (FIG. 26F), likely arising due to cellular confinement (Klumpers D D, Zhao X, Mooney D J, Smit T H (2013) Cell mediated contraction in 3D cell-matrix constructs leads to spatially regulated osteogenic differentiation. *Integr Biol* 5(9):1174-1183) and contraction via the Poisson-effect (Oster G F, Murray J D, Harris A K (1983) Mechanical aspects of mesenchymal morphogenesis. *J Embryol Exp Morphol*: 83-125).

To construct thick living tissues within perfusion chips, we co-printed cell-laden, fugitive, and silicone inks (FIGS. 27H-27I).

First, the silicone ink is printed on a glass substrate and cured to create customized perfusion chips, as shown in FIGS. 26A-26S. Next, the cell-laden and fugitive inks are printed on chip, and then encapsulated in the castable ECM matrix (FIGS. 27J-27L). The fugitive ink, which defines the vascular network, is composed of a triblock copolymer (i.e., polyethylene oxide (PEO)-polypropylene oxide (PPO)-PEO). This ink can be removed from the fabricated tissue upon cooling to roughly 4° C., where it undergoes a gel-to-fluid transition, as previously shown. This process yields a pervasive network of open channels, which are then lined with HUVECs. The vasculature is then perfused over long time periods using an external pump (not shown) that generates a smooth flow over a wide range of flow rates (Giulitti S, et al. (2013) Optimal periodic perfusion strategy for robust long-term microfluidic cell culture. Lab on a Chip 13 (22):4430).

Figures 30A, 30B, 30C, 30D, 30E, 30F:
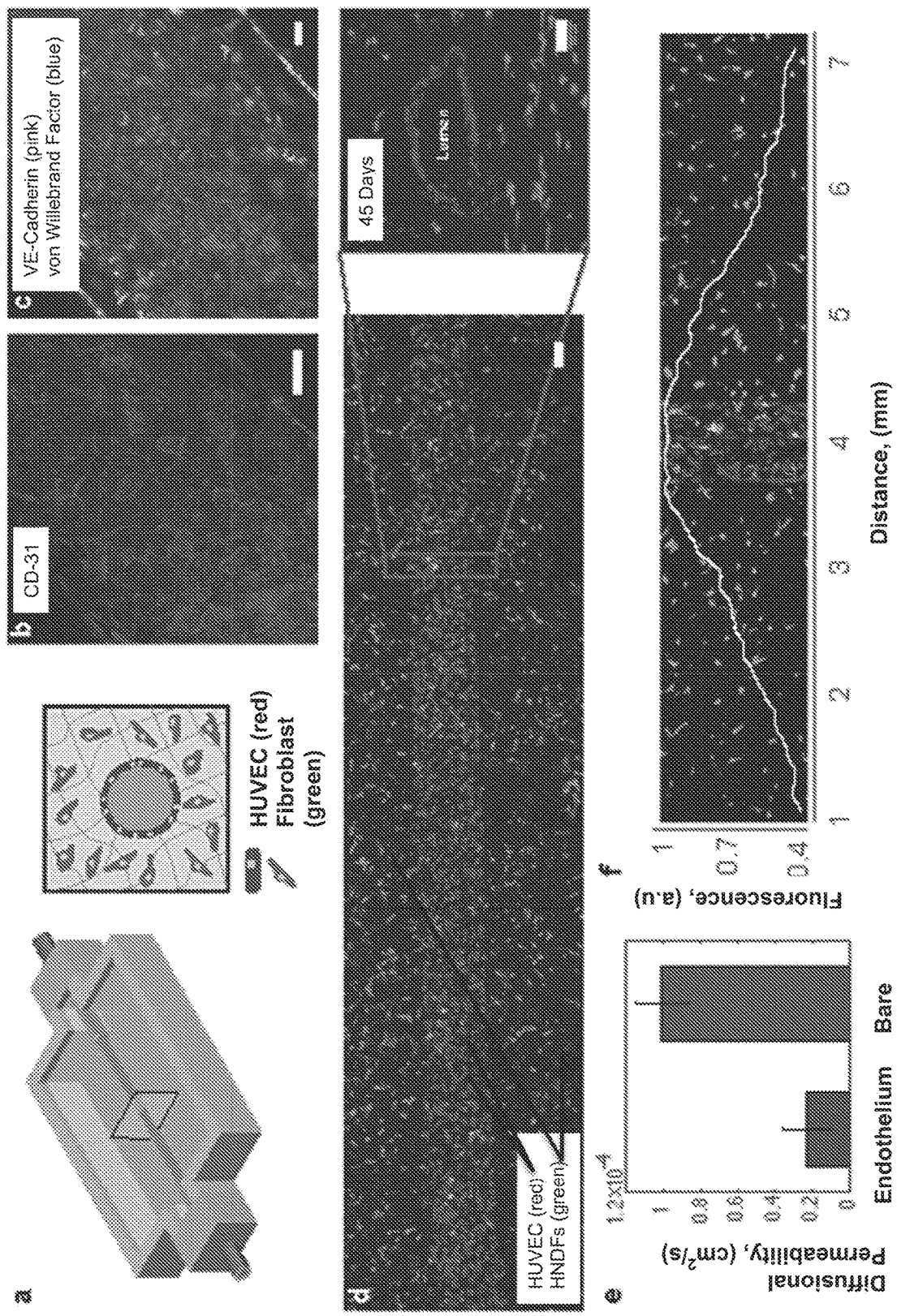
FIG. 30A is a schematic depicting a single HUVEC-lined vascular channel supporting a fibroblast cell-laden matrix and housed within a perfusion chip.
FIGS. 30B and 30C are confocal microscopy images of the vascular network after 42 days, CD-31 (red), vWF (blue), and VE-Cadherin (magenta). scale bars=100 μm.
FIG. 30D shows a long-term perfusion of HUVEC-lined (red) vascular network supporting HNDF-laden (green) matrix shown by top-down (left) and cross-sectional confocal microscopy at 45 days (right), scale bar=100 μm.
FIG. 30E shows a bar graph showing quantification of barrier properties imparted by endothelial lining of channels, demonstrated by reduced diffusional permeability of FITC-dextran.
FIG. 30F depicts GFP-HNDF distribution within the 3D matrix shown by fluorescent intensity as a function of distance from vasculature.
Figures 31A, 31B, 31C:
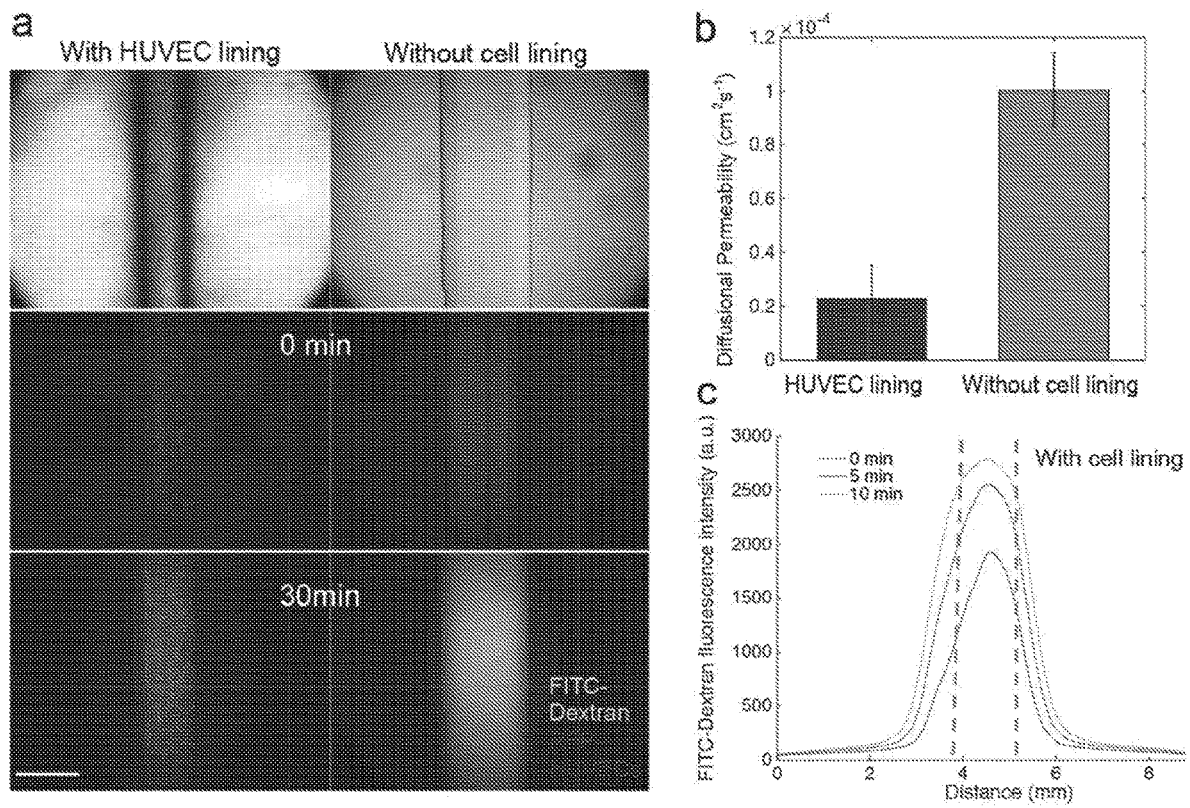
FIG. 31A depicts images of FITC-labeled Dextran (70 kDa) perfused through channels with, and without a lining of HUVECs. The fluorescence signal was recorded every 5 minutes up to 30 minutes to measure the degree of diffusion into the gel.
FIG. 31B depicts a bar graph of calculated diffusional permeability with and without the cell lining.
FIG. 31C depicts FITC-dextran fluorescence signatures with cell lining demonstrating the slow spreading of the fluorescence signal with time, scale bar=500 μm.

To demonstrate the formation of stable vasculature, we printed a simple tissue construct composed of two parallel channels embedded within a fibroblast cell-laden matrix (FIGS. 30A-30F). The channels are lined with HUVECs and subsequently perfused with endothelial growth media to form a confluent monolayer that lines each blood vessel (FIG. 30A).

Figure 32:
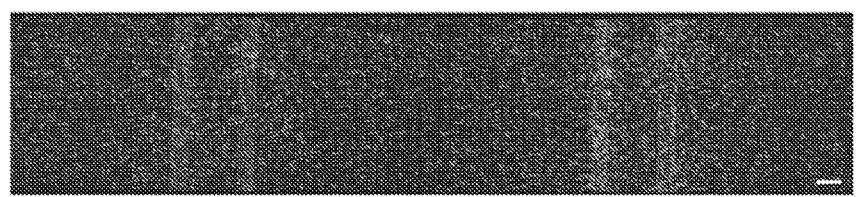
FIG. 32 depicts fibroblast cell proliferation within vascularized tissues. A GFP-expressing fibroblast laden gelatin-fibrin hydrogel is perfused via four printed channels that are lined with RFP-expressing HUVECs. The cell density, as measured by GFP levels, is maximal nearest to the channels, and decreases in the central region far from the channels, scale bar=500 μm.

Importantly, after six weeks of active perfusion, these endothelial cells maintain endothelial phenotype and remain confluent, characterized by expression of CD31, von-Willebrand Factor (vWF), and vascular endothelial cadherin (VECad) (FIGS. 30B-30C). The cross-sectional view of a representative vessel reveals lumen formation (FIG. 30D). Confirming the barrier function of the endothelium, we measured a five-fold reduction in the diffusional permeability compared to unlined (bare) channels (FIG. 30E and FIGS. 31A-31C). Stromal HNDFs residing within the surrounding matrix exhibit cell spreading and proliferative phenotypes localized to regions within ~1 mm of the vasculature (FIG. 30F and FIG. 32); cells further away from these regions become quiescent likely due to an insufficient nutrient supply. The perfusable vasculature is critical to support living tissues thicker than 1 mm over long time periods.

Figures 33A, 33B, 33C, 33D, 33E, 33F, 33G, 33H:
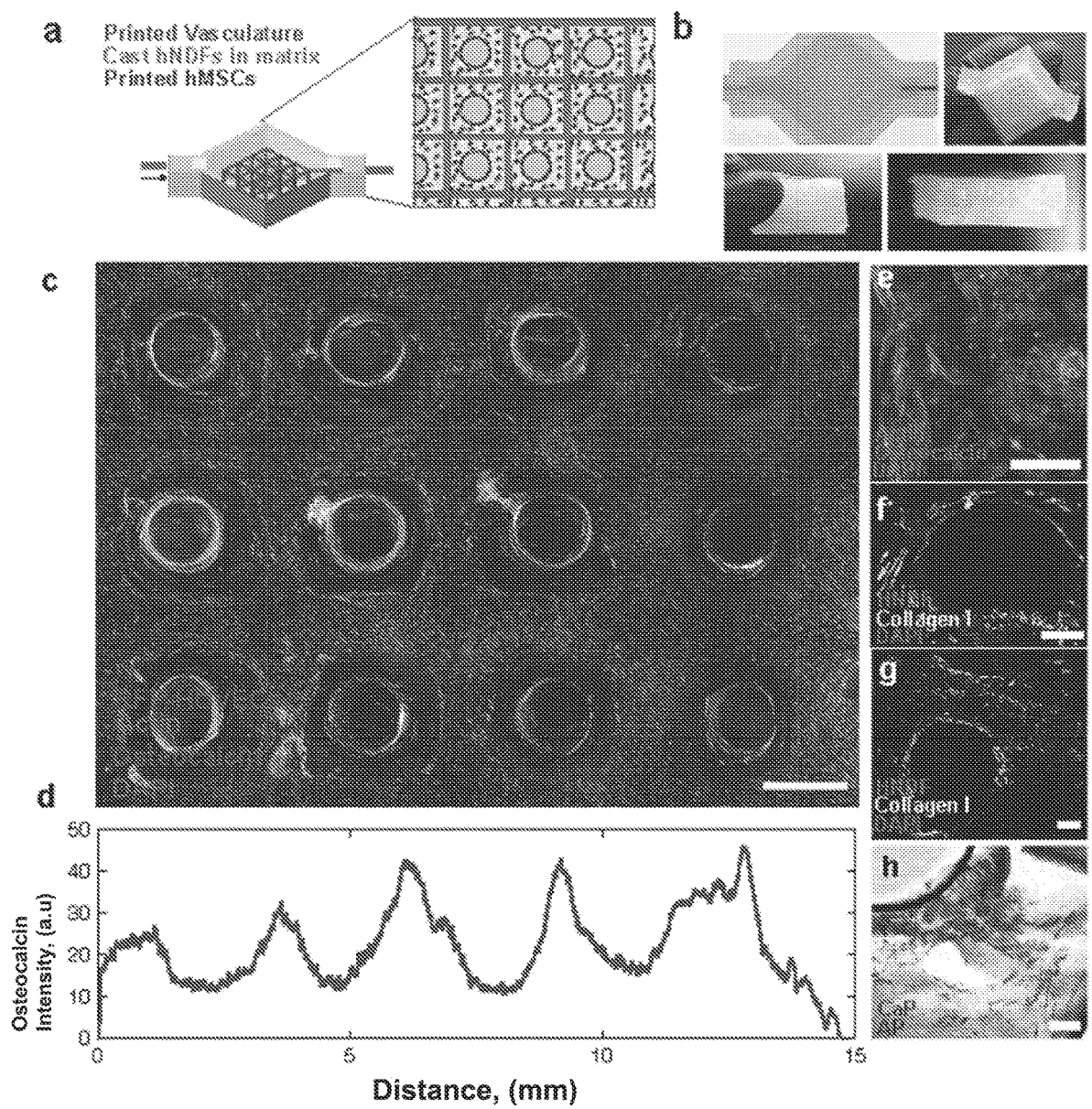
FIG. 33A depicts a Schematic depicting the geometry of the printed heterogeneous tissue within the customized perfusion chip, wherein the branched vascular architecture pervades hMSCs that are printed into a lattice architecture, and HNDFs are cast to fill the interstitial space.
FIG. 33B depicts photographs of a printed tissue construct within and removed from the customized perfusion chip, from the side.
FIG. 33C depicts a confocal microscopy image through a cross-section of 1 cm thick vascularized osteogenic tissue construct after 30 days of active perfusion and in situ differentiation, scale bar=1.5 mm.
FIG. 33D depicts osteocalcin intensity across the thick tissue sample inside the red lines shown in FIG. 33C.
FIGS. 33F-33G show images of thick tissue constructs stained for collagen-I (yellow), which appears localized near hMSCs, scale bars=200 μm.
FIG. 33H shows an image of alizarin red used to stain CaP deposition and fast blue is used to stain alkaline phosphatase, indicating tissue maturation and differentiation over time, scale bar=200 μm.

To explore emergent phenomena in complex microenvironments, we created a heterogeneous tissue architecture (>1 cm thick and 10 cm$^3$ in volume) by printing a hMSC ink into a 3D lattice geometry along with an interpenetrating, branched vascular network lined with HUVECs, and infilled with an HNDF-laden extracellular matrix uniformly distributed within the interstitial space (FIG. 33A). The fibroblast-laden matrix forms a connective tissue that both supports and binds the printed stem cell-laden tissue and vascular network. The embedded vascular network is designed with a single inlet and outlet that provides an interface between the printed tissue and the perfusion chip. This network is symmetrically branched to ensure uniform perfusion throughout the tissue, including deep within its core. In addition to providing transport of nutrients, oxygen, and waste materials, the perfused vasculature is used to deliver specific differentiation factors to the tissue in a more uniform manner than bulk delivery methods, in which cells at the core of the tissue are starved of factors (Griffith L G and Swartz M A (2006) Capturing complex 3D tissue physiology in vitro. *Nat Rev Mol Cell Biol* 7(3):211-224). This versatile platform (FIG. 33A) is used to precisely control growth and differentiation of the printed hMSCs. Moreover, both the printed cellular architecture and embedded vascular network are visible macroscopically with this thick tissue (FIG. 33B).

Figures 34A, 34B:
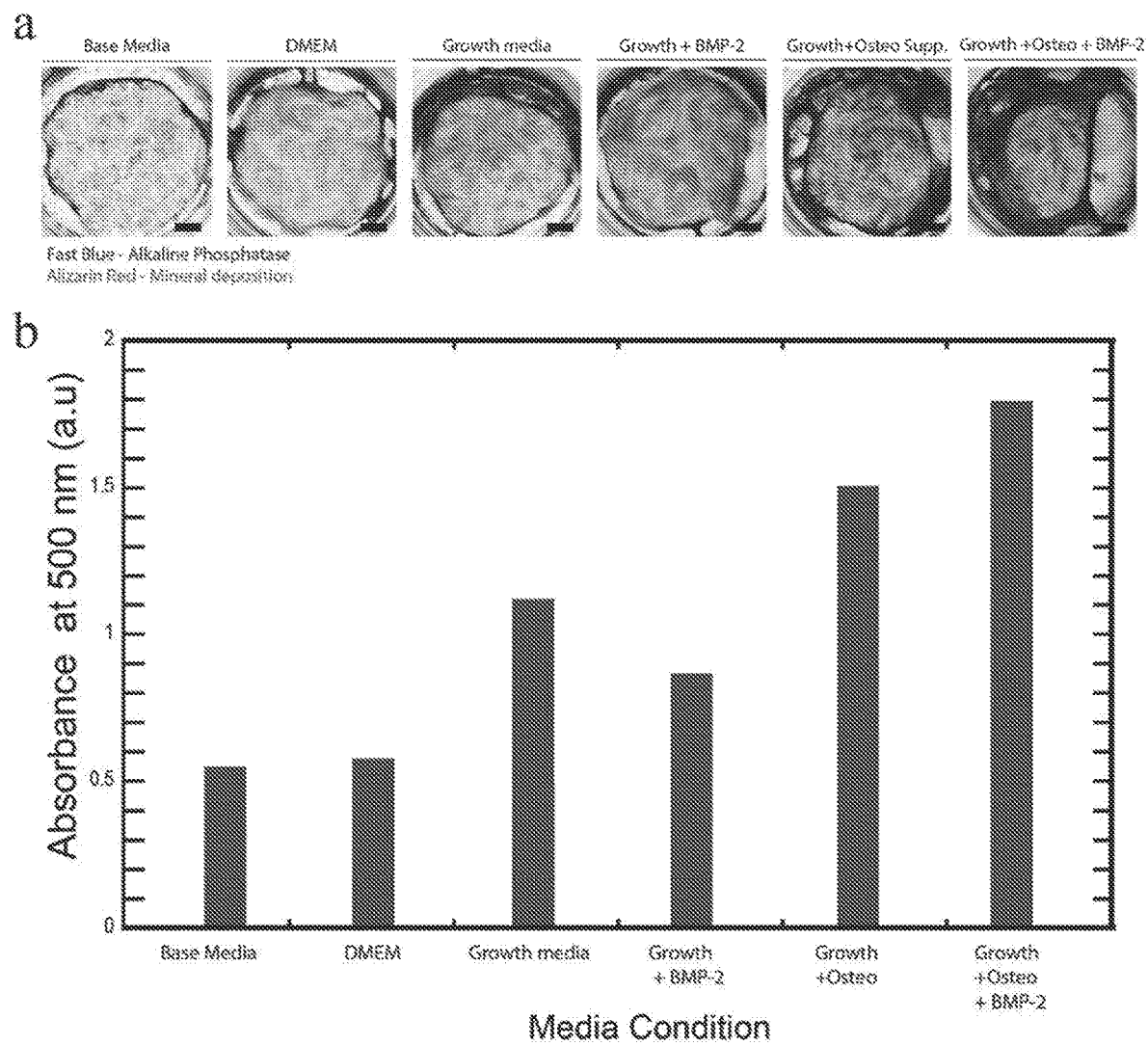
FIG. 34A shows images of hMSC's cultured in a polystyrene well in the presence of different media conditions. At day 14, the cells were stained with fast blue and alizarin red to visualize osteocytes and deposited minerals, respectively; scale bar=2 mm.
FIG. 34B depicts a graph showing average absorbance at 500 nm at 9 different locations within each well. 500 nm absorbance is a measure of the amount of alizarin red in the wells. Base media=Rooster Media. Growth media=Rooster media+GTX media booster. Osteo supplement=10 mM beta-glycerophosphate and 50 μg mL$^{-1}$ L-ascorbic acid. BMP-2 concentration=100 ng mL$^{-1}$.

To develop a dense osteogenic tissue, we transvascularly delivered growth media to the tissue during an initial proliferation phase (6 days) followed by an osteogenic differentiation cocktail that is perfused for several weeks. Our optimized cocktail is composed of BMP-2, ascorbic acid, and glycerophosphate, to promote mineral deposition and alkaline phosphatase (AP) expression (FIGS. 34A-34B).

To assess tissue maturation, changes in cell function and matrix composition are observed over time. In good agreement with prior studies (Klumpers D D, et al. (2013) Cell mediated contraction in 3D cell-matrix constructs leads to spatially regulated osteogenic differentiation. *Integr Biol* 5(9):1174-1183), we found that AP expression in hMSCs occurs within 3 days, while mineral deposition does not become noticeable until 14 days, which coincides with visible collagen-I deposition by hMSCs (FIGS. 35A-35B). The phenotype of differentiating hMSCs varies across the printed features: cells within the filament core are close-packed, compacted, and associated with high mineralization, while those in the periphery are more elongated, encapsulating the printed filaments, and exhibit less mineralization. We observe that sub-populations of both HNDFs and hMSCs migrate from their initial patterned geometry towards the vascular networks and wrap circumferentially around the channel (FIG. 33C). After 30 days, the printed hMSCs express osteocalcin within the tissue, and osteocalcin expression is proportional to distance from the nearest vessel (FIG. 3*d*). Further, we find that collagen deposition is localized within printed filaments and around the circumference of the vasculature (FIGS. 33E-33H).

In summary, thick, vascularized human tissues with programmable cellular heterogeneity that are capable of long-term (>30 days) perfusion on chip have been fabricated by multimaterial bioprinting. The ability to recapitulate physiologically relevant, 3D tissue microenvironments enables the exploration of emergent biological phenomena, as demonstrated by our observations of the in-situ development of hMSCs within tissues containing a pervasive, perfusable, endothelialized vascular network. Our 3D tissue manufacturing platform opens new avenues for fabricating and investigating human tissues for both ex vivo and in vivo applications.

Example 3: Bioprinting of Convoluted 3D Renal Proximal Tubules on Perfusable Chips Extracellular Matrix Preparation and Rheology The ECM is comprised of a network of gelatin and fibrin was prepared as described in Example 2 above.

A controlled stress rheometer (DHR-3, TA Instruments, New Castle, Del.) with a 40 mm diameter, 2° cone and plate geometry was used for ink rheology measurements. The shear storage (G') and loss (G") moduli were measured at a frequency of 1 Hz and an oscillatory strain (γ) of 0.01. Time sweeps were conducted by rapidly placing a premixed ECM solution that contains thrombin onto the Peltier plate held at 37° C.

Ink Formulations

Two inks were required for 3D bioprinting of perfusable PT models. The two inks were prepared as described in Example 2 above.

Bioprinting of 3D Perfusable Proximal Tubule Constructs

3D PT constructs were fabricated using a custom-designed, multimaterial 3D bioprinter equipped with four independently addressable printheads mounted onto a 3-axis, motion-controlled gantry with a build volume of 725 mm×650 mm×125 mm (AGB 10000, Aerotech Inc., Pittsburgh, Pa. USA). Inks were housed in separate syringe barrels to which nozzles of varying size (i.e., 50 μm-410 μm diameter) were attached via a luer-lock (EFD Inc., East Providence, R.I., USA). Inks were extruded through deposition nozzles by applying air pressure (800 Ultra dispensing system, EFD Inc., East Providence, R.I., USA), ranging from 10-90 psi, corresponding to print speeds between 1 mm/s and 5 cm/s.

To create the customized perfusion chip gasket, the silicone ink was deposited through a tapered 410 μm nozzle onto 50 mm×75 mm glass slides. The gasket design was created using a custom MATLAB script that generated G-code for a final gasket structure. After printing, the perfusion chip gasket was cured at 80° C. in an oven for >1 h and stored at room temperature prior to use.

Patterning 3D PTs within the perfusion chip required a combination of casting the ECM and printing the fugitive ink. First, an ECM solution composed of 10 mg/mL fibrinogen, 7.5 wt % gelatin, 2.5 mM $CaCl_2$ and 0.2 wt % TG was equilibrated at 37° C. for 15-20 min before use to improve optical clarity of the ECM, as described above in Example 2. Next, the solution was rapidly mixed with thrombin at a ratio of 500:1, resulting in a final thrombin concentration of 1 U/mL. Immediately after rapid mixing, the ECM solution was cast onto the base of the perfusion chip. Within 2 min at 37° C., polymerization of fibrinogen into fibrin gel ensued. The base ECM layer was then allowed to dry slightly under nitrogen, such that it formed a flat surface. The fugitive Pluronic F127 ink (with 100 U/mL thrombin) was printed on the base ECM layer in the form of a convoluted filament (tubule) using a tapered 200 μm nozzle. A custom Python script (MeCode) was used to specify the toolpath in G-code. Directly after fugitive ink printing, metal hollow perfusion pins interfaced through the silicone gasket were brought into contact with the printed ink. A top layer of ECM was then formed by casting the ECM solution over the printed tubule, as described above. If cells, such as HNDFs, were incorporated in the ECM (FIG. 37), they were mixed in directly after the equilibration period, prior to thrombin mixing and subsequent casting. After the top ECM layer was cast, the construct was held at 37° C. for 1 h to allow fibrin polymerization to terminate and TG to crosslink the network. The construct was then cooled to 4° C. for 15-20 min to liquefy the printed fugitive ink, which was flushed out of the device using cold cell media, leaving behind open conduits that serve as the desired tubular network embedded within the ECM with or without cells in the extratubular ECM space.

Figure 38:
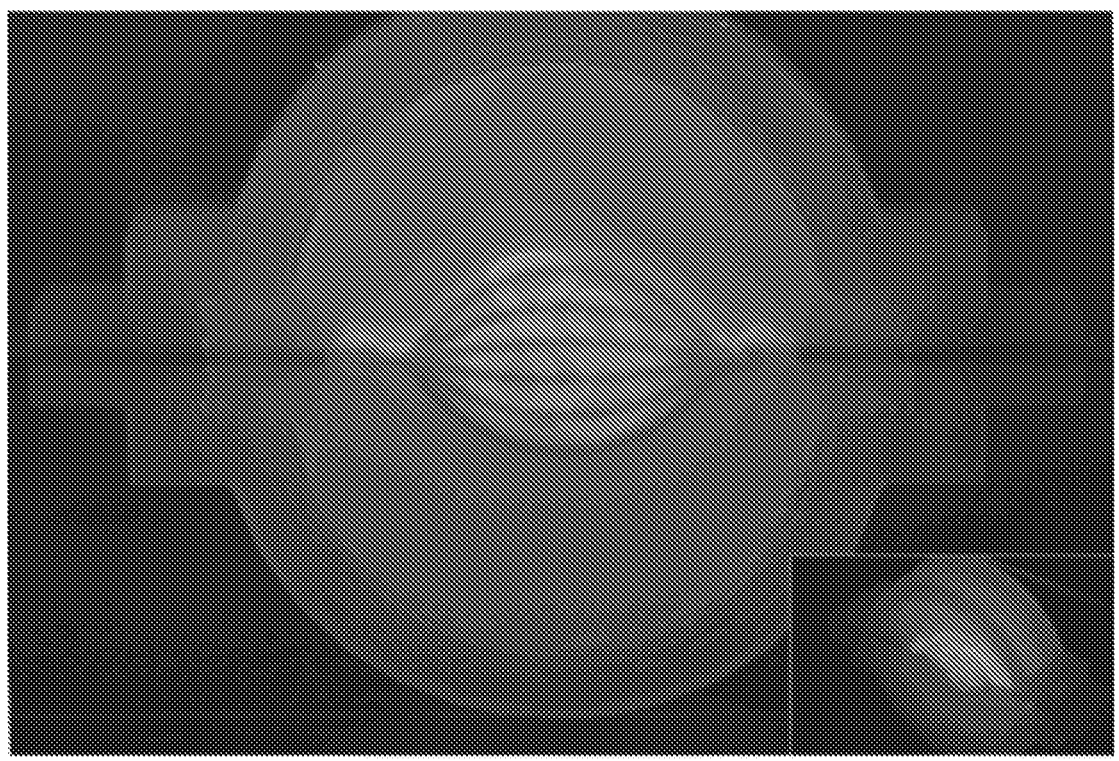
FIG. 38 depicts a PT model constructed with 3 layers of independently addressable perfusable tubes.

Further, these tubular architectures can be assembled layer-by-layer to create 3D architectures. For example, the three layer structure shown in FIG. 38 was constructed using all the same methods, except that each layer was given only 20 min to gel at 37° C. before the next layer fugitive ink was printed and more ECM was cast. The insert of FIG. 38 shows the 3 pins connected to 3 separate tubes perfused with fluorescent dyes. This multi-layer model is a demonstration showing how bioprinting can be combined with microfluidics to interface vascular layers and proximal tubules in 3D. Furthermore, all layers were evacuated after construction. Aqueous based risk reactor dyes were perfused in through the channel and excited with UV light for visualization.

Each 3D PT construct was placed onto a machined stainless steel base and a thick acrylic lid was placed on top. The lid and base were clamped together by four screws, forming a seal around the printed silicone gasket. Next, sterile two-stop peristaltic tubing (PharMed BPT, 0.25 mm internal diameter) was filled with media and connected to the outlet of a sterile filter that was attached to a 10 ml syringe barrel (EFD Nordson), which served as a media reservoir. PTEC media (designed for growth, so ATCC formulation plus 1% FBS, 1% aprotinin, and 1% anti-anti) that has been θequilibrating for >3 h in an incubator at 37° C., 5% $CO_2$ was added to the media reservoir, and tubing from the reservoir was connected to the outlet of the chip (metal hollow perfusion pin). To complete the perfusion circuit, silicone tubing from the reservoir was connected to the inlet metal perfusion pin on the chip. Hose pinch-off clamps were added at the inlet and outlet of the perfusion chip to prevent uncontrolled flow when disconnected from the peristaltic pump, which can damage the epithelium or introduce air bubbles into the system. The media reservoir was equilibrated with atmospheric conditions in the incubator at all times by means of a sterile filter on top of the media reservoir.

Cell Culture

Human immortalized PTECs (RPTEC/TERT1, ATCC CRL-4031) were cultured per ATCC's instructions and were used for all PT model studies up to passage 20. For gene expression analysis, human primary RPTEC (Cell Science), immortalized PTECs (RPTEC-TERT1, Evercyte) and A498 (ATCC HTB-44) renal cancer cells were used and cultured per supplier's instructions. Human neonatal dermal fibroblasts (HNDF), GFP expressing (Angio-Proteomie) were cultured per supplier's instructions and used up to passage 15.

Gene Expression Analysis

Human primary RPTEC (Cell Science), immortalized RPTEC-TERT1 (Evercyte) and A498 (ATCC HTB-44) renal cancer cells were grown in 96-well plates according to supplier's instructions and collected at Day 3 post-confluency by replacing culture medium with 100 μl/well of 1×RNA lysis mixture (QuantiGene® Sample Processing Kit, QS0101). Then 40 μl of lysate was mixed with an mRNA-capture magnetic bead set (Panomics QuantiGene® Plex Set 12631, catalog number 312631), incubated overnight, processed for branched DNA amplification, and analyzed according to the manufacturer's instructions (Panomics QuantiGene® Plex Assay kit, QP1015). The PPIB probe was used as a housekeeping gene for normalization. Fluorescence Intensity (FI) data were presented as average and standard deviation of 3 biological replicates.

Cytokine Analysis of Media Perfusate

Media perfusate was collected from a tubule over a period of 25 days post cell seeding and stored at −80° C. prior to analysis. For cytokine profiling, supernatants were thawed on ice, diluted 2× in sample dilution buffer (BioRad catalog # M60-009RDPD) and analyzed by Luminex technology-based ELISA using the Bio-Plex Pro™ Human Chemokine IL-6 (Set #171BK29MR2), IL-8 (Set #171-BK31MR2) and MCP-I (Set #171-BK36MR2) and the Bio-Plex® 200 Systems (BioRad), according to the manufacturer's instructions. Data were reported as average cytokine concentrations and standard deviations of technical triplicates.

Epithelialization and Longitudinal Culture

Figures 39A, 39B, 39C, 39D, 39E, 39F, 39G, 39H, 39I, 39J, 39K:
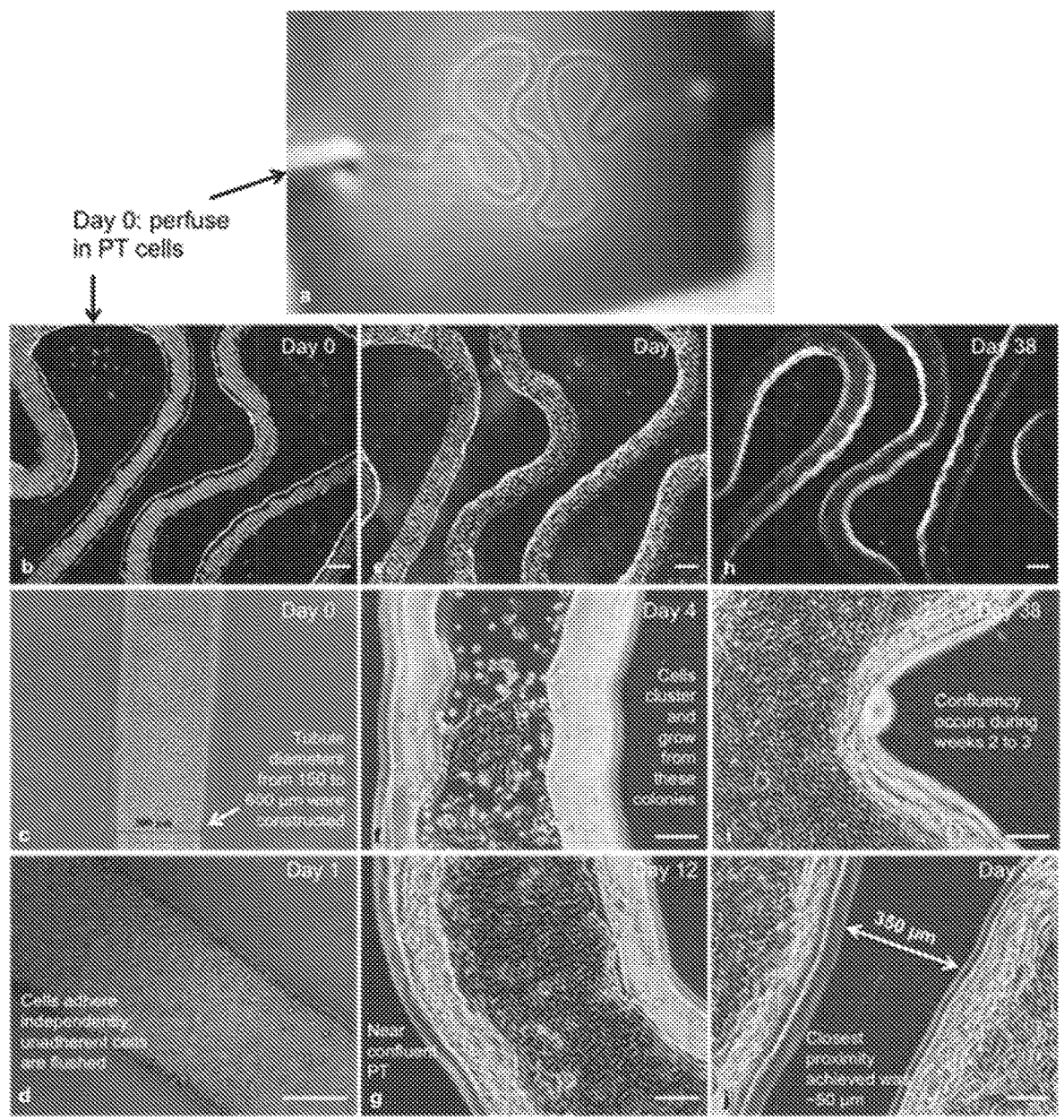

Each printed 3D PT construct was perfused for several hours with PTEC media in the incubator prior to cell loading/seeding. PTECs (PTEC/TERT1, ATCC) were trypsinized from their culture dish and concentrated in media to ~2×10⁷ cells/mL. The cell suspension was then loaded into the perfusion chip through the outlet (FIGS. 39B and 39C). The loaded construct was placed laterally in the incubator for several hours and then flipped 180° and incubated in the tubule with no flow overnight. The next day, non-adherent cells were flushed out of the tubule under flow by gravity. Perfusion of fresh media was then started and the remaining cells began to cluster and then grew from those colonies (FIG. 39F) until they reached confluency at around 3 weeks post seeding (FIG. 39K). During the growth phase, PTECs were fed PTEC media prepared per ATCC guidelines plus 1% aprotinin (EMD Millipore, used to slow down the degradation of the ECM), 1% fetal bovine serum (FBS), and 1% antibiotic-antimycotic (Gibco). After maturation, FBS was removed, and PTECs packed into a tight epithelial monolayer (not shown). At Day 1 post-seeding, the PTECs were exposed to continuous, unidirectional flow at 1 μL/min, equating to shear stresses that varied between 0.1 and 0.5 dynes/cm² depending on the tubule cross section. Media was fed via a peristaltic pump in a closed loop circuit and changed every 2 days.

Albumin Uptake Study

Albumin uptake is assessed for the printed 3D PT models as well as 2D controls. The first control consists of PTECs grown on tissue culture plastic, while the second control consists of PTECs grown on our ECM. In each case, PTECs are grown to confluency and allowed to mature in serum free media. Human serum albumin conjugated with FITC (HSA-FITC, Abcam ab8030) is suspended in PTEC media at 50 μg/mL. All samples are incubated with HSA-FITC in their media for 2 h (in the case of perfusion, it is perfused through the open lumen). After exposure, all samples are washed with 3× volume and then trypsinized with 10× trypsin to collect the individual cells. Cells are fixed and counterstained with primary and secondary antibodies for megalin. Table 2 lists the specific antibodies used.

TABLE 2

| Antibody or stain: | Source | Catalog # | Host Species & Reactivity | Concentration |
|---|---|---|---|---|
| Megalin | abcam | ab76969 | Rabbit anti-human | 1:300 |
| AQP1 | Santa Cruz | SC25287 | Mouse anti-human | 1:300 |
| Na/K ATPase | abcam | ab76020 | Rabbit anti-human | 1:400 |
| Acetylated alpha tubulin | abcam | ab24610 | Mouse anti-human | 1:300 |
| Antibody to laminin | abcam | ab11575 | Rabbit anti-human | 1:250 |
| K Cadherin | abcam | ab133632 | Rabbit anti-human | 1:200 |
| ActinGreen | Life Technologies | R37110 | N/A | 2 drops per mL |
| NucBlue | Life Technologies | R37605 | N/A | 2 drops per mL |

Cells from those samples, and naked cells, are analyzed by flow cytometry (BD LSR Fortessa) and data is collected from n=10,000 cells per sample. To obtain images of HSA-FITC and megalin in PTECs, samples are fixed in place with formalin instead of being trysinized after the wash step. Those samples are counterstained for megalin and imaged using confocal microscopy (Zeiss LSM710).

Cyclosporine A testing

The toxic effect of CysA on PTECs in both the 2D controls and printed 3D PTs was explored. In 2D, cells were seeded in a 96-well format on tissue culture plastic and grown to confluency. They were fed media per ATCC's guidelines. CysA (Sigma-Aldrich, SML1018) was suspended in their media at various concentrations and incubated with cells for 24 h. A viability assay using (3-(4,5-dimethylthiazol-2-yl)-5-(3-carboxymethoxyphenyl)-2-(4-sulfophenyl)-2H-tetrazolium) in the presence of phenazine methosulfate (MTS) was run at the 24 h mark post exposure. This assay was completed on PTECs at early confluency, by giving CysA to the cells on the day they reached confluency, as well as late confluency, by giving CysA several days after they reached confluency. Notably, the toxicity results were similar for each case (FIG. 40N). For 3D PTs, CysA was fed at various concentrations through the open lumen of mature tubules after reaching confluency (at ~3 week mark), where no serum was included in the media for a minimum of 10 days. At the 24 h mark post CysA exposure, a FITC-dextran leak test (described below) was performed to assess and quantify perturbations to the barrier function of PTECs. Directly following, the PT was fixed using 10% buffered formalin for 1 h and counterstained for actin and DAPI as provided in Table 2 above (specific stains).

Diffusional Permeability Measurements

To assess barrier function of the epithelium in 3D, diffusional permeability was quantified by perfusing PTEC media in the open lumen containing 25 μg/mL FITC-conjugated 70 kDa dextran (FITC-Dex, Sigma product 46945) at a rate of 15 μL/min for 3 min and 1 μL/min thereafter for ~30-45 min. The entire test was performed under live cell imaging with both the tubule and the surrounding ECM in the field of view (FIGS. 41A-41E). The diffusion pattern of FITC-Dex was detected using a wide-field fluorescent microscope (Zeiss Axiovert 40 CFL). Fluorescence images were captured before perfusion and every 3 to 5 min over a 30-45 min period. Diffusional permeability of FITC-Dex was calculated by quantifying changes in fluorescence intensity over time using the following equation (Price, G. & Tien, J. in Biological Microarrays, Vol. 671. (eds. A. Khademhosseini, K.-Y. Suh & M. Zourob) 281-293 (Humana Press, 2011));

$$P_d = \frac{1}{I_1 - I_b}\left(\frac{I_2 - I_1}{t}\right)\frac{d}{4}$$

$P_d$ is the diffusional permeability coefficient, $I_1$ is the average intensity at an initial time point, $I_2$ is an average intensity at t~30-45 min, $I_b$ is background intensity (image taken before perfusion of FITC-Dex), and d is the diameter of the channel.

Electron Microscopy

For transmission electron microscopy (TEM), PTECs in 2D or 3D architectures were fixed using 2.5% glutaraldehyde, 1.25% paraformaldehyde, and 0.03% picric acid in 0.1 M sodium cacodylate buffer (pH 7.4) for a minimum of several hours. Small samples (1 mm×1 mm) were removed and washed in 0.1 M cacodylate buffer and bathed in 1% osmiumtetroxide ($OsO_4$) (EMS) and 1.5% potassiumferrocyanide ($KFeCN_6$) (Sigma) for 1 h, washed in water 3× and incubated in 1% aqueous uranyl acetate (EMS) for 1 h followed by 2 washes in water and subsequent dehydration in varying grades of alcohol (10 min each; 50%, 70%, 90%, 2×10 min 100%). The samples were then placed in propyleneoxide (EMS) for 1 h and incubated overnight in a 1:1 mixture of propyleneoxide and TAAB Epon (Marivac Canada Inc. St. Laurent, Canada). The following day the samples were embedded in TAAB Epon and polymerized at 60° C. for 48 h. Ultrathin sections (about 60 nm) were cut on a Reichert Ultracut-S microtome, placed on copper grids stained with lead citrate and examined in a JEOL 1200EX Transmission electron microscope and images were recorded with an AMT 2k CCD camera. Image analysis was performed using ImageJ software.

For scanning electron microscopy (SEM), perfused PTECs in 3D were fixed using 10% buffered formalin for 1 h. The samples were thinly sliced (~1 mm thick) to expose cells circumscribing the open lumen. The fixative was washed away using PBS×2 and subsequent dehydration in varying grades of ethanol (20 min each; 30%, 50%, 70%, 90%, 3×20 min 100%). The samples were then placed in 50% ethanol and 50% hexamethyldisilazane (HMDS) for 30 min followed by 100% HMDS 3×30 min. All steps were performed in a closed and sealed glass container. After the final washing with HMDS, the samples were removed and placed in an open container under $N_2$ in the fume hood to dry. Dried samples were mounted to aluminum pin mounts using conductive carbon tape, sputter coated with gold, and imaged with a Tescan Vega SEM.

Immunostaining

Immunostaining followed by confocal microscopy was used to assess the cellular localization of proteins in 2D and 3D PTEC models. Prior to immunostaining, each construct was washed with PBS and then fixed for 20 min to 1 h using 10% buffered formalin. The fixative was removed using several washes in PBS for several hours and then blocked overnight using 1 wt % bovine serum albumin (BSA) in PBS. Primary antibodies to the cell protein or biomarker of interest were incubated with the constructs for 1 day at the dilutions listed in Table 2 above in a solution of 0.5 wt % BSA and 0.125 wt % Triton X-100. Removal of unbound primary antibodies was accomplished using a wash step against a solution of PBS or 0.5 wt % BSA and 0.125 wt % Triton X-100 in PBS for 1 day. Secondary antibodies were incubated with the constructs for 1 day at the dilutions listed in the Table above in a solution of 0.5 wt % BSA and 0.125 wt % Triton X-100 in PBS. Samples were counter-stained with NucBlue or ActinGreen for 2 h and then washed for 1 day in PBS prior to imaging.

Image Rendering and Analysis

Phase contract microscopy was performed using an inverted Leica DM IL scope with objectives ranging from 1.25× to 40×. Confocal microscopy was performed using an upright Zeiss LSM 710 with water immersion objectives ranging from 5× to 40× employing spectral lasers at 405, 488, 514, 561, and 633 nm wavelengths. Image reconstructions of z-stacks were performed in ImageJ using the z-projection function with the maximum pixel intensity setting. Any increases in brightness were performed uniformly across an entire z-projected image. 3D image reconstructions were performed using Imaris software. The new CytoSMART (Lonza) in incubator system was used to capture time-lapse imaging (not shown). Image analysis for quantification of diffusional permeability was performed using custom MATLAB scripts employing previously reported methods (Price, G. & Tien, J. in Biological Microarrays, Vol. 671. (eds. A. Khademhosseini, K.-Y. Suh & M. Zourob) 281-293 (Humana Press, 2011)). TEM image analysis was performed using ImageJ software to measure cell height (n≥50), microvilli density (n≥25), and microvilli length (n≥200) over at least 3 independent samples for each condition.

Statistical Analysis

Data were expressed as means±standard deviation. Statistical analysis was performed using MATLAB and statistical significance was determined at a value of $p<0.05$ as determined by an ANOVA using Tukey's multiple pairwise comparison test. Different significance levels (p values) were indicated with asterisks and specific p values were provided in each figure legend.

Results

Printing, Seeding, and Longitudinal Culture of 3D Proximal Tubules

Figures 36A, 36B, 36C, 36D, 36E, 36F:
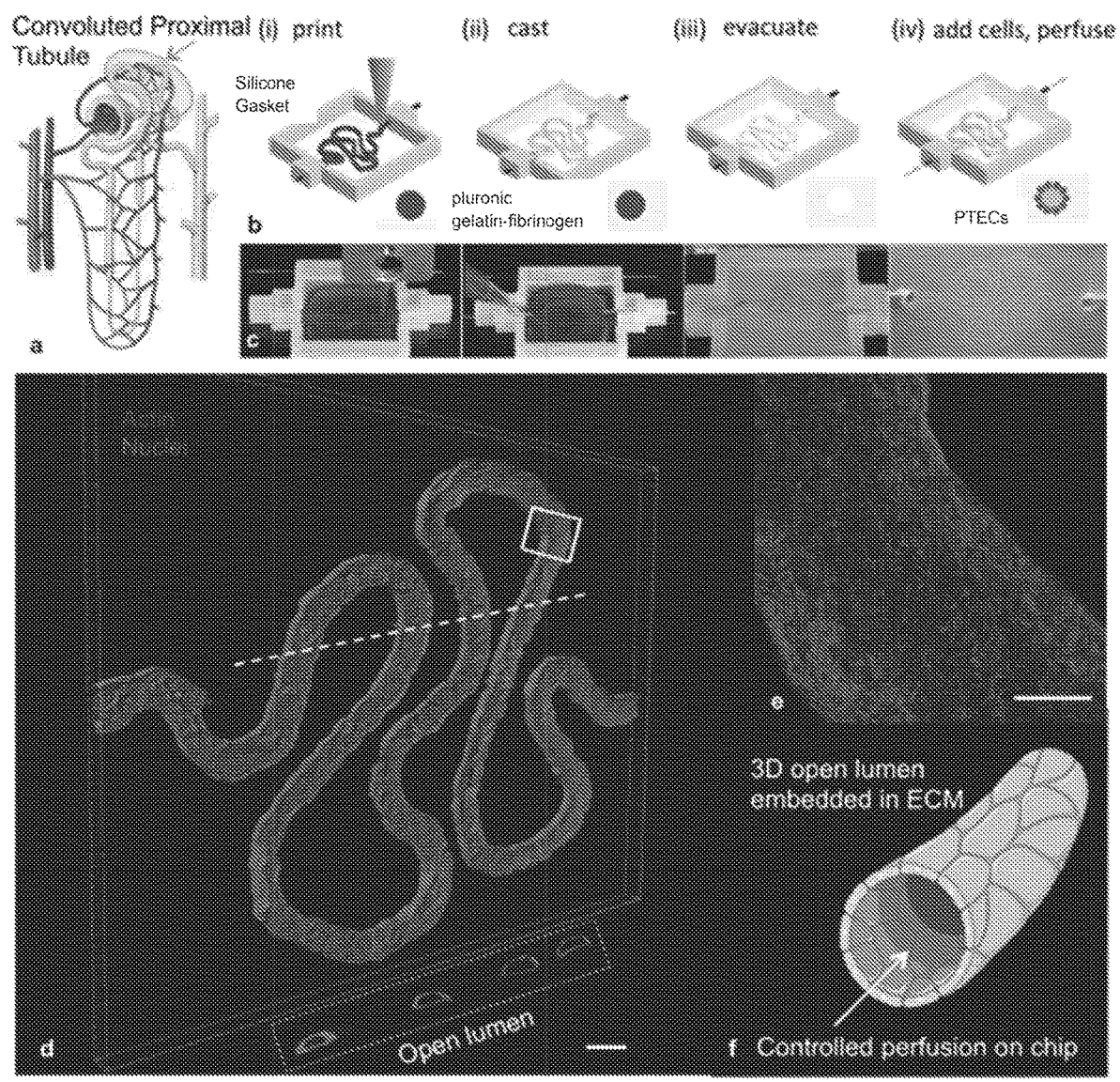
FIG. 36A depicts a Schematic of a nephron highlighting the convoluted proximal tubule.
FIGS. 36B and 36C depict schematics and images of different steps in the fabrication of 3D convoluted, perfusable proximal tubules, in which a fugitive ink is first printed on a gelatin-fibrinogen extracellular matrix, ECM (i), additional ECM is cast around the printed feature (ii), the fugitive ink is evacuated to create an open tubule (iii), and PTEC cells are seeded within the tubule and perfused for long time periods (iv).
FIG. 36D depicts a 3D rendering of the printed convoluted proximal tubule acquired by confocal microscopy.
FIG. 36E is a higher magnification view of the region in FIG. 36D denoted by the white rectangle, scale bar=200 μm.
FIG. 36F depicts a schematic showing the result of the fabrication process where an open lumen circumscribed with an epithelial lining is created in 3D and directionally perfused on chip.

The described bioprinting method was used to construct a 3D convoluted proximal tubule segment of a nephron, as depicted in FIG. 36A. First, as shown in FIGS. 36B and 36C, a silicone gasket was printed on a glass slide that demarcates the outer border of the 3D tissue chip. A layer of engineered extracellular matrix (ECM), which was composed of a gelatin-fibrin hydrogel (Kolesky, D. B., et al., *Proc. Natl. Acad. Sci. U.S.A.* (2016)), was then evenly deposited within the gasket. Next, a fugitive ink, shown in pink, was printed onto the ECM layer. The term "fugitive ink" refers to a printed material that will ultimately be liquefied and removed from the final 3D PT construct. After printing, the fugitive ink was connected to hollow metal pins interfaced through the gasket walls and additional ECM was cast over the printed structure. The 3D tissue model was then housed within a perfusable chip, where it was cooled to 4° C. to liquefy and subsequently remove the fugitive ink yielding an open convoluted tubular channel embedded within the ECM. Finally, cell media was perfused through the 3D convoluted tubular architecture on chip via an external peristaltic pump. Notably, the described method can create 3D proximal tubule models in myriad configurations with precisely controlled size, curvature, and location. For instance, if multiple tubules are required to increase statistical relevance of an assay or provide basal-side access channels, they can be printed alongside one another (see FIGS. 42A and 42B) and can be perfused independently or through a single inlet. As shown in FIGS. 42A and 42B, multiple PTs can be printed in parallel and lined with PTEC cells that grow to confluency.

The composition and rheological properties of the ECM and fugitive ink were specifically tailored for the described biofabrication method. The ECM consisted of fibrinogen, gelatin, and two enzymes (thrombin and transglutaminase), as described in Example 2. The dual enzyme scheme enabled rapid solidification of the ECM around printed features, through thrombin action on fibrinogen to make fibrin. The second enzyme, transglutaminase, provided a slower crosslinking of gelatin with fibrin, enabling a seamless integration of the upper and lower ECM layers during assembly (see FIG. 43A). Furthermore, the elastic modulus of the ECM (~3.5 kPa) mimicked that of the cortex of a healthy kidney (~4 kPa) (Bensamoun, S. F., Robert, L., Leclerc, G. E., Debernard, L. & Charleux, F. Stiffness imaging of the kidney and adjacent abdominal tissues measured simultaneously using magnetic resonance elastography. Clin. Imaging 35, 284-287 (2011)); both matrix stiffness and composition were important for the retention of tissue-specific cell functionality (Jansen, J. et al. Biotechnological challenges of bioartificial kidney engineering. Biotechnol Adv 32, 1317-1327 (2014); and Furness, P. N. Extracellular matrix and the kidney. J. Clin. Pathol. 49, 355-359 (1996)). The fugitive ink was composed of a triblock copolymer of polyethylene-polypropylene-polyethylene (Pluronic® F127), which formed a viscoelastic gel above a critical micelle concentration in water at room temperature. This ink exhibited a gel-to-fluid transition as the perfusable tissue chip was cooled to 4° C., enabling its removal from the ECM under those conditions (Kolesky, D. B. et al., Adv. Mater. 26, 3124-3130 (2014); and Wu, W., et al, Adv Mater 23, H178-183 (2011)). The fugitive ink also contained a high concentration of thrombin (100 U/mL). When this ink was surrounded by ECM during the casting process, soluble fibrinogen was rapidly transformed to insoluble fibrin, templating fibrin around the lumen and facilitating the desired, long-term perfusion of cell media.

Prior to introducing cells, the 3D tissue chip was perfused with cell media overnight at 37° C. to remove any residual fugitive ink or enzymes and equilibrate the matrix at 37° C. and 5% $CO_2$ in the incubator. PTEC-TERTI cells were introduced that consisted of human proximal tubular cells immortalized through stable expression of the catalytic subunit of human telomerase reverse transcriptase (TERT) (Wieser, M. et al., American journal of physiology. Renal physiology 295, F1365-1375 (2008)). PTEC-TERTI were developed as a cell model that maintains morphological and functional properties of primary PTEC cells with an additional replicative advantage over primary cells that have a finite lifespan in vitro due to telomere shortening. Genomic stability of PTEC-TERTI up to 90 population doublings has been demonstrated (Wieser, M. et al. (2008)). The PTEC-TERTI was profiled by carrying out gene expression analysis on 33 key PTEC genes and compared them with primary PTEC and the renal cancer cell line A498 (FIG. 43B). The mRNA levels demonstrated that PTEC-TERTI cells were transcriptionally close to primary renal PTEC cells. Given the need for scalable, stable cellular systems in drug discovery and safety platforms, we optimized the described 3D PT model with PTEC-TERTI (hereby referred to as PTECs).

To circumscribe the convoluted tubules with a confluent PTEC monolayer, the cells were first trypsinized from a tissue culture plastic dish, concentrated, and perfused into the open lumen of the printed structure. The cells were incubated in the tubule overnight with no flow to facilitate adherence to the ECM and are then flushed lightly at Day 1 to remove any non-adherent cells. A time sequence of their maturation process in the tubule is provided in FIGS. 39A-39K. Notably, PTECs grow to confluency within the tubule, circumscribing the open lumen in 3D over a period of approximately 3 weeks (FIG. 39K). Furthermore, since PTECs actively participate in pro-inflammatory cytokine production in vivo and in vitro, we measured the accumulation of IL6, IL-8 and MCPI in the tubule perfusate over time. The cytokine profile showed distinct concentrations in the growth and maturation phase, suggesting the tubule stabilized after confluency (FIGS. 44A-44C). The light grey bars in FIGS. 44A-44C represent the growth phase of the tubule. At Day 12, the tubule is near confluency, FBS is removed from the media, and the profile of the confluent tubule is shown in dark grey bars. Note that once confluency is reached and FBS is removed, cytokine levels stabilize. Moreover, the decrease of IL-6 concentration after serum removal was consistent with the previously reported inductive effect of albumin on IL-6 production in primary human PTECs (Pearson, A. L., Colville-Nash, P., Kwan, J. T. & Dockrell, M. E. Albumin induces interleukin-6 release from primary human proximal tubule epithelial cells. JN journal of nephrology 21, 887 (2008)).

Figure 37:
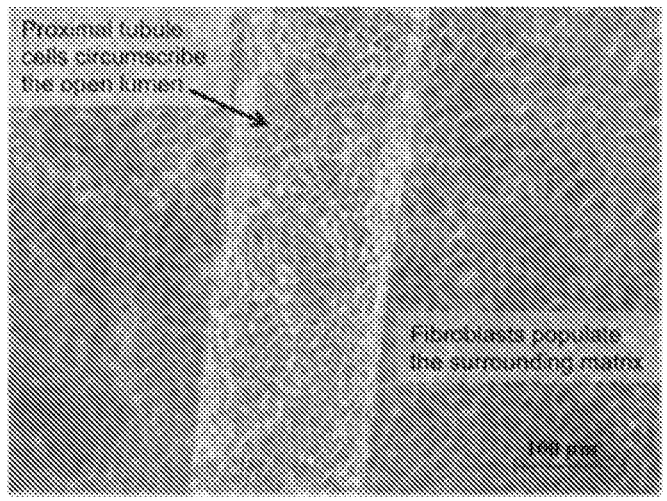
FIG. 37 depicts a 3D proximal tubule lined with PTEC cells and embedded in a fibroblast-laden extracellular matrix (phase contrast image of a 3D PT grown to a confluent epithelium, in which fibroblasts thrive in the surrounding ECM, scale bar=100 μm).

For increasing levels of complexity, support cells, such as fibroblasts or immune cells, can be suspended in the ECM surrounding the printed tubules. As shown in FIG. 37, fibroblasts can survive adjacent to the tubule in the extratubular space of the ECM. Tubule diameters ranging from 150 μm to 700 μm have been printed; assays and quantitative measurements shown here were carried out on PTs with diameters ranging from 400 μm to 550 μm under a flow rate of ~1 μL/min. Images of a mature PT at low (FIG. 36D) and higher magnifications (FIGS. 36E and 36F) reveal that PTECs circumscribe the lumen and adopt a cuboidal morphology, as expected for their in vivo phenotype.

Specifically, FIG. 36D depicts a 3D rendering of the printed convoluted proximal tubule acquired by confocal microscopy (actin is stained in red and nuclei are blue); the white dotted line denotes the location of the cross-sectional view shown below in which PTEC cells circumscribe the open lumens in 3D, scale bar=500 μm. FIG. 36E is a higher magnification view of the region in (d) denoted by the white rectangle, scale bar=200 μm. FIG. 36F is a schematic showing the result of the fabrication process where an open lumen circumscribed with an epithelial lining is created in 3D and directionally perfused on chip.

These engineered 3D convoluted PTs were maintained longitudinally by feeding media in a closed loop system. Media was replaced every two days and the tubules remain viable for extended periods; the longest period tested exceeds two months (65 days).

3D Proximal Tubules Form a Tissue-Like Polarized Epithelium

After PTECs were seeded and grown to maturity in the tubule, a combination of light microscopy, scanning electron microscopy (SEM) and transmission electron microscopy (TEM) were used to characterize the printed and perfused 3D PT (FIGS. 45A-46K and 46A-46G).

FIGS. 45A-45K depict proximal tubule morphology and molecular markers: (A) A phase contrast image of a mature 3D PT construct taken at 6 weeks, scale bar=500 μm, (B) phase contrast image of the 3D PT construct at 6 weeks, scale bar=250 μm, (C) TEM image of the PTECs within the tubule at 5 weeks, scale bar=5 μm, (D) TEM image of the PTECs grown on a 2D dish coated with ECM with no perfusion, scale bar=5 μm, (E) schematic view of the columnar epithelium seen in native tissue, in which PTECs pack together closely and exhibit a dense brush border on the apical side, tight junctions, and a solid basement membrane, reprinted with permission (Mescher, A. in Junqueira's Basic Histology: Text and Atlas, Edn. 1385 (McGraw-Hill Education, 2013)) (F) PTEC cell height as measured from TEM images of the 3D PT constructs (3DP) as well as three 2D controls (2DP=PTECs on ECM in 2D with perfusion, 2D=PTECs on ECM in 2D not perfused, Dish=bare tissue culture dish not perfused), *p<0.001, **p<0.02, (G) SEM images at low (scale bar=50 μm) and higher (scale bar=20 μm) magnifications showing a confluent layer of PTECs within the 3D PT, white arrows highlight the presence of primary cilia at a density of one per cell, (H) 3D rendering of a partial tubule showing the apical side, which highlights the primary cilia (red), scale bar=20 μm, (I) image of the PT highlighting the presence of Na/K ATPase in green, scale bar=100 μm, (J) image of the 3D PT highlighting the presence of AQPI in yellow, scale bar=100 μm, (K) high magnification view of the image in (j) highlighting actin in red and showing AQPI in yellow, scale bar=20 μm.

Specifically, low (FIG. 45A) and high (FIG. 45B) magnification views in phase microscopy reveal that PTECs grow throughout the tubule packing together in a columnar fashion. TEM images of the tubule cross-section further show that PTECs assemble into a tightly packed, columnar renal tubular epithelium (FIGS. 45C and 45D). As shown schematically in FIG. 45E, the epithelium should have a basement membrane formed on the basal side and a brush border of microvilli on the apical side facing the open lumen with cells in a columnar morphology. From the TEM images, the increase in cell height was quantified, owing to the columnar cell morphology within the 3D proximal tubule (FIG. 45C) compared to the same cells grown for the same duration in 2D on ECM without perfusion (FIG. 45D). Importantly, the PTECs in the printed and perfused 3D PT constructs exhibited a two-fold increase in cell height relative to the planar controls without perfusion and a 40% increase relative to perfused 2D controls on our ECM (FIG. 45F).

SEM images of the apical side of the 3D PT (FIG. 45G) reveal the formation of a confluent cell layer and the presence of primary cilia (one per cell, akin to that observed in vivo). The primary cilium is a sensory organelle that extends into the open lumen and responds to shear stress; it is important for the maintenance of the epithelial cell phenotype and is often lost once cells are isolated and cultured in 2D in the absence of shear stress) Jang, K. J. et al. Human kidney proximal tubule-on-a-chip for drug transport and nephrotoxicity assessment. *Integrative biology: quantitative biosciences from nano to macro* 5, 1119-1129 (2013)). Primary cilia were also observed in the described PT using immunofluorescence, by staining for acetylated tubulin (shown in red in the 3D rendering in FIG. 45H and FIGS. 47A and B). Furthermore, we confirmed the expression of the epithelial marker Na+/K+ ATPase (FIGS. 45H and 45I), and its appropriate sub-cellular localization to the basolateral plasma membrane (FIG. 47A), which is again akin to the in vivo PTEC phenotype. The proximal tubule-specific (versus distal tubule) water channel Aquaporin I (AQPI) was also predominant throughout the tubule (FIG. 45J) and the AQPI staining at higher magnification has a speckled pattern on the membrane surface (FIG. 45K).

Cell polarity is a fundamental feature of epithelial cells and is crucial to ensure vectorial transport by PTECs. Hence, we explored PTEC polarity by first characterizing the apical side of our 3D PT using TEM (FIG. 46A). At the apical surface, microvilli were present and formed a brush border that is more pronounced than in 2D (compare FIG. 46A and FIG. 45C with FIG. 45D). At the basal (FIG. 46B) surface, basolateral interdigitations (BI) are prominent. These BI extend the surface area of the lateral and basal borders in vivo; cells in 2D (FIG. 45D) were mainly flat and lacked BI. Presence of circular invaginations in the lateral membrane, annotated with white arrows in FIG. 46B, suggests that mechanisms of active transport are present at the lateral surface. Furthermore, there is a distinct difference between the morphology of the ECM and basement membrane (BM) proteins deposited by the PTECs. Further exploration of the BM protein composition revealed that in mature 3D PT constructs, PTECs deposited laminin and collagen IV (FIG. 46C). Other important properties observed were the presence of tight junctions between neighboring cells in TEM (FIG. 46D) and the presence of cell-cell junction proteins, such as K cadherin in FIG. 46E, that link cells in a characteristic cobblestone pattern. Lastly, properties of the brush border were quantified by TEM image analysis. The average microvilli length in the 3D printed and perfused PTs was found to be ~200% longer than the 2D non-perfused and ~40% higher than the 2D perfused controls (FIG. 46F). Concurrently, microvilli density was also significantly higher for the printed and perfused 3D PT constructs compared to all 2D control conditions (all 2D controls were statistically similar) (FIG. 46G).

PTECs will form near leak tight barriers against the traffic of certain proteins, like high molecular weight dextran, when healthy and confluent. Barrier function was assessed by traditional methods (Price, G. & Tien, J. in Biological Microarrays, Vol. 671. (eds. A. Khademhosseini, K.-Y. Suh & M. Zourob) 281-293 (Humana Press, 2011)). Specifically, FITC-labeled dextran (70 kDa) was perfused through the open lumen of mature PTs and the intensity of fluorescence was captured using a wide-field fluorescence scope with time. From the FITC intensity values, the diffusional permeability was calculated and compared against a 3D tubule without epithelial lining (FIGS. 41A-41E). The drastic reduction in the diffusional permeability coefficient (greater than an order of magnitude) indicated that the epithelial barrier in the printed and perfused 3D PT construct was nearly leak tight and functional.

Albumin Uptake

Receptor-mediated endocytosis by PTEC cells is essential for body fluid homeostasis. Reabsorption of plasma proteins from the glomerular filtrate relies partially on the megalin-cubilin complex located in the brush border (Cui, S., et al. Megalin/gp330 mediates uptake of albumin in renal proximal tubule. *American Journal of Physiology-Renal Physiology* 271, F900-F907 (1996); Gekle, M. Renal proximal tubular albumin reabsorption: daily prevention of albuminuria. *Physiology* 13, 5-11 (1998); and Norden, A. G. et al. Urinary megalin deficiency implicates abnormal tubular endocytic function in Fanconi syndrome. *J. Am. Soc. Nephrol.* 13, 125-133 (2002)) and can be modeled in vitro by monitoring albumin uptake by PTECs. The ability of PTECs, grown either on perfused 3D PT constructs or 2D controls, to uptake FITC-labeled human serum albumin (HSA) was tested. After exposure to FITC-HSA for 2 h, PTECs were collected, stained for megalin expression, and analyzed by flow cytometry. The results for albumin uptake are provided in FIG. 48A. Large populations of cells in the 2D controls exhibit fluorescence intensity similar to the non-fluorescent control, whereas cells lining the perfused 3D PT constructs exhibit a significant increase in the FITC-HSA intensity. Results for megalin, one of the transporters for albumin, show that its expression was also highest in the 3D PT (FIG. 48B). Mean values for the fluorescence intensity of the populations analyzed by flow cytometry are listed in Table 3.

TABLE 3

| Mean Intensity | Albumin | Megalin |
| --- | --- | --- |
| 2D on Plastic | 201 | 571 |
| 2D on Printing Matrix | 310 | 1127 |
| 3D Printed (Perfused) | 1452 | 1670 |

Contrary to the 2D controls, enhanced megalin expression was strongly correlated with superior albumin functional uptake in the perfused 3D PTs, suggesting that both 3D architecture and perfusion improve epithelial function likely due to enhanced cell polarity and brush border (FIGS. 46A-46G). Lastly, images of FITC-HSA (FIG. 48C), megalin (FIG. 48D), and the combination thereof (FIG. 48E) reveal an overlapping distribution of albumin and megalin in PTECs that line the 3D PT. Thus, the described, engineered 3D PT constructs exhibit superior albumin uptake function relative to either 2D control.

Drug Toxicity Testing

Cyclosporine A, a drug commonly given following transplant surgery to prevent rejection, is a known nephrotoxin that damages proximal tubule cells. To study its effect on the perfused 3D PT, 3D PT were exposed to various concentrations of Cyclosporine A (CysA) and alterations of cell morphology and cytoskeleton organization were monitored by immunostaining of actin filaments. Bright field images of the tubules (FIGS. 40A to 40D) and corresponding 3D renderings of actin staining (FIGS. 40E to 40H and FIGS. 40I to 40L) reveal dose-dependent manifestation of CysA-induced damage. Minor breaks in cell-cell junctions (FIG. 49A-D) and reorganization of actin (FIG. 40J) were observed at 10 $\mu$M CysA, whereas discrete areas devoid of cells were readily evident at 50 $\mu$M CysA (FIGS. 40G and 40K) and exacerbated at 100 $\mu$M CysA (FIGS. 40D, 40H, and 40L). We also note that cell layers tightened and buckled at 50 and 100 $\mu$M CysA (FIGS. 40G, 40K and FIG. 39). Finally, CysA-induced disruption of the epithelial barrier function was assessed by quantifying the diffusional permeability of FITC-dextran (70 kDa) in treated tubules. As shown in FIG. 40M, exposure to 50 and 100 $\mu$M CysA increased the epithelial barrier permeability by almost 4-fold and 6-fold, respectively. It was found that the respective cell viability of PTECs grown on 2D culture plastic dishes decreased by 40% and 60% after treatment with 50 and 100 $\mu$M CysA (FIG. 40N). Overall, these results indicate that the 3D PT constructs can be used to qualitatively (immunostaining) and quantitatively (diffusional permeability measurements) assess nephrotoxicity.

Discussion

Recent advances in bioprinting have enabled the creation of pervasive and interconnected channels within engineered extracellular matrices (Kolesky, D. B., et al., Three-dimensional bioprinting of thick vascularized tissues. *Proc. Natl. Acad. Sci. U.S.A.* (2016); Kolesky, D. B. et al. 3D Bioprinting of Vascularized, Heterogeneous Cell-Laden Tissue Constructs. *Adv. Mater.* 26, 3124-3130 (2014); and Miller, J. S. et al. Rapid casting of patterned vascular networks for perfusable engineered three-dimensional tissues. *Nature materials* 11, 768-774 (2012)). It was previously shown that these channels can be lined with endothelial cells and perfused to create tissues with embedded vasculature (Kolesky, D. B., et al. (2016) and Kolesky, D. B., et al. (2014)). A pathway for fabricating perfusable, convoluted 3D proximal tubules via in vitro epithelialization is now developed. Importantly, a controlled unidirectional flow was incorporated to enable longitudinal studies at physiologically relevant shear stresses in our 3D PT model. By simultaneously integrating 3D cell culture, tissue-on-chip, and bioprinting methods, a facile, customizable platform for producing 3D tissues and organ models on chip was created. The ability to programmably define tubule size and geometry, including convolution, surpasses existing 3D PT models that rely on pin pull out generate straight tubules in gels. Moreover, the described, engineered 3D bioprinted PTs enable the collection of hundreds of thousands of cells for analysis, e.g., far greater than the 10,000 cells required for accurate sampling via flow cytometry. By contrast, the quantitative study of high cell populations was previously difficult to achieve in planar microfluidic-based devices (Adler, M. et al. A quantitative approach to screen for kidney toxic compounds in vitro. *J. Am. Soc. Nephrol.* (2015); and Adler, M. et al. A quantitative approach to screen for kidney toxic compounds in vitro. *J. Am. Soc. Nephrol.* (2015)).

Based on this study, more complex constructs in which multiple tubules are patterned alongside one another to facilitate basal side access, vascularization, or the study of crosstalk between PTECs in adjacent channels may be created (FIGS. 42A-B and 38). For example, 3D PTs along with embedded vasculature with integrated podocytes and mesangial cells may be co-printed. iPSC-derived renal progenitors could also be seeded for maturation under 3D perfused conditions. The described, versatile bioprinting method also allows one to incorporate multiple cells types in the extratubular space (FIG. 37), thereby programming predefined levels of complexity required for studying cell-cell interactions.

The engineered ECM, based on enzymatic crosslinking of fibrinogen and gelatin, enables both the formation of tubular printed structures and favorable PTEC matrix interactions. PTECs form a confluent layer that can be sustained for >60 days and exhibit the hallmarks of functional cells in vivo, including many important morphological features and functional markers. Interestingly, 3D printed and perfused constructs show enhanced microvilli length, density, and cell height in comparison to 2D perfused controls. While more extensive studies are required to fully elucidate the origin of these enhancements in the 3D case, several factors such as apical constriction, cell-cell signaling, or shear stress profiles could be investigated.

The described 3D PT constructs can be used to elucidate mechanisms of drug-induced tubule damage prior to cell death, such as weakening of cell-cell junctions, monitoring of real-time wound healing, and studying cellular and molecular aspects of drug transport through the renal barrier. The morphology and function of PTECs seeded within printed 3D tubules whose outer diameter and curvature more closely mimics in vivo PTs may be investigated to probe whether further improvements to the epithelium structure and function are possible (~60 $\mu$m diameter is physiological). It is believed that 3D tubules with smaller diameters may further enhance the observed brush border. Currently, the microvilli are 1.3±0.3 $\mu$m in our 3D PTs, which is significantly higher than the planar controls and approaching the microvilli length found in a rat kidney is 2.73±0.13 $\mu$m.

In summary, the described method combines 3D cell culture, tissue-on-chip, and bioprinting methods to create 3D, convoluted renal proximal tubules embedded within an extracellular matrix on customized perfusion chips. These 3D PT models promote the formation of a tissue-like epithelium with in vivo phenotypic and functional properties relative to the same cells grown in 2D controls. The described bioprinting method opens new avenues for creating 3D tissues on chip that better recapitulate in vivo microenvironments, which could enable advances in drug screening, mechanistic drug studies, disease models, and ultimately, regenerative medicine.

A new approach has been developed and described in the present disclosure for creating vascularized, heterogeneous tissue constructs with epithelium on demand via 3D bioprinting. This highly scalable platform enables the fabrication of engineered tissue constructs in which vasculature, epithelium, multiple cell types and optionally other functional chemical substances, such as drugs, toxins, proteins and/or hormones, are programmably placed at desired locations within an extracellular matrix. This technique may lead to the rapid manufacturing of functional 3D tissues and organs needed for transplant.

The following patents and patent application publications are hereby incorporated by reference in their entirety: International Application No. PCT/US2014/063810, entitled "Method of printing a Tissue Construct with Embedded Vasculature," filed Nov. 4, 2014; International Application No. PCT/US2012/044794, entitled "Multinozzle Deposition System for Direct Write Applications," filed Jun. 29, 2012; U.S. Patent Application Publication No. 2013/0084449, entitled "Viscoelastic Ink for Direct Writing of Hydrogel Structures," which was filed as PCT/US2011/29429 on Mar. 22, 2011; and U.S. Pat. No. 8,101,139, entitled "Microcapillary Networks," filed on Jun. 5, 2008.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method of printing a tubular tissue construct comprising:
depositing one or more sacrificial filaments on or in a substrate to form a functional channel pattern, each sacrificial filament comprising a fugitive ink and a plurality of predetermined types of viable cells, wherein each predetermined type of viable cells is deposited at a different predetermined location along a length of the sacrificial filament;
at least partially surrounding the functional channel pattern with an extracellular matrix composition,
removing the fugitive ink to create one or more functional channels in the extracellular matrix composition, at least a portion of each different predetermined type of viable cells remaining at the different predetermined location after removal of the fugitive ink, thereby forming a tubular tissue construct.

2. The method of claim 1, wherein the tubular tissue construct is a nephron or a tubule portion of the nephron.

3. The method of claim 1, wherein the substrate is a perfusable chip.

4. The method of claim 1, further comprising exposing the tubular tissue construct to one or more biological agents, a biological agent gradient, a pressure, and/or an oxygen tension gradient.

5. The method of claim 4, wherein the one or more biological agents, the biological agent gradient, the pressure, and/or the oxygen tension gradient further direct development, differentiation, and/or functioning of the tubular tissue construct.

6. The method of claim 1, wherein the plurality of predetermined types of viable cells comprise at least two of renal proximal tubule cells, loop of Henle cells, renal distal tubule cells, collecting duct cells, mesangial cells, renal microvascular cells, renal cell progenitors, pluri or multipotent stem cells, other endothelial lineage cells, and fenestrated glomerular endothelial cells.

7. The method of claim 1, further comprising:
depositing a second set of one or more sacrificial filaments on or in the substrate to form an interpenetrating network of tubes, each of the sacrificial filaments of the second set of the one or more sacrificial filaments comprising a second fugitive ink; and
removing the second fugitive ink, thereby forming the interpenetrating network of tubes in the tubular tissue construct.

8. The method of claim 7, further comprising injecting a suspension of viable epithelial or endothelial cells into the one or more tubes.

9. The method of claim 7, wherein the interpenetrating network of tubes comprises a vascular pattern interpenetrating the functional channel pattern.

10. The method of claim 1, wherein the at least partial surrounding of the functional channel pattern with the extracellular matrix composition occurs:
during deposition of the one or more sacrificial filaments, the one or more functional channel patterns thereby being formed and embedded simultaneously in the extracellular matrix composition; or
after the deposition of the one or more sacrificial filaments, the one or more functional channel patterns thereby being formed and embedded after the at least partially surrounding the functional channel pattern with an extracellular matrix composition step.

11. The method of claim 1, wherein each of the one or more sacrificial filaments are extruded through a single printhead before being deposited on or in the substrate.

12. The method of claim 1, wherein when more than one sacrificial filaments are deposited, sacrificial filaments are extruded through multiple printheads.

13. The method of claim 1, wherein the tubular tissue construct is a nephron, intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph.

14. The method of claim 1, further comprising depositing one or more cell-laden filaments each comprising a plurality of viable cells on or in the substrate to form one or more tissue patterns, each of the tissue patterns comprising one or more predetermined cell types.

15. The method of claim 1, further comprising depositing one or more additional filaments each comprising one or more extracellular matrix components on or in the substrate to form a patterned, chemically heterogeneous matrix, wherein the one or more additional deposited filaments are cell laden, each comprising one or more viable cell types.

16. A method of printing a tubular tissue construct comprising:
- depositing one or more sacrificial filaments on or in a substrate to form a functional channel pattern, each sacrificial filament comprising a fugitive ink and a plurality of predetermined types of binding domains, wherein each predetermined type of binding domain is deposited at a different predetermined location along a length of the sacrificial filament and is capable of binding to a predetermined type of target cell;
- at least partially surrounding the functional channel pattern with an extracellular matrix composition,
- removing the fugitive ink to create one or more functional channels in the extracellular matrix composition, at least a portion of the different predetermined types of binding domains remaining at the different predetermined locations after removal of the fugitive ink; and
- injecting a suspension comprising at least one predetermined type of target cells into the functional channel, wherein the target cells bind to corresponding predetermined types of binding domains, thereby forming a tubular tissue construct.

17. The method of claim 16, wherein the binding domains for the target cells are selected from the group consisting of antibodies, peptides, proteins, DNA, RNA, aptamers, nanoparticles, small molecules, chemical functional groups, and bacteria.

18. The method of claim 16, wherein the extracellular matrix surrounding the functional channel pattern contains predetermined coupling moieties to capture the binding domains deposited with one or more sacrificial filaments.

19. The method of claim 18, wherein the coupling moieties are chemically reactive to the binding domains, thereby locally capturing said binding domains upon contact before, during, or subsequent to the removing the fugitive ink.

20. The method of claim 18, wherein the coupling moieties comprise native extracellular matrix binding domains, antibodies, peptides, proteins, DNA, RNA, aptamers, nanoparticles, small molecules, chemical functional groups, and bacteria.

21. The method of claim 16, further comprising
- depositing a second set of one or more sacrificial filaments on or in the substrate to form an interpenetrating network of tubes, each of the sacrificial filaments of the second set of the one or more sacrificial filaments comprising a second fugitive ink; and
- removing the second fugitive ink, thereby forming the interpenetrating network of tubes in the tubular tissue construct.

22. The method of claim 16, wherein the tubular tissue construct is a nephron, intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph.

23. A method of printing a tubular tissue construct, the method comprising:
- depositing one or more cell-laden filaments each comprising a plurality of predetermined types of viable cells on or in the substrate to form one or more tissue patterns, each of the tissue patterns comprising at least two predetermined cell types, wherein each predetermined type of viable cells is deposited at a different predetermined location along a length of the cell-laden filament;
- depositing one or more sacrificial filaments on or in the substrate to form a functional channel pattern interpenetrating the one or more tissue patterns, each of the sacrificial filaments comprising a fugitive ink;
- at least partially surrounding the one or more tissue patterns and the functional channel pattern with an extracellular matrix composition,
- removing the fugitive ink to create functional channels in the extracellular matrix composition, thereby forming an interpenetrating channel network in a tissue construct.

24. The method of claim 23, wherein the tubular tissue construct is nephron, intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph.

* * * * *